US012697307B2

(12) United States Patent (10) Patent No.: US 12,697,307 B2
Thon (45) Date of Patent: Aug. 4, 2026

(54) COMPOSITIONS AND METHODS RELATED TO MEGAKARYOCYTE-DERIVED EXTRACELLULAR VESICLES

(71) Applicant: STRM.bio Incorporated, Cambridge, MA (US)

(72) Inventor: Jonathan Thon, Cambridge, MA (US)

(73) Assignee: STRM.bio Incorporated, Cambridge, MA (US)

( * ) Notice: Subject to any disclaimer, the term of this patent is extended or adjusted under 35 U.S.C. 154(b) by 853 days.

(21) Appl. No.: 17/924,758

(22) PCT Filed: May 11, 2021

(86) PCT No.: PCT/US2021/031778
§ 371 (c)(1),
(2) Date: Nov. 11, 2022

(87) PCT Pub. No.: WO2021/231425
PCT Pub. Date: Nov. 18, 2021

(65) Prior Publication Data
US 2023/0190815 A1 Jun. 22, 2023

Related U.S. Application Data

(60) Provisional application No. 63/173,725, filed on Apr. 12, 2021, provisional application No. 63/173,731, filed on Apr. 12, 2021, provisional application No. 63/173,732, filed on Apr. 12, 2021, provisional application No. 63/022,888, filed on May 11, 2020, provisional application No. 63/022,883, filed on May 11, 2020, provisional application No. 63/022,884, filed on May 11, 2020.

(51) Int. Cl.
| | |
|---|---|
| *A61K 9/50* | (2006.01) |
| *A61K 9/127* | (2025.01) |
| *A61K 35/19* | (2015.01) |
| *A61K 48/00* | (2006.01) |
| *C12N 5/078* | (2010.01) |
| *C12N 13/00* | (2006.01) |

(52) U.S. Cl.
CPC ............ *A61K 9/5068* (2013.01); *A61K 9/127* (2013.01); *A61K 35/19* (2013.01); *A61K 48/0033* (2013.01); *C12N 5/0644* (2013.01); *C12N 13/00* (2013.01); *C12N 2506/03* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 9,085,778 B2 | 7/2015 | Lötvall et al. | |
| 9,629,929 B2 | 4/2017 | Lötvall et al. | |
| 9,856,477 B2 | 1/2018 | Lötvall et al. | |
| 9,889,210 B2 | 2/2018 | Lötvall et al. | |
| 10,195,290 B1 | 2/2019 | Dooley et al. | |
| 10,370,663 B2 | 8/2019 | Lötvall et al. | |
| 10,538,738 B2 | 1/2020 | Papoutsakis et al. | |
| 10,561,740 B2 | 2/2020 | Dooley et al. | |
| 10,695,443 B2 | 6/2020 | Lötvall et al. | |
| 10,723,782 B2 | 7/2020 | Lewis et al. | |
| 11,512,315 B2 | 11/2022 | Sathyanarayanan et al. | |
| 2001/0005591 A1 | 6/2001 | Qasba et al. | |
| 2004/0152628 A9 | 8/2004 | Tandon et al. | |
| 2008/0069807 A1 | 3/2008 | Jy et al. | |
| 2008/0213377 A1 | 9/2008 | Bhatia et al. | |
| 2012/0238020 A1 | 9/2012 | Mitchell et al. | |
| 2012/0315338 A1 | 12/2012 | Li et al. | |
| 2012/0321723 A1 | 12/2012 | Bruno et al. | |
| 2016/0324897 A1* | 11/2016 | Ingber .................... A61K 31/64 | |
| 2017/0058262 A1* | 3/2017 | Papoutsakis ......... C12N 5/0644 | |
| 2018/0055891 A1 | 3/2018 | Zhao | |
| 2018/0328940 A1* | 11/2018 | Goetzl ............... G01N 33/5308 | |
| 2019/0202892 A1 | 7/2019 | Lewis et al. | |
| 2020/0115681 A1 | 4/2020 | Papoutsakis et al. | |
| 2022/0143095 A1 | 5/2022 | Hett et al. | |

FOREIGN PATENT DOCUMENTS

| | | | |
|---|---|---|---|
| WO | WO 2015/179301 A1 | 11/2015 | |
| WO | WO 2017/044149 A1 | 3/2017 | |
| WO | WO 2018/165308 A1 | 9/2018 | |
| WO | WO 2019/136318 A2 | 7/2019 | |
| WO | WO 2020/006539 A1 | 1/2020 | |
| WO | WO 2020/018950 A1 | 1/2020 | |

(Continued)

OTHER PUBLICATIONS

Kao, Chen-Yuan, and Eleftherios T. Papoutsakis. "Extracellular vesicles: exosomes, microparticles, their parts, and their targets to enable their biomanufacturing and clinical applications." Current opinion in biotechnology 60 (2019): 89-98. (Year: 2019).*
Aoyama, Keisuke, et al. "Stromal cell CD9 regulates differentiation of hematopoietic stem/progenitor cells." Blood, The Journal of the American Society of Hematology 93.8 (1999): 2586-2594. (Year: 1999).*
Kao, Chen-Yuan, and Eleftherios T. Papoutsakis. "Extracellular vesicles: exosomes, microparticles, their parts, and their targets to enable their biomanufacturing and clinical applications." Current opinion in biotechnology 60 (Mar. 7, 2019): 89-98. (Year: 2019).*
Lagrue-Lak-Hal, Anne-Hélène, et al. "Expression and function of the collagen receptor GPVI during megakaryocyte maturation." Journal of Biological Chemistry 276.18 (2001): 15316-15325. (Year: 2001).*

(Continued)

*Primary Examiner* — Bethany P Barham
*Assistant Examiner* — Peter Anthopolos
(74) *Attorney, Agent, or Firm* — Morgan, Lewis & Bockius LLP

(57) ABSTRACT

Disclosed herein are compositions and methods related to megakaryocyte-derived extracellular vesicles derived from human pluripotent stem cells, where the megakaryocyte-derived extracellular vesicles may be utilized for drug delivery and treating various diseases.

12 Claims, 15 Drawing Sheets

(56) References Cited

FOREIGN PATENT DOCUMENTS

| WO | WO 2020/113059 | A1 | 6/2020 | |
| WO | WO-2021123775 | A2 * | 6/2021 | .......... C12N 5/0644 |
| WO | WO 2021/138332 | A1 | 7/2021 | |
| WO | WO 2021/173828 | A1 | 9/2021 | |
| WO | WO 2022/081836 | A1 | 4/2022 | |

OTHER PUBLICATIONS

Flaumenhaft, Robert, et al. "Megakaryocyte-derived microparticles: direct visualization and distinction from platelet-derived microparticles." Blood, The Journal of the American Society of Hematology 113.5 (2009): 1112-1121. (Year: 2009).*

Gilligan, Cells 2020, 9, 224; doi:10.3390/cells9010224.

Kamerkar, Nature. Jun. 22, 2017; 546(7659): 498-503. doi:10.1038/nature22341.

Schlinker, Biotechnol Bioeng. Apr. 2015; 112(4): 788-800.

Kotmakç, J Pharm Pharm Sci 18(3) 396-413, 2015.

Arraud, et al., "Extracellular vesicles from blood plasma: determination of their morphology, size, phenotype and concentration," Journal of Thrombosis and Haemostasis, vol. 12, pp. 614-217, 2014.

Berge, et al., "Pharmaceutical Salts," Pharmaceutical Sciences, vol. 66, No. 1, 19, pages, 1977.

Brisson, et al., "Extracellular vesicles from activated platelets: a semiquantitative cryo-electron microscopy and immuno-gold labeling study," Platelets, vol. 28, No. 3, pp. 263-271, 2017.

Bulcha, et al., "Viral vector platforms within the gene therapy landscape," Signal Transduction and Targeted Therapy, vol. 6, No. 53, 24 pages, 2021.

Epstein, "Cosmeceutical vehicles," Clinics in Dermatology, vol. 27, pp. 453-460, 2009.

Escobar, et al., "Human megakaryocytic microparticles induce de novo platelet biogenesis in a wild-type murine model," Blood Advances, vol. 4, No. 5, pp. 804-814, 2020.

Flaumenhaft, et al., "Megakaryocyte-derived microparticles: direct visualization and distinction from platelet-derived microparticles," Blood, vol. 113, No. 5, pp. 1112-1121, 2009.

French, et al., "Platelet-derived extracellular vesicles infiltrate and modify the bone marrow during inflammation," Blood Advances, vol. 4, No. 13, pp. 3011-3023, 2020.

Jiang, et al., "How do megakaryocytic microparticles target and deliver cargo to alter the fate of hematopoietic stem cells?" J Control Release, vol. 247, pp. 1-18, 2017.

Jiang, et al., "Shear enhances thrombopoiesis and formation of microparticles that induce megakaryocytic differentiation of stem cells," Blood, vol. 124, No. 13, pp. 2094-2103, 2014.

Kao, et al., "Engineering human megakaryocytic microparticles for targeted delivery of nucleic acids to hematopoietic stem and progenitor cells," Sci. Adv., vol. 4, 11 pages, 2018.

Kao, et al., "Extracellular vesicles: exosomes, microparticles, their parts, and their targets to enable their biomanufacturing and clinical applications," Current Opinion in Biotechnology, vol. 60, pp. 89-98, 2019.

Stahl, et al., "Handbook of Pharmaceutical Salts: Properties, Selection, and Use," Journal of Medicinal Chemistry, vol. 46, No. 7, pp. 1277-1278, 2003.

Zeltner, et al., "Near-perfect infectivity of wild-type AAV as benchmark for infectivity of recombinant AAV vectors," Gene Ther., vol. 17, No. 7, pp. 872-879, 2010.

Zhou, et al., "A pneumonia outbreak associated with a new coronavirus of probable bat origin," Nature, vol. 579, 20 pages, 2020.

International Search Report & Written Opinion PCT Application No. PCT/US21/31778, dated Sep. 14, 2021, 9 pages.

Kanada, et al., "Differential fates of biomolecules delivered to target cells via extracellular vesicles," PNAS, vol. 112, No. 12, pp. E1433-E1442, Feb. 23, 2015.

* cited by examiner

Negative control

Mix dimer CD41-CD61-PEVs CD41-CD61

CD41/CD61+MkEVs

FIG. 3A                    FIG. 3B                    FIG. 3C
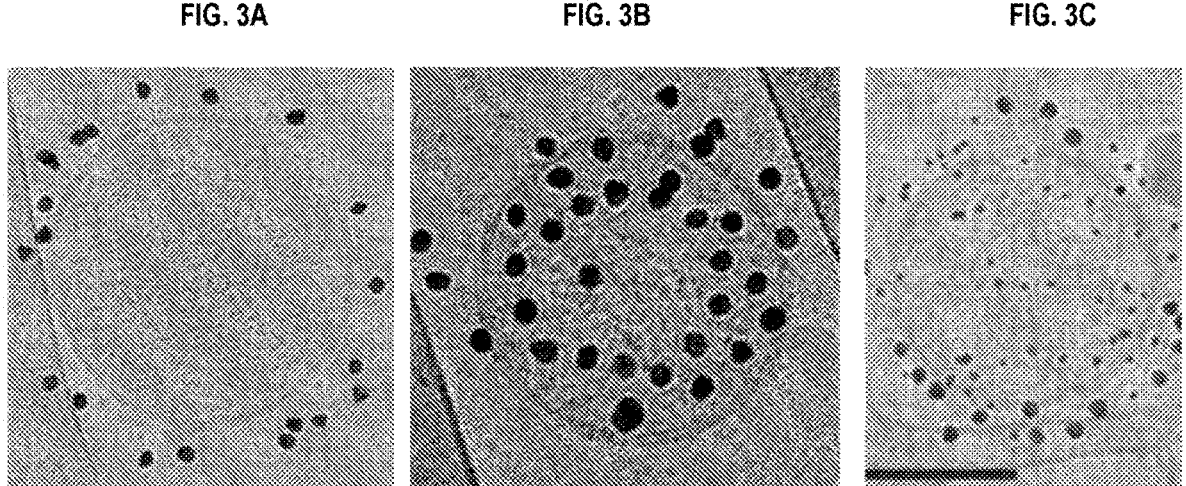

FIG. 4D                                    FIG. 4E
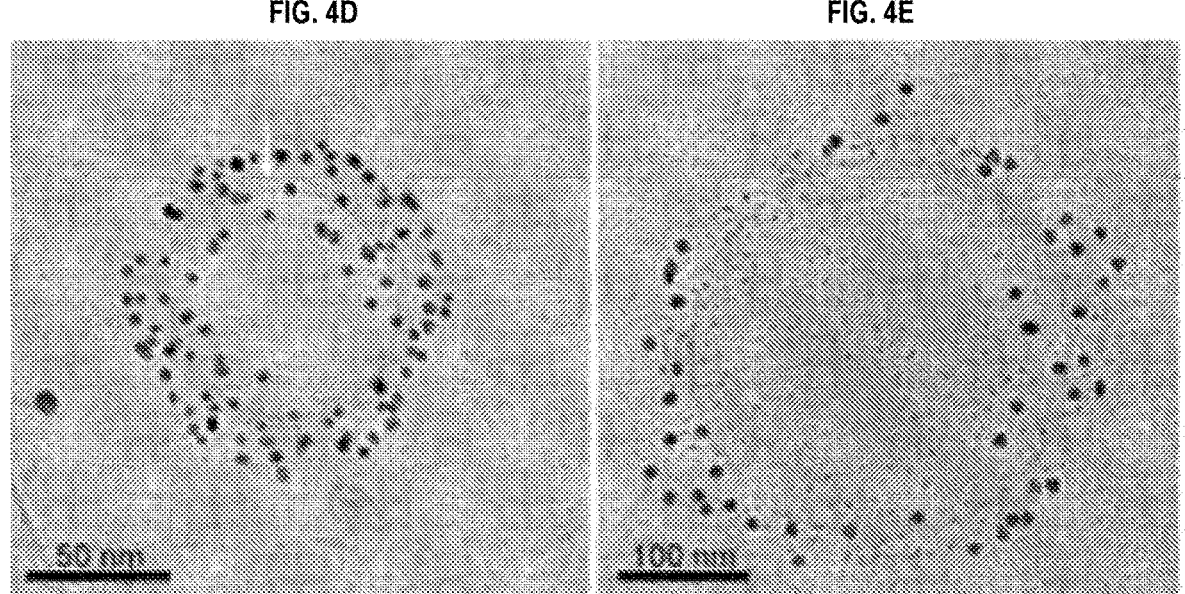

Unfiltered MkEV Product

650nm Filtered MkEV Product

COMPOSITIONS AND METHODS RELATED TO MEGAKARYOCYTE-DERIVED EXTRACELLULAR VESICLES

CROSS-REFERENCE TO RELATED APPLICATIONS

This application claims the benefit of priority to U.S. Provisional Patent Application No. 63/022,883, filed May 11, 2020, 63/022,884, filed May 11, 2020, 63/022,888, filed May 11, 2020, 63/173,725, filed Apr. 19, 2021, 63/173,731, filed Apr. 19, 2021, and 63/173,732, filed Apr. 19, 2021, all of which are incorporated by reference herein in their entireties.

FIELD

The present disclosure relates to compositions and methods related to megakaryocyte-derived extracellular vesicles derived from human pluripotent stem cells.

BACKGROUND

The direct administration of therapeutic agents to patients without the use of delivery vehicles, as is the case in some chemotherapy administrations to treat cancer or deliver gene therapies, has several disadvantages, including rapid clearance, poor bioavailability, low delivery to target cells or tissues, unspecific cytotoxicity, and consequent systemic side effects. To overcome these challenges, a variety of synthetic nanodelivery vehicles have been developed, some of which are clinically approved.

Treatment using nanodelivery vehicles can have several advantages, including reducing renal clearance, improving site-specific delivery, simultaneous delivery of multiple therapeutic agents, protection from enzymatic degradation, immunoevasion, sequential multistage release, stimuli-responsive activation, and theranostic capabilities, among others. Nevertheless, the majority of these features are not yet in clinical use, partially due to complex and costly manufacturing required to achieve multi-functionality. The largest category of clinically approved nanoparticles is liposomes, which consist of a simple lipid bilayer surrounding an aqueous compartment. Liposomes are versatile drug delivery vehicles, as both the lipid membrane and interior space can be utilized for loading of hydrophobic and hydrophilic drugs, respectively. However, liposomes can also trigger adverse effects in a patient, including immune reactions and cytotoxicity, in addition to target non-specificity and inefficient unloading of therapeutic agents, because liposomes are foreign, synthetic entities, with limited cell or tissue targeting machinery. Adenovirus, retrovirus, AAV, and lentivirus vectors are currently the most popular viral vectors for gene therapy today; comprising 20%, 16%, 8%, and 8% of active gene therapy clinical trials, respectively (Linden et al., 2010, Bulcha et al., Sig. Transduct. Target Ther. 6:53 (2021)). Next generation approaches have used various technologies to improve production, expression, and safety profiles. Examples include development of technology to manufacture scalable, replication competent adenovirus-free adenoviral vectors, and incorporation or deletion of genetic sequences to enhance transgene expression or create self-inactivating lentiviral vectors, respectively.

Nevertheless, conventional methods of viral vector production using adherent cell lines and transient transfections in the presence of serum are not scalable. In addition to targeting, scalability of manufacture, immunogenicity, and safety concerns, several additional virus-dependent limitations to gene delivery exist. For instance, retroviruses can only infect dividing cells, and risk insertional mutagenesis. Adenoviruses are known to cause respiratory infections in humans and can cause severe inflammatory reactions. The lack of a viral envelope results in broad uptake in cells, thereby reducing cell specificity. Adeno associated viruses (AAV) has a limited packaging capacity and low transduction efficiencies. Further, lentivirus has a risk of insertional mutagenesis and possible risk of generating replication-competent lentiviruses. Also, for herpes virus, antibodies against such are commonly produced and can result in rapid clearance. Moreover, there is a risk of producing infectious strains.

Accordingly, there is a need for delivery vehicles that can be generated cost-effectively at scale and that eliminate or reduce adverse effects when administered to a patient.

SUMMARY

Disclosed herein are compositions and methods related to megakaryocyte-derived extracellular vesicles. Specifically, inter alia, the present megakaryocyte-derived extracellular vesicles demonstrate a unique biomarker profile and/or size profile, which make them well-suited for utilization in therapeutic delivery and treating various diseases or disorders. In various embodiments, the compositions and methods disclosed herein may be utilized for drug delivery and treatment of one or more genetic disorders. In some embodiments, the compositions and methods disclosed herein may be utilized for drug delivery and treatment of infectious diseases. In some embodiments, the compositions and methods disclosed herein may be utilized for drug delivery and treatment of a disease or disorder of hematopoiesis, e.g. thrombocytopenias/anemias. In some embodiments, the compositions and methods disclosed herein may be utilized for drug delivery and treatment of hemoglobinopathies. The methods disclosed herein may be in vivo or ex vivo and may be used in for example, gene replacement therapy and gene-editing.

In one aspect, the present invention relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA and the lipid bilayer membrane comprises one or more proteins associated with or embedded within.

In another aspect, the present invention relates to a pharmaceutical composition comprising a composition disclosed herein and a pharmaceutically acceptable excipient or carrier.

In another aspect, the present invention relates to a method for transferring a deliverable therapeutic agent, comprising: (a) obtaining the megakaryocyte-derived extracellular vesicles of a composition disclosed herein; (b) incubating the megakaryocyte-derived extracellular vesicle with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In another aspect, the present invention relates to a method of generating the megakaryocyte-derived extracellular vesicles of a composition disclosed herein, comprising: (a) obtaining a human pluripotent stem cell, the human pluripotent stem cell being a primary CD34+ hematopoietic stem cell sourced from peripheral blood or cord blood; (b) differentiating the human pluripotent stem cell to a megakaryocyte in the absence of added erythropoietin and in the presence of added thrombopoietin; and (c) isolating megakaryocyte-derived extracellular vesicles from the megakaryocytes.

In various embodiments, the compositions and methods disclosed herein may be utilized for drug delivery and treatment of one or more genetic disorders.

In another aspect, the present invention relates to a method for treating or preventing an infectious disease, comprising administering an effective amount of a composition disclosed herein.

In another aspect, the present invention relates to a method for treating or preventing an infectious disease, comprising administering an effective amount of a composition comprising a cell, which is contacted with a composition disclosed herein in vitro.

In another aspect, the present invention relates to a method for treating a disease or disorder of hematopoiesis. In an aspect, the present invention relates to a method for treating a thrombocytopenia, comprising administering an effective amount of a composition disclosed herein, wherein the composition comprises megakaryocyte-derived extracellular vesicles which comprise a nucleic acid encoding a functional thrombocytopenia-related gene, or a protein product thereof, or a nucleic acid encoding a gene-editing protein capable of creating a functional thrombocytopenia-related gene, or a protein product thereof.

In another aspect, the present invention relates to a method for treating a thrombocytopenia, comprising administering an effective amount of a composition comprising a cell which is contacted with a composition disclosed herein in vitro, wherein the composition comprises megakaryocyte-derived extracellular vesicles which comprise a nucleic acid encoding a functional thrombocytopenia-related gene, or a protein product thereof, or a nucleic acid encoding a gene-editing protein capable of creating a functional thrombocytopenia-related gene, or a protein product thereof.

In another aspect, the present invention relates to a method for treating a hemoglobinopathy, comprising administering an effective amount of a composition disclosed herein, wherein the composition comprises megakaryocyte-derived extracellular vesicles which comprise a nucleic acid encoding a functional hemoglobinopathy-related gene, or a protein product thereof, or a nucleic acid encoding a gene-editing protein capable of creating a functional hemoglobinopathy-related gene, or a protein product thereof.

In another aspect, the present invention relates to a method for treating a hemoglobinopathy, comprising administering an effective amount of a composition comprising a cell which is contacted with a composition disclosed herein in vitro, wherein the composition comprises megakaryocyte-derived extracellular vesicles which comprise a nucleic acid encoding a functional hemoglobinopathy-related gene, or a protein product thereof, or a nucleic acid encoding a gene-editing protein capable of creating a functional hemoglobinopathy-related gene, or a protein product thereof.

or "MVs"), with the duration of each stage, timing of harvest, and associated yields indicated.

Figure 1A:
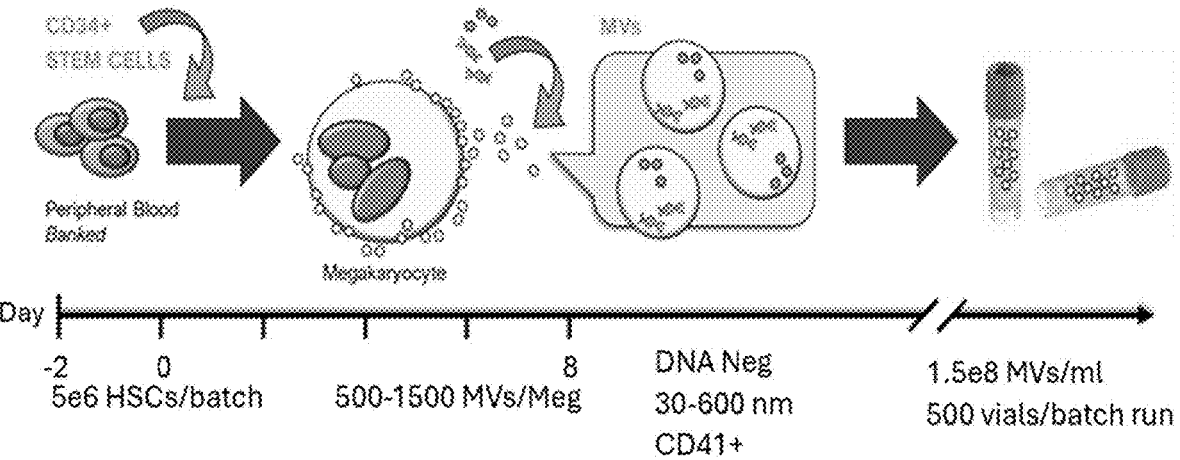
FIG. 1A is a schematic showing the differentiation steps of megakaryocyte-derived extracellular vesicles ("MkEVs"
Figure 1B:
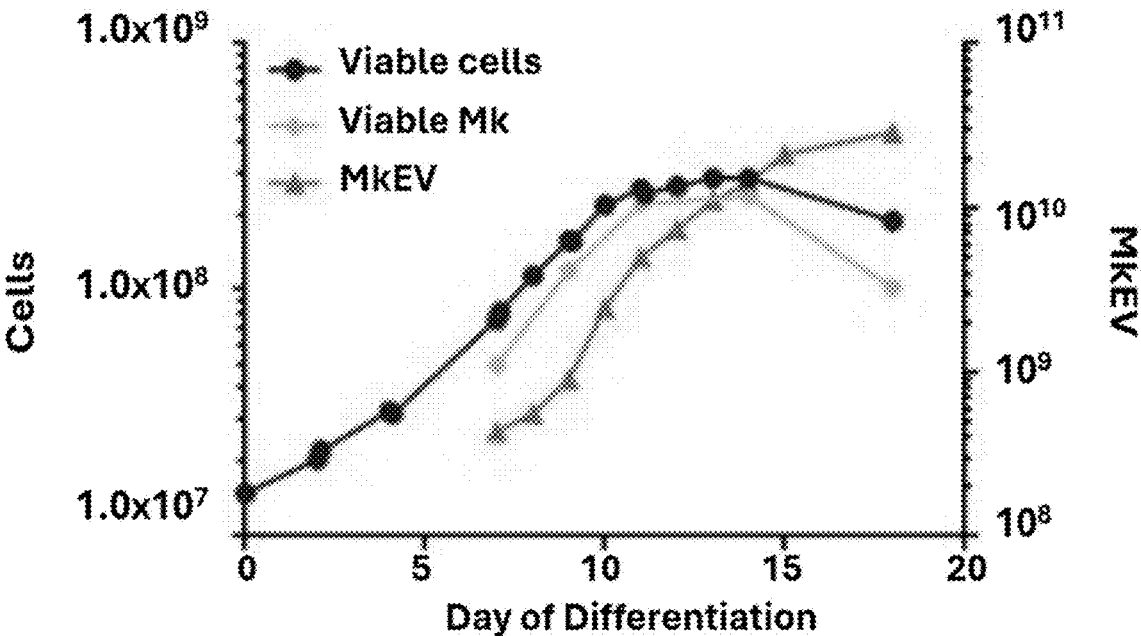
Figure 1C:
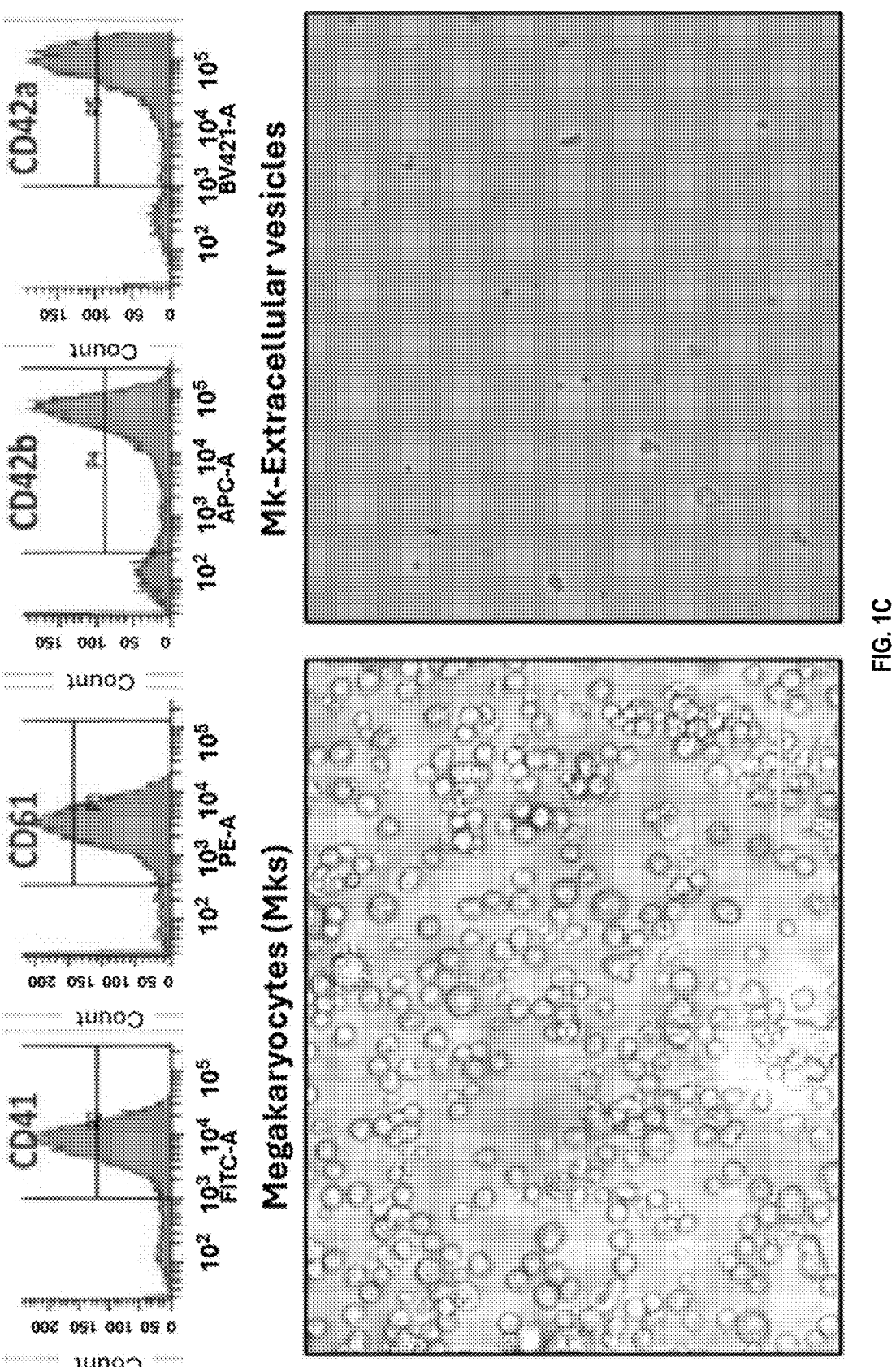

FIG. 1B is a graph of experimental data showing that the yield of megakaryocyte-derived extracellular vesicles increases over time during in vitro megakaryocyte (Mk) differentiation. For reference, at the last point, the order top to bottom is MkEV, viable cells, and viable MK. FIG. 1C is experimental data showing the phenotype of MkEVs in culture. Top panel: Representative histograms of cellular surface marker expression. Bottom panel: Representative microscopy images of megakaryocytes (left), and harvested MkEVs (right).

Figure 2A:
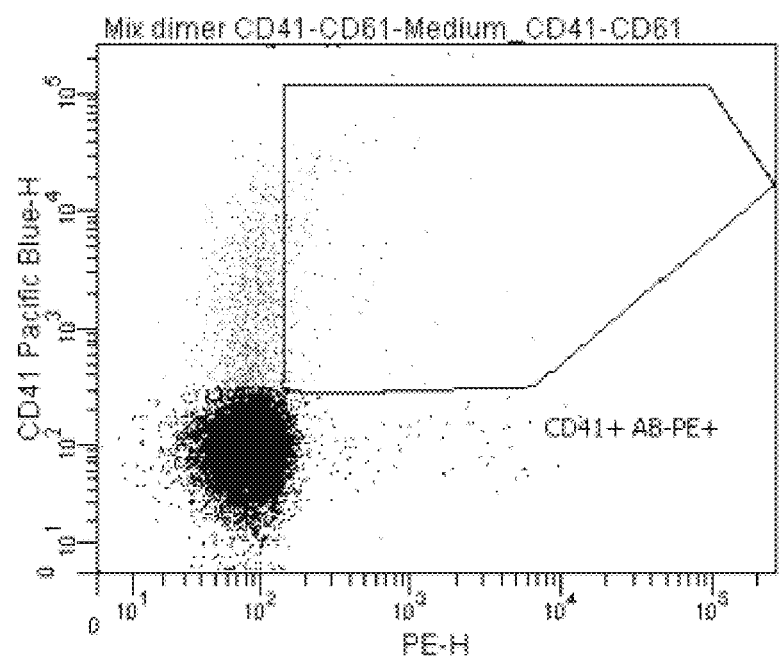
Figure 2B:
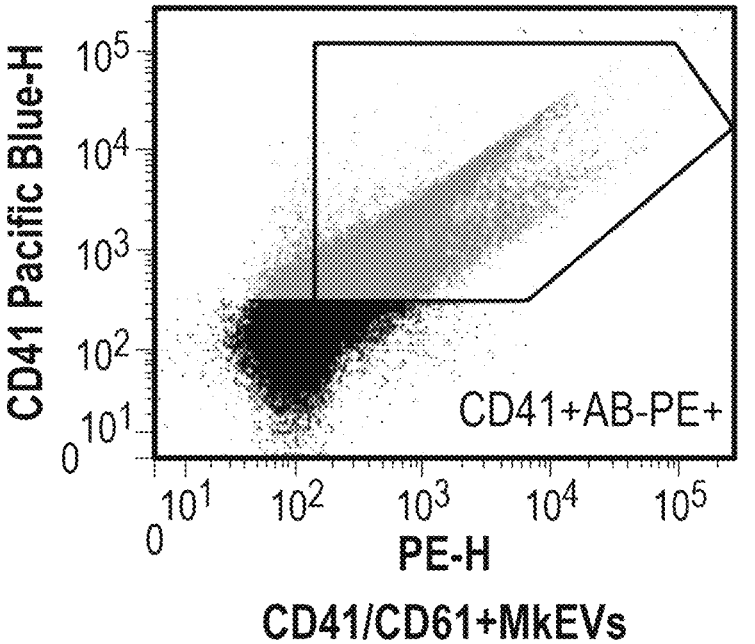
Figure 2C:
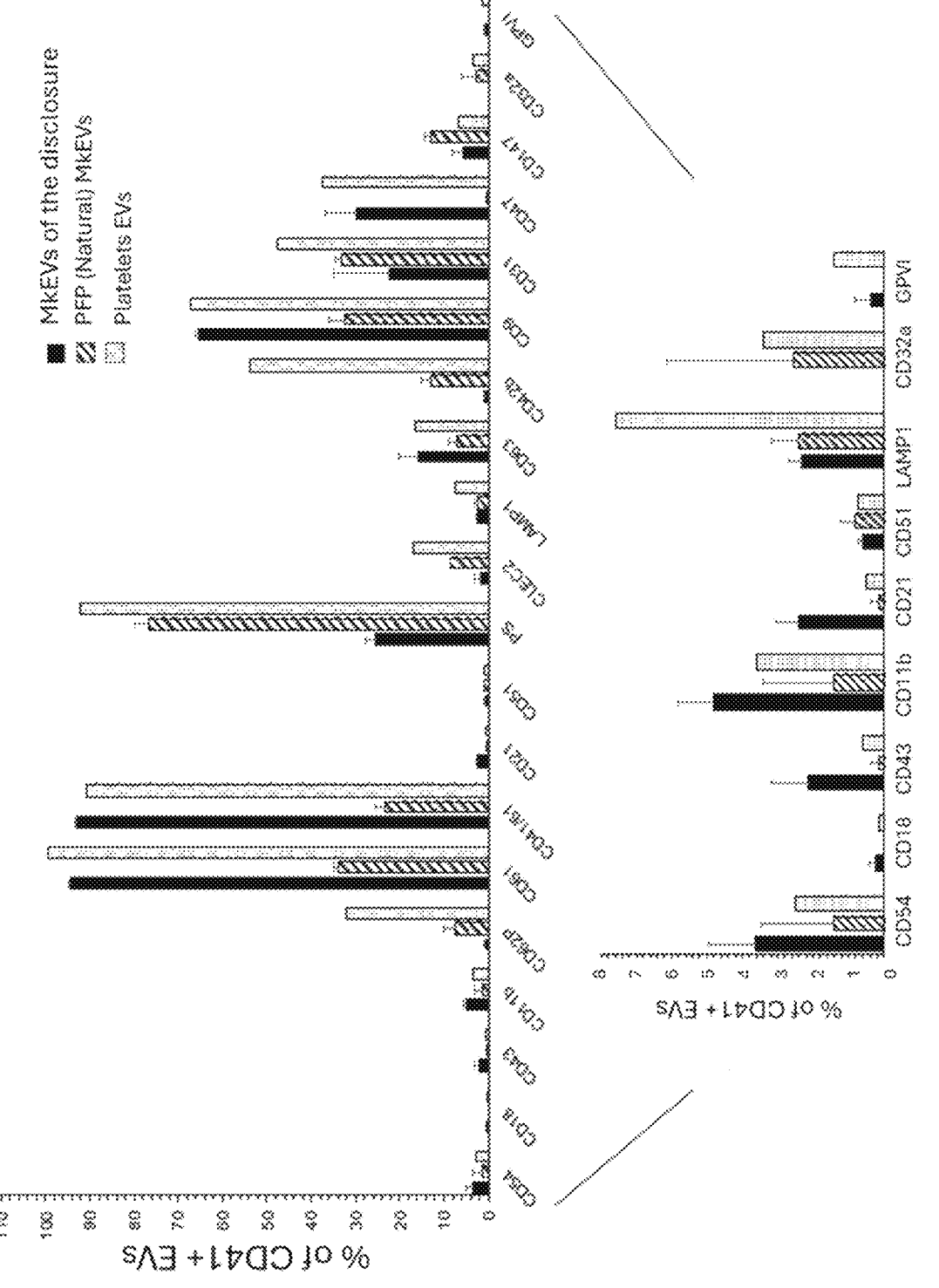
Figure 2D:
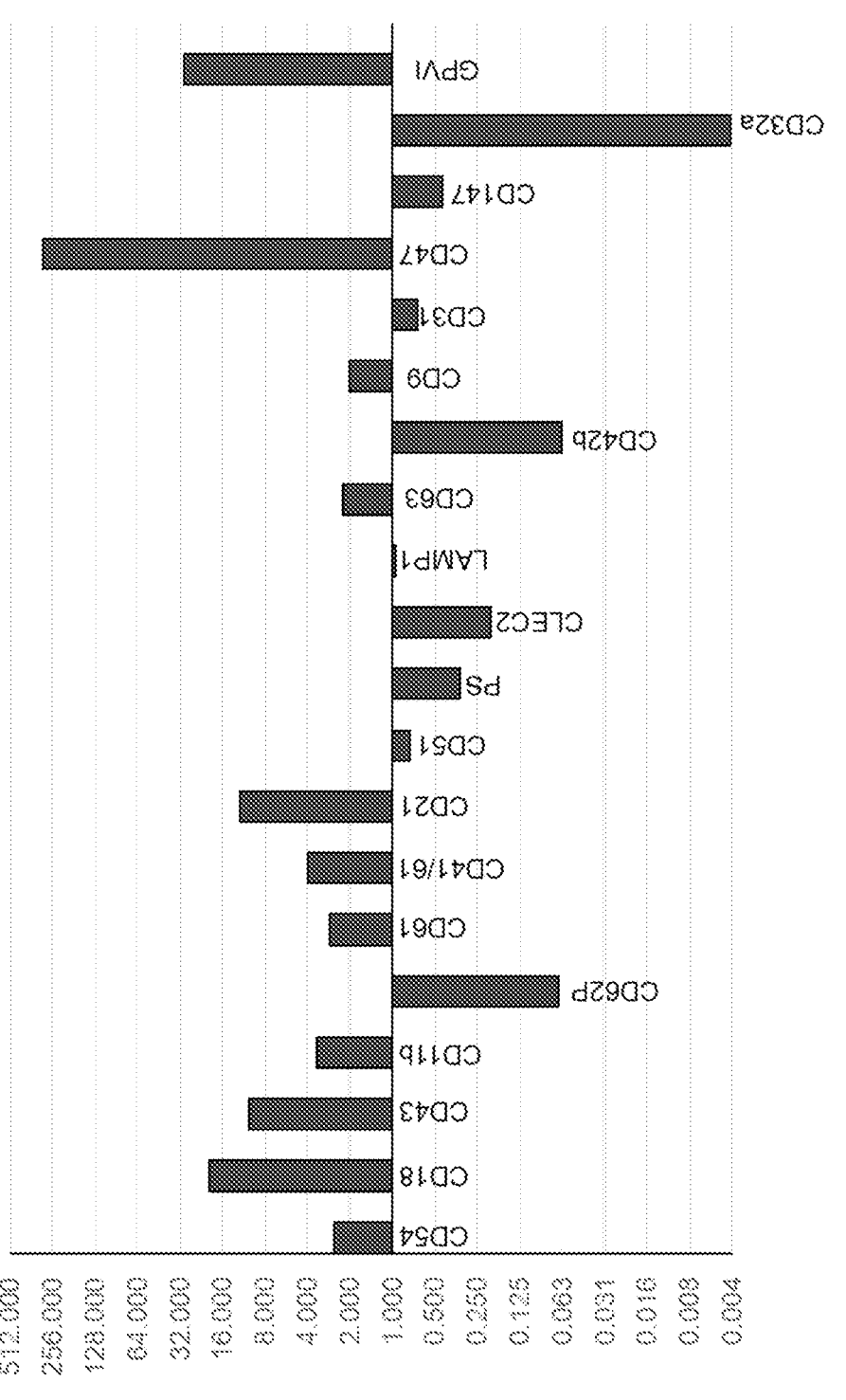
Figure 2E:
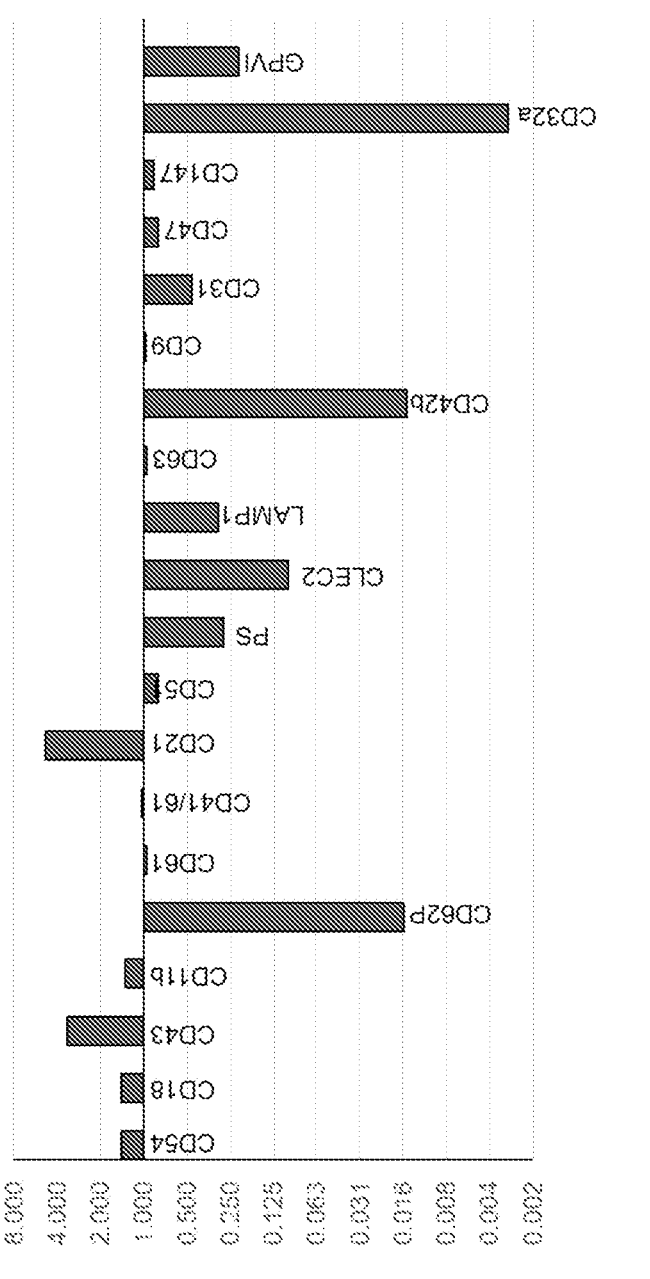
Figure 2F:
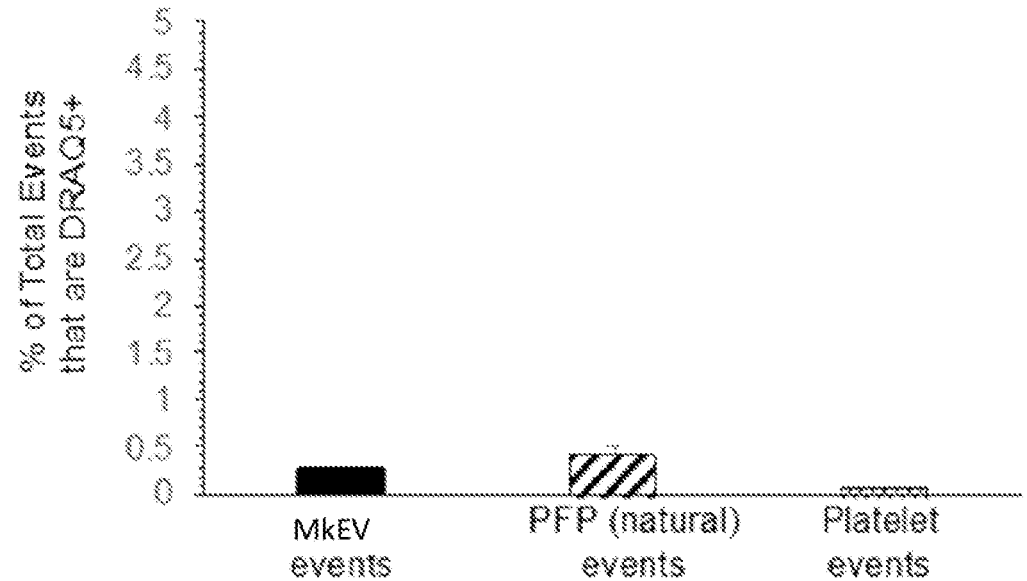

FIGS. 2A-2F demonstrate experimental data showing MkEV biomarker expression. Surface marker expression of MkEVs of the disclosure were compared to platelet-free plasma (PFP) MkEVs and platelet-derived EVs (PLT EVs). FIGS. 2A-2B are representative graphs demonstrating the flow cytometry gating strategy. FIG. 2C is a representative graph demonstrating the marker profile of CD41+ MkEVs of the disclosure, CD41+ PFP MkEVs, and CD41+ PLT EVs. MkEVs of the disclosure have different surface marker phenotypes compared to naturally occurring MkEVs and platelet-derived EVs. Differential expression of surface markers co-expressed on CD41+ STRM MkEVs (black bars) when compared to CD41+ naturally occurring platelet free plasma (PFP) MkEVs (hashed bars) and CD41+ platelet-derived EVs (dotted bars). For MkEVs of the disclosure and PFP MkEVs, bars represent average percent ±standard deviation, n=2 biologic replicates. Fold change is relative to PFP EVs. FIG. 2D is a representative graph demonstrating the fold change in marker expression between MkEVs of the disclosure and PFP MkEVs. For CD32a, GPVI, and CD18, fold change calculations were made by changing values of 0 to 0.01. FIG. 2E is a representative graph demonstrating the fold change in marker expression between MkEVs of the disclosure and PLT EVs. For CD32a, fold change calculations were made by changing values of 0 to 0.01. The data shows that MkEVs of the disclosure exhibit different expression of surface markers compared to PFP MkEVs and PLT EVs and establish a marker profile of the present MkEVs relative to PFP MkEVs and PLT EVs. FIG. 2F is a representative graph demonstrating the minimal presence of DRAQ5 positive events showing the lack of cellular contamination.

FIGS. 3A-3B are electron microscopic images demonstrating MkEV characterization, including size and morphology. FIG. 3A is a cryo-EM image of MkEVs of the disclosure with immunogold labeling of CD41. FIG. 3B is a cryo-EM image of MkEVs of the disclosure with immunogold labeling of phosphatidylserine. Measuring of MkEVs in cryo-EM images showed a range of MkEV sizes between 100-500 nm, averaging ~250 nm in diameter. FIG. 3C is an image of MkEVs isolated from PFP plasma with co-staining of CD41 (large dots) and PS (small dots).

Figure 4A:
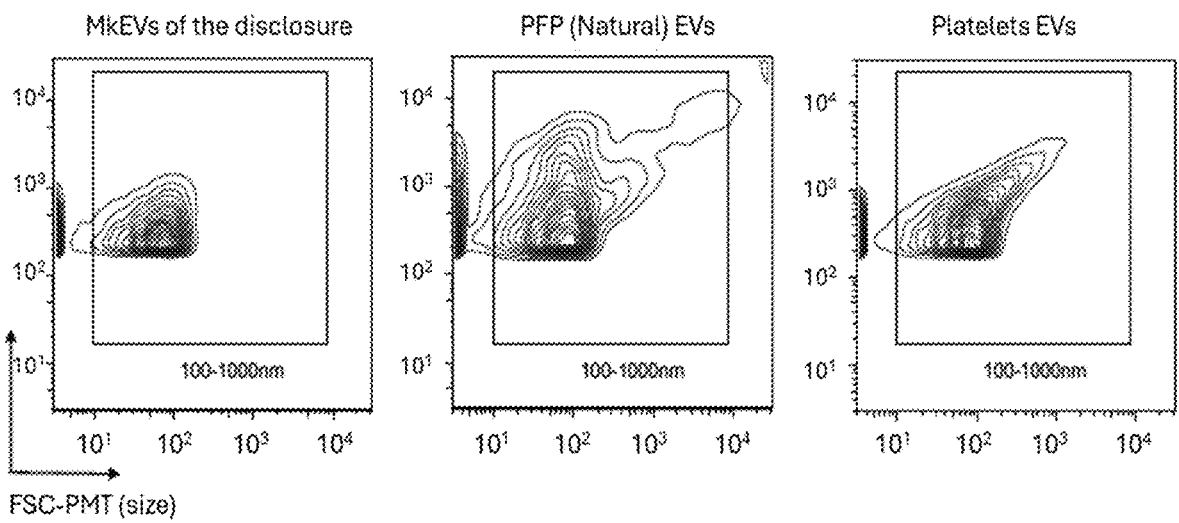

FIG. 4A shows the size distribution (nm) of CD41+ MkEVs of the disclosure compared to CD41+ PFP MkEVs and platelet EVs. Flow cytometric analysis with fluorescent CD41+ antibody labeling was used.

Figure 4B:
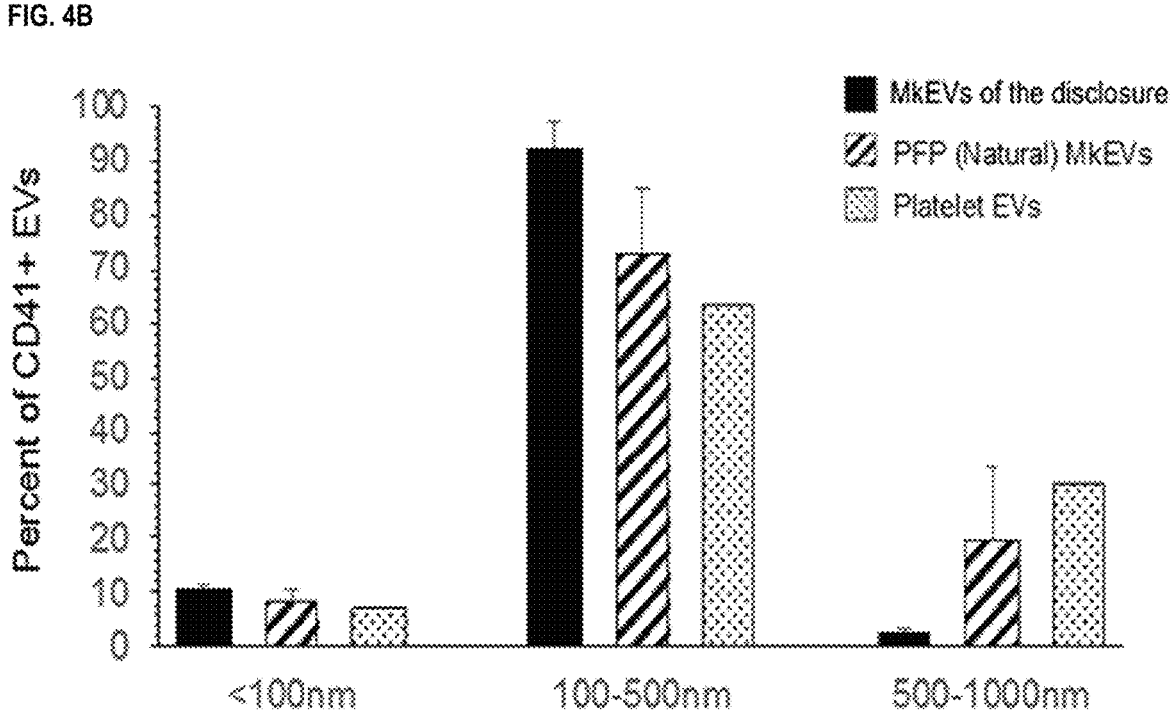
Figure 4C:
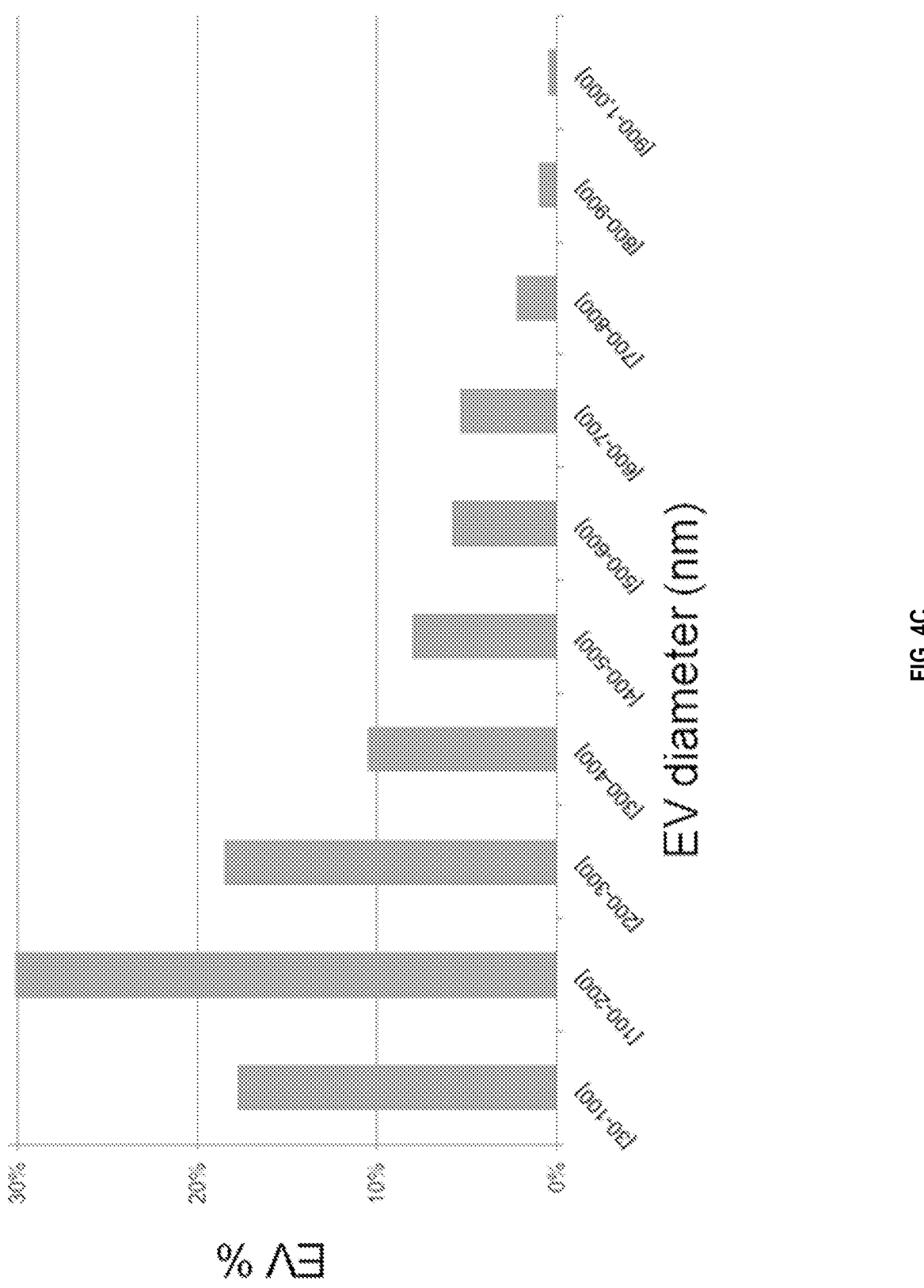
Figures 4F, 4G, 4H, 4I, 4J, 4K:
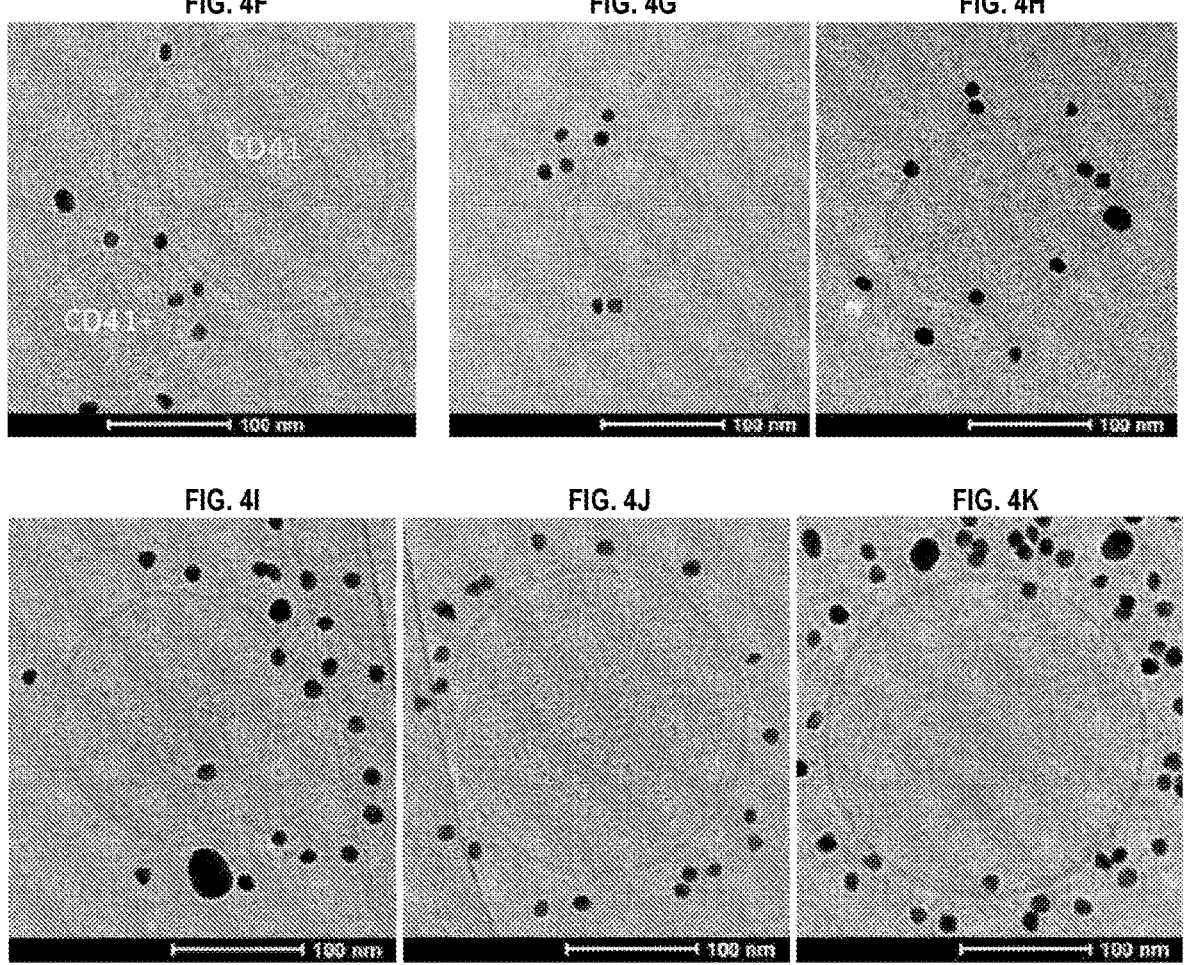

FIG. 4B is a graph showing the size distribution of the CD41+ MkEVs of the disclosure compared to CD41+ PFP (Natural MkEVs and platelet CD41+ EVs. FIG. 4C is a graph showing the percent size distribution of the EVs (nm). FIGS. 4D-4E are cryo-EM images of PFP MkEVs. FIGS. 4F-4K are cryo-EM images of MkEVs of the disclosure. Cd41+ Immunogold labeling was used and visible as black dots.

Figure 5A:
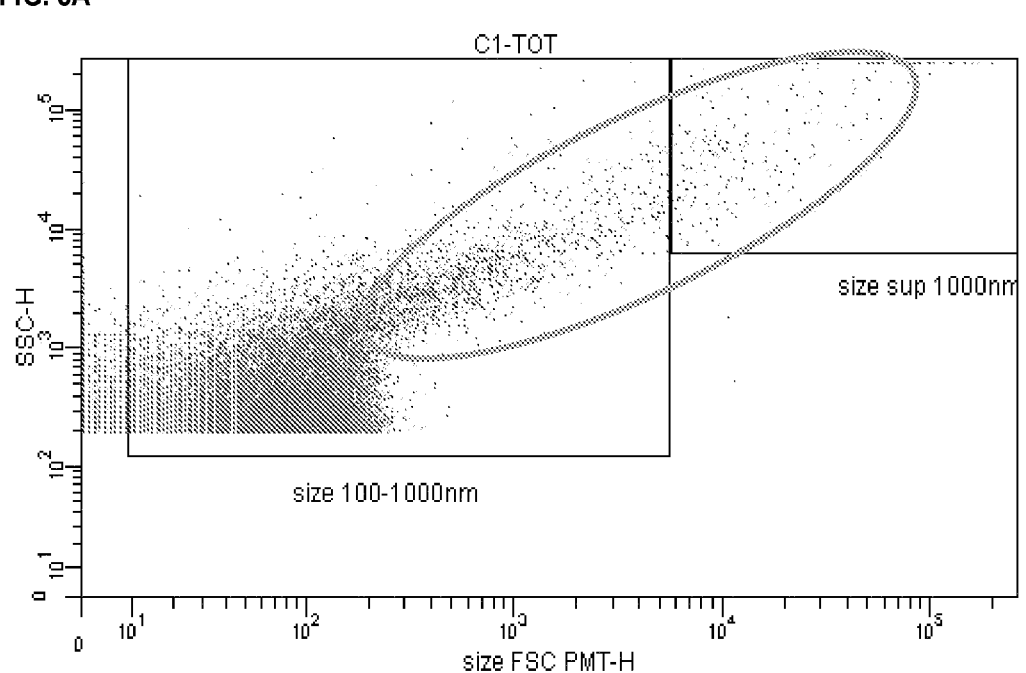
Figure 5B:
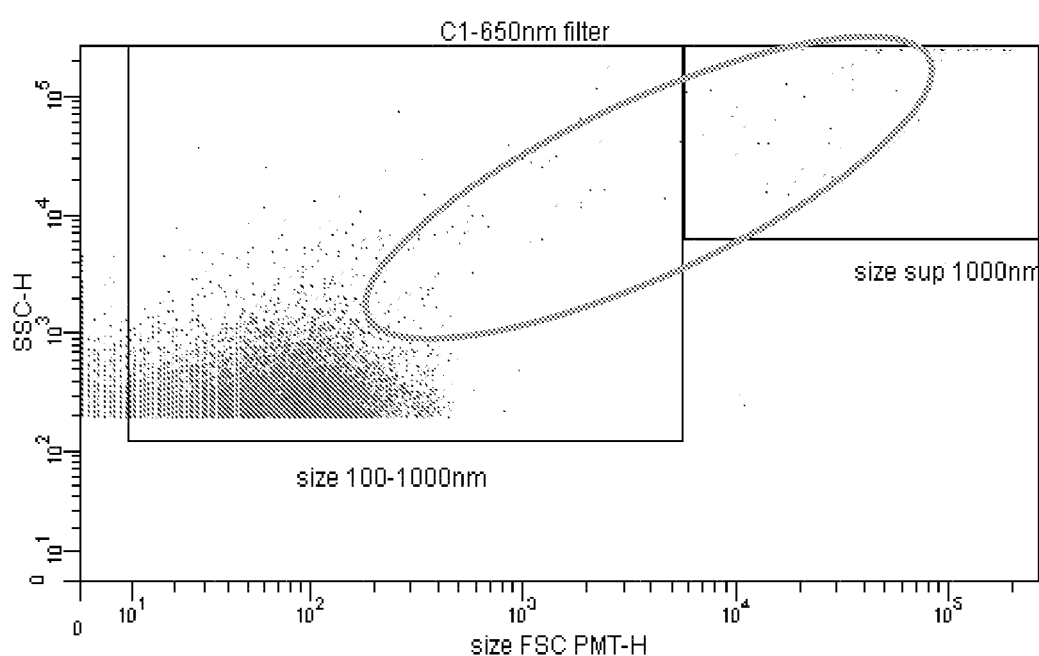

FIGS. 5A-5B are graphs of experimental data showing that size exclusion filtration effectively removes aggregates from unfiltered product. FIG. 5A shows unfiltered MkEV product. FIG. 5B shows 650-nm filtered MkEV product. Successful clearance of large aggregate material (observed by EM in frozen MkEV samples) was demonstrated by post-harvest filtration with 650 nm size exclusion filter. Images are from flow cytometry experiments.

FIGS. 6A-6H are graphs of experimental data showing EV characterization. EVs were collected from media containing mature, cultured MKs 24 hours after megakaryocyte isolation and purification. Isolated human platelets were stimulated with either thrombin (0.1 U/mL) and collagen (1 μg/mL) (traditional platelet agonists) or LPS (5 μg/mL). EV number/platelet and size were measured via nanoparticle tracking analysis (FIGS. 6A, 6B, 6E, and 6F) and CD41 receptor positivity and amount by electron microscopy (FIGS. 6C, 6D, 6G, and 6H).

DETAILED DESCRIPTION

The present invention is based, in part on the discovery of compositions and methods for making substantially purified megakaryocyte-derived extracellular vesicles that are characterized by particular sets of physical characteristics, such as biomarker composition (e.g. the presence, absence, or amount of a biomarker) and size, and can carry cargo in the lumen for use in delivering therapeutic agents. In some embodiments, the megakaryocyte-derived extracellular vesicles of the disclosure are distinct from the naturally occurring products, which are collected from whole blood (Platelet Free Plasma) or derived from activated platelets (Platelet EVs). Accordingly, in aspects, the present invention provides compositions and methods of obtaining and using megakaryocyte-derived extracellular vesicles that are consistently produced, with desirable properties, and carry specific cargo—making their therapeutic use more likely to be successful.

Megakaryocyte-derived extracellular vesicles, which are relatively immune silent, can be repeatedly dosed; a distinct advantage when compared to immunogenic viral vectors. In some aspects, the megakaryocyte-derived extracellular vesicles are useful for in vivo genomic medicines that do not need conditioning treatments, so people can receive them in an outpatient setting. This platform is an important paradigm shift in gene therapy from ex vivo to in vivo delivery, that will democratize gene therapy by reducing time to treatment and cost.

In one aspect, the present invention relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA and the lipid bilayer membrane comprises one or more proteins associated with or embedded within. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the megakaryocyte-derived extracellular vesicles.

In another aspect, the present invention relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle comprises one or more nucleic acid molecules selected from mRNA, tRNA, rRNA, siRNA, microRNA, regulating RNA, and non-coding and coding RNA associated with the surface of the vesicle, and the lipid bilayer membrane comprises one or more proteins associated with or embedded within. In some embodiments, the nucleic acid molecule is exogenously derived. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the megakaryocyte-derived extracellular vesicles.

In one aspect, the present invention relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicles are suitable for loading with cargo into the lumen and the lipid bilayer membrane comprises one or more proteins associated with or embedded within. In some embodiments, the cargo is one or more therapeutic agents, including therapeutic agents described herein. In some embodiments, the cargo comprises one or more megakaryocyte-derived nucleic acid molecules selected from mRNA, tRNA, rRNA, siRNA, microRNA, regulating RNA, and non-coding and coding RNA. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the megakaryocyte-derived extracellular vesicles. In some embodiments, the megakaryocyte-derived extracellular vesicles are suitable for loading with cargo associated with the surface of the megakaryocyte-derived extracellular vesicles.

In another aspect, the present invention relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle lumen comprises cargo and the lipid bilayer membrane comprises one or more proteins associated with or embedded within. In some embodiments, the cargo is one or more therapeutic agents, including therapeutic agents described herein. In some embodiments, the cargo comprises one or more megakaryocyte-derived nucleic acid molecules selected from mRNA, tRNA, rRNA, siRNA, microRNA, regulating RNA, and non-coding and coding RNA. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the megakaryocyte-derived extracellular vesicles. In some embodiments, the megakaryocyte-derived extracellular vesicles are suitable for loading with cargo associated with the surface of the megakaryocyte-derived extracellular vesicles.

In another aspect, the present invention relates to a pharmaceutical composition comprising a composition disclosed herein and a pharmaceutically acceptable excipient or carrier.

In another aspect, the present invention relates to a method for transferring a deliverable therapeutic agent, comprising: (a) obtaining the megakaryocyte-derived extracellular vesicles of a composition disclosed herein; (b) incubating the megakaryocyte-derived extracellular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In another aspect, the present invention relates to a method of generating the megakaryocyte-derived extracellular vesicles of a composition disclosed herein, comprising: (a) obtaining a human pluripotent stem cell, the human pluripotent stem cell being a primary CD34+ hematopoietic stem cell sourced from peripheral blood or cord blood or bone marrow; (b) differentiating the human pluripotent stem cell to a megakaryocyte in the absence of added erythropoietin and in the presence of added thrombopoietin; and (c) isolating megakaryocyte-derived extracellular vesicles from the megakaryocytes.

In another aspect, the present invention relates to a method for treating various diseases or disorders with the present megakaryocyte-derived extracellular vesicles.

Biomarker Profile or Fingerprint

In various embodiments, the present megakaryocyte-derived extracellular vesicles are characterized by a unique biomarker profile or fingerprint that distinguishes them from, for instance, naturally-occurring megakaryocyte-derived extracellular vesicles and/or vesicles or extracellular vesicles derived from platelets. In various embodiments, the present megakaryocyte-derived extracellular vesicles are characterized by a such a biomarker profile or fingerprint, which comprises the identity (e.g. the presence or absence) or amount (e.g. substantial presence or substantial absence of a biomarker in a megakaryocyte-derived extracellular vesicle population; or presence on or absence from a majority of megakaryocyte-derived extracellular vesicle in a population; or percentage megakaryocyte-derived extracellular vesicles having a biomarker).

In some embodiments, the composition comprises substantially purified megakaryocyte-derived extracellular vesicles comprising a lipid bilayer membrane surrounding a lumen and derived from a human pluripotent stem cell, wherein the lipid bilayer membrane comprises one or more proteins (a.k.a. biomarkers) associated with or embedded within.

In embodiments, the lipid bilayer membrane comprises proteins selected from CD54, CD18, CD43, CD11b, CD62P, CD41, CD61, CD21, CD51, phosphatidylserine (PS), CLEC-2, LAMP-1 (CD107a), CD63, CD42b, CD9, CD31, CD47, CD147, CD32a, and GPVI.

In embodiments, the lipid bilayer membrane comprises phosphatidylserine, e.g., without limitation by testing for Annexin V.

In embodiments, the lipid bilayer membrane comprises one or more proteins selected from CD62P, CD41, and CD61.

In embodiments, greater than about 40%, greater than about 50%, greater than about 60%, greater than about 70%, greater than about 80%, greater than about 90%, greater than about 95%, or greater than about 99% of the megakaryocyte-derived extracellular vesicles comprising a lipid bilayer membrane comprising CD41 also comprise CD61 in the lipid bilayer membrane.

In embodiments, the present megakaryocyte-derived extracellular vesicles are characterized by the expression and/or presence of one or more of CD54, CD18, CD43, CD11 b, CD62P, CD41, CD61, CD21, CD51, and CLEC-2. In embodiments, the present megakaryocyte-derived extracellular vesicles are characterized by the expression and/or presence of one or more of PS, CD62P, LAMP-1 (CD107a), CD42b, CD9, CD43, CD31, and CD11b. In embodiments, the present megakaryocyte-derived extracellular vesicles are characterized by the expression and/or presence of one or more of PS, CD61, CD62P, LAMP-1 (CD107a), CLEC-2, and CD63. In embodiments, the present megakaryocyte-derived extracellular vesicles are characterized by the expression and/or presence of one or more of PS, CD62P, CLEC-2, CD9, CD31, CD147, CD32a, and GPVI. In embodiments, the present megakaryocyte-derived extracellular vesicles are characterized by the expression and/or presence of one or more of PS, CD62P, LAMP-1 (CD107a), CLEC-2, CD9, and CD31. In embodiments, the present megakaryocyte-derived extracellular vesicles are characterized by the expression and/or presence of one or more of CD62P, CD41, and CD61. In embodiments, the present megakaryocyte-derived extracellular vesicles are characterized by a substantial expression and/or presence of one or more of CD54, CD18, CD43, CD11b, CD62P, CD41, CD61, CD21, CD51, and CLEC-2. In embodiments, the present megakaryocyte-derived extracellular vesicles are characterized by a substantial expression and/or presence of one or more of CD62P, CD41, and CD61. In some embodiments, the present megakaryocyte-derived extracellular vesicles are characterized by not expressing and/or comprising a substantial amount of DRAQ5. In some embodiments, the present megakaryocyte-derived extracellular vesicles are characterized by being substantially free of DRAQ5.

In embodiments, greater than about 50% of the megakaryocyte-derived extracellular vesicles comprise a lipid bilayer membrane comprising CD62P. In some embodiments, greater than about 40% of the megakaryocyte-derived extracellular vesicles comprise a lipid bilayer membrane comprising CD62P. In some embodiments, greater than about 60% of the megakaryocyte-derived extracellular vesicles comprise a lipid bilayer membrane comprising CD62P. In some embodiments, greater than about 70% of the megakaryocyte-derived extracellular vesicles comprise a lipid bilayer membrane comprising CD62P. In some embodiments, greater than about 80% of the megakaryocyte-derived extracellular vesicles comprise a lipid bilayer membrane comprising CD62P. In some embodiments, greater than about 90% of the megakaryocyte-derived extracellular vesicles comprise a lipid bilayer membrane comprising CD62P. In some embodiments, greater than about 95% of the megakaryocyte-derived extracellular vesicles comprise a lipid bilayer membrane comprising CD62P. In some embodiments, greater than about 99% of the megakaryocyte-derived extracellular vesicles comprise a lipid bilayer membrane comprising CD62P.

In embodiments, about 50% or less of the megakaryocyte-derived extracellular vesicles comprise a lipid bilayer membrane comprising CD62P. In some embodiments, about 40% or less of the megakaryocyte-derived extracellular vesicles comprise a lipid bilayer membrane comprising CD62P. In some embodiments, about 60% or less of the megakaryocyte-derived extracellular vesicles comprise a lipid bilayer membrane comprising CD62P. In some embodiments, about 70% or less of the megakaryocyte-derived extracellular vesicles comprise a lipid bilayer membrane comprising CD62P. In some embodiments, about 80% or less of the megakaryocyte-derived extracellular vesicles comprise a lipid bilayer membrane comprising CD62P. In some embodiments, about 90% or less of the megakaryocyte-derived extracellular vesicles comprise a lipid bilayer membrane comprising CD62P. In some embodiments, about 95% or less of the megakaryocyte-derived extracellular vesicles comprise a lipid bilayer membrane comprising CD62P. In some embodiments, about 99% or less of the megakaryocyte-derived extracellular vesicles comprise a lipid bilayer membrane comprising CD62P.

In some embodiments, less than about 50% of the megakaryocyte-derived extracellular vesicles comprise a lipid bilayer membrane comprising CD62P. In embodiments, less than about 40% of the megakaryocyte-derived extracellular vesicles comprise a lipid bilayer membrane comprising CD62P. In some embodiments, less than about 30% of the megakaryocyte-derived extracellular vesicles comprise a lipid bilayer membrane comprising CD62P. In some embodiments, less than about 25% of the megakaryocyte-derived extracellular vesicles comprise a lipid bilayer membrane comprising CD62P. In some embodiments, less than about 20% of the megakaryocyte-derived extracellular vesicles comprise a lipid bilayer membrane comprising CD62P. In some embodiments, less than about 15% of the megakaryocyte-derived extracellular vesicles comprise a lipid bilayer membrane comprising CD62P. In some embodiments, less than about 10% of the megakaryocyte-derived extracellular vesicles comprise a lipid bilayer membrane comprising CD62P. In some embodiments, less than about 5% of the megakaryocyte-derived extracellular vesicles comprise a lipid bilayer membrane comprising CD62P. In some embodiments, less than about 1% of the megakaryocyte-derived extracellular vesicles comprise a lipid bilayer membrane comprising CD62P.

In some embodiments, between about 1% to about 99% of the megakaryocyte-derived extracellular vesicles comprise a lipid bilayer membrane comprising CD62P. In some embodiments, between about 1% to about 50% of the megakaryocyte-derived extracellular vesicles comprise a lipid bilayer membrane comprising CD62P. In some embodiments, between about 1% to about 25% of the megakaryocyte-derived extracellular vesicles comprise a lipid bilayer membrane comprising CD62P. In some embodiments, between about 1% to about 10% of the megakaryocyte-derived extracellular vesicles comprise a lipid bilayer membrane comprising CD62P. In some embodiments, between about 1% to about 5% of the megakaryocyte-derived extracellular vesicles comprise a lipid bilayer membrane comprising CD62P. In some embodiments, between about 1% to about 2% of the megakaryocyte-derived extracellular vesicles comprise a lipid bilayer membrane comprising CD62P. In some embodiments, between about 50% to about 99% of the megakaryocyte-derived extracellular vesicles comprise a lipid bilayer membrane comprising CD62P. In some embodiments, between about 75% to about 99% of the megakaryocyte-derived extracellular vesicles comprise a lipid bilayer membrane comprising CD62P. In some embodiments, between about 90% to about 99% of the megakaryocyte-derived extracellular vesicles comprise a lipid bilayer membrane comprising CD62P. In some embodiments, between about 95% to about 99% of the megakaryocyte-derived extracellular vesicles comprise a lipid bilayer membrane comprising CD62P.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD62P.

In embodiments, the megakaryocyte-derived extracellular vesicles are free of, or substantially free of CD62P.

In embodiments, the megakaryocyte-derived extracellular vesicles are characterized by a higher expression and/or presence of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 4-fold to about a 32-fold or about an 8-fold to about a 16-fold lower amount of CD62P than platelet free plasma (PFP) MkEVs. In embodiments, the megakaryocyte-derived extracellular vesicles have about a 15-fold or about a 16-fold lower amount of CD62P than platelet free plasma (PFP) MkEVs. In embodiments, the megakaryocyte-derived extracellular vesicles have about a 32-fold to about a 128-fold, about a 50-fold to about a 75-fold, or about a 60-fold to about a 70-fold lower amount of CD62P than platelet derived extracellular vesicles (PLT EVs). In embodiments, the megakaryocyte-derived extracellular vesicles have about a 60-fold, about a 64-fold, or about a 70-fold lower amount of CD62P than platelet derived extracellular vesicles (PLT EVs).

In embodiments, greater than about 50% of the megakaryocyte-derived extracellular vesicles comprise a lipid bilayer membrane comprising CD41. In some embodiments, greater than about 40% of the megakaryocyte-derived extracellular vesicles comprise a lipid bilayer membrane comprising CD41. In some embodiments, greater than about 60% of the megakaryocyte-derived extracellular vesicles comprise a lipid bilayer membrane comprising CD41. In some embodiments, greater than about 70% of the megakaryocyte-derived extracellular vesicles comprise a lipid bilayer membrane comprising CD41. In some embodiments, greater than about 80% of the megakaryocyte-derived extracellular vesicles comprise a lipid bilayer membrane comprising CD41. In some embodiments, greater than about 90% of the megakaryocyte-derived extracellular vesicles comprise a lipid bilayer membrane comprising CD41. In some embodiments, greater than about 95% of the megakaryocyte-derived extracellular vesicles comprise a lipid bilayer membrane comprising CD41. In some embodiments, greater than about 99% of the megakaryocyte-derived extracellular vesicles comprise a lipid bilayer membrane comprising CD41.

In embodiments, about 50% or less of the megakaryocyte-derived extracellular vesicles comprise a lipid bilayer membrane comprising CD41. In some embodiments, about 40% or less of the megakaryocyte-derived extracellular vesicles comprise a lipid bilayer membrane comprising CD41. In some embodiments, about 60% or less of the megakaryocyte-derived extracellular vesicles comprise a lipid bilayer membrane comprising CD41. In some embodiments, about 70% or less of the megakaryocyte-derived extracellular vesicles comprise a lipid bilayer membrane comprising CD41. In some embodiments, about 80% or less of the megakaryocyte-derived extracellular vesicles comprise a lipid bilayer membrane comprising CD41. In some embodiments, about 90% or less of the megakaryocyte-derived extracellular vesicles comprise a lipid bilayer membrane comprising CD41. In some embodiments, about 95% or less of the megakaryocyte-derived extracellular vesicles comprise a lipid bilayer membrane comprising CD41. In some embodiments, about 99% or less of the megakaryocyte-derived extracellular vesicles comprise a lipid bilayer membrane comprising CD41.

In some embodiments, less than about 50% of the megakaryocyte-derived extracellular vesicles comprise a lipid bilayer membrane comprising CD41. In embodiments, less than about 40% of the megakaryocyte-derived extracellular vesicles comprise a lipid bilayer membrane comprising CD41. In some embodiments, less than about 30% of the megakaryocyte-derived extracellular vesicles comprise a lipid bilayer membrane comprising CD41. In some embodiments, less than about 25% of the megakaryocyte-derived extracellular vesicles comprise a lipid bilayer membrane comprising CD41. In some embodiments, less than about 20% of the megakaryocyte-derived extracellular vesicles comprise a lipid bilayer membrane comprising CD41. In some embodiments, less than about 15% of the megakaryocyte-derived extracellular vesicles comprise a lipid bilayer membrane comprising CD41. In some embodiments, less than about 10% of the megakaryocyte-derived extracellular vesicles comprise a lipid bilayer membrane comprising CD41. In some embodiments, less than about 5% of the megakaryocyte-derived extracellular vesicles comprise a lipid bilayer membrane comprising CD41. In some embodiments, less than about 1% of the megakaryocyte-derived extracellular vesicles comprise a lipid bilayer membrane comprising CD41.

In some embodiments, between about 1% to about 99% of the megakaryocyte-derived extracellular vesicles comprise a lipid bilayer membrane comprising CD41. In some embodiments, between about 1% to about 50% of the megakaryocyte-derived extracellular vesicles comprise a lipid bilayer membrane comprising CD41. In some embodiments, between about 1% to about 25% of the megakaryocyte-derived extracellular vesicles comprise a lipid bilayer membrane comprising CD41. In some embodiments, between about 1% to about 10% of the megakaryocyte-derived extracellular vesicles comprise a lipid bilayer membrane comprising CD41. In some embodiments, between about 1% to about 5% of the megakaryocyte-derived extracellular vesicles comprise a lipid bilayer membrane comprising CD41. In some embodiments, between about 1% to about 2% of the megakaryocyte-derived extracellular vesicles comprise a lipid bilayer membrane comprising CD41. In some embodiments, between about 50% to about 99% of the megakaryocyte-derived extracellular vesicles comprise a lipid bilayer membrane comprising CD41. In some embodiments, between about 75% to about 99% of the megakaryocyte-derived extracellular vesicles comprise a lipid bilayer membrane comprising CD41. In some embodiments, between about 90% to about 99% of the megakaryocyte-derived extracellular vesicles comprise a lipid bilayer membrane comprising CD41. In some embodiments, between about 95% to about 99% of the megakaryocyte-derived extracellular vesicles comprise a lipid bilayer membrane comprising CD41.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD41.

In embodiments, the megakaryocyte-derived extracellular vesicles comprise CD41.

In embodiments, the megakaryocyte-derived extracellular vesicles are characterized by a higher expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD41/CD61 than platelet free plasma (PFP) MkEVs. In embodiments, the megakaryocyte-derived extracellular vesicles have about a 2-fold, about a 3-fold, or about a 4-fold greater amount of CD41/CD61 than platelet free plasma (PFP) MkEVs. In embodiments, the megakaryocyte-derived extracellular vesicles have about a 1.1-fold to about a 2-fold greater amount of CD41/CD61 than platelet derived extracellular vesicles (PLT EVs). In embodiments, the megakaryocyte-derived extracellular vesicles have about a 1.1-fold or about a 1.2-fold greater amount of CD41/CD61 than platelet derived extracellular vesicles (PLT EVs). In embodiments, the megakaryocyte-derived extracellular vesicles have an amount of CD41/CD61 that is substantially the same as platelet derived extracellular vesicles (PLT EVs).

In embodiments, greater than about 50% of the megakaryocyte-derived extracellular vesicles comprise a lipid bilayer membrane comprising CD61. In some embodiments, greater than about 40% of the megakaryocyte-derived extracellular vesicles comprise a lipid bilayer membrane comprising CD61. In some embodiments, greater than about 60% of the megakaryocyte-derived extracellular vesicles comprise a lipid bilayer membrane comprising CD61. In some embodiments, greater than about 70% of the megakaryocyte-derived extracellular vesicles comprise a lipid bilayer membrane comprising CD61. In some embodiments, greater than about 80% of the megakaryocyte-derived extracellular vesicles comprise a lipid bilayer membrane comprising CD61. In some embodiments, greater than about 90% of the megakaryocyte-derived extracellular vesicles comprise a lipid bilayer membrane comprising CD61. In some embodiments, greater than about 95% of the megakaryocyte-derived extracellular vesicles comprise a lipid bilayer membrane comprising CD61. In some embodiments, greater than about 99% of the megakaryocyte-derived extracellular vesicles comprise a lipid bilayer membrane comprising CD61.

In embodiments, about 50% or less of the megakaryocyte-derived extracellular vesicles comprise a lipid bilayer membrane comprising CD61. In some embodiments, less than about 40% of the megakaryocyte-derived extracellular vesicles comprise a lipid bilayer membrane comprising CD61. In some embodiments, about 60% or less of the megakaryocyte-derived extracellular vesicles comprise a lipid bilayer membrane comprising CD61. In some embodiments, about 70% or less of the megakaryocyte-derived extracellular vesicles comprise a lipid bilayer membrane comprising CD61. In some embodiments, about 80% or less of the megakaryocyte-derived extracellular vesicles comprise a lipid bilayer membrane comprising CD61. In some embodiments, less than about 90% of the megakaryocyte-derived extracellular vesicles comprise a lipid bilayer membrane comprising CD61. In some embodiments, about 95% or less of the megakaryocyte-derived extracellular vesicles comprise a lipid bilayer membrane comprising CD61. In some embodiments, about 99% or less of the megakaryocyte-derived extracellular vesicles comprise a lipid bilayer membrane comprising CD61.

In some embodiments, less than about 50% of the megakaryocyte-derived extracellular vesicles comprise a lipid bilayer membrane comprising CD61. In embodiments, less than about 40% of the megakaryocyte-derived extracellular vesicles comprise a lipid bilayer membrane comprising CD61. In some embodiments, less than about 30% of the megakaryocyte-derived extracellular vesicles comprise a lipid bilayer membrane comprising CD61. In some embodiments, less than about 25% of the megakaryocyte-derived extracellular vesicles comprise a lipid bilayer membrane comprising CD61. In some embodiments, less than about 20% of the megakaryocyte-derived extracellular vesicles comprise a lipid bilayer membrane comprising CD61. In some embodiments, less than about 15% of the megakaryocyte-derived extracellular vesicles comprise a lipid bilayer membrane comprising CD61. In some embodiments, less than about 10% of the megakaryocyte-derived extracellular vesicles comprise a lipid bilayer membrane comprising CD61. In some embodiments, less than about 5% of the megakaryocyte-derived extracellular vesicles comprise a lipid bilayer membrane comprising CD61. In some embodiments, less than about 1% of the megakaryocyte-derived extracellular vesicles comprise a lipid bilayer membrane comprising CD61.

In some embodiments, between about 1% to about 99% of the megakaryocyte-derived extracellular vesicles comprise a lipid bilayer membrane comprising CD61. In some embodiments, between about 1% to about 50% of the megakaryocyte-derived extracellular vesicles comprise a lipid bilayer membrane comprising CD61. In some embodiments, between about 1% to about 25% of the megakaryocyte-derived extracellular vesicles comprise a lipid bilayer membrane comprising CD61. In some embodiments, between about 1% to about 10% of the megakaryocyte-derived extracellular vesicles comprise a lipid bilayer membrane comprising CD61. In some embodiments, between about 1% to about 5% of the megakaryocyte-derived extracellular vesicles comprise a lipid bilayer membrane comprising CD61. In some embodiments, between about 1% to about 2% of the megakaryocyte-derived extracellular vesicles comprise a lipid bilayer membrane comprising CD61. In some embodiments, between about 50% to about 99% of the megakaryocyte-derived extracellular vesicles comprise a lipid bilayer membrane comprising CD61. In some embodiments, between about 75% to about 99% of the megakaryocyte-derived extracellular vesicles comprise a lipid bilayer membrane comprising CD61. In some embodiments, between about 90% to about 99% of the megakaryocyte-derived extracellular vesicles comprise a lipid bilayer membrane comprising CD61. In some embodiments, between about 95% to about 99% of the megakaryocyte-derived extracellular vesicles comprise a lipid bilayer membrane comprising CD61.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD61.

In embodiments, the megakaryocyte-derived extracellular vesicles are characterized by a higher expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD61 than platelet free plasma (PFP) MkEVs. In embodiments, the megakaryocyte-derived extracellular vesicles have about a 2-fold, about a 3-fold, or about a 4-fold greater amount of CD61 than platelet free plasma (PFP) MkEVs. In embodiments, the megakaryocyte-derived extracellular vesicles have about a 1.1-fold to about a 2-fold lower amount of CD61 than platelet derived extracellular vesicles (PLT EVs). In embodiments, the megakaryocyte-derived extracellular vesicles have about a 1.1-fold or about a 1.2-fold lower amount of CD61 than platelet derived extracellular vesicles (PLT EVs). In embodiments, the megakaryocyte-derived extracellular vesicles have an amount of CD61 that is substantially the same as platelet derived extracellular vesicles (PLT EVs).

In embodiments, greater than about 50% of the megakaryocyte-derived extracellular vesicles comprise a lipid bilayer membrane comprising CD54. In some embodiments, greater than about 40% of the megakaryocyte-derived extracellular vesicles comprise a lipid bilayer membrane comprising CD54. In some embodiments, greater than about 60% of the megakaryocyte-derived extracellular vesicles comprise a lipid bilayer membrane comprising CD54. In some embodiments, greater than about 70% of the megakaryocyte-derived extracellular vesicles comprise a lipid bilayer membrane comprising CD4. In some embodiments, greater than about 80% of the megakaryocyte-derived extracellular vesicles comprise a lipid bilayer membrane comprising CD54. In some embodiments, greater than about 90% of the megakaryocyte-derived extracellular vesicles comprise a lipid bilayer membrane comprising CD54. In some embodiments, greater than about 95% of the megakaryocyte-derived extracellular vesicles comprise a lipid bilayer membrane comprising CD54. In some embodiments, greater than about 99% of the megakaryocyte-derived extracellular vesicles comprise a lipid bilayer membrane comprising CD54.

In embodiments, about 50% or less of the megakaryocyte-derived extracellular vesicles comprise a lipid bilayer membrane comprising CD54. In some embodiments, about 40% or less of the megakaryocyte-derived extracellular vesicles comprise a lipid bilayer membrane comprising CD54. In some embodiments, about 60% or less of the megakaryocyte-derived extracellular vesicles comprise a lipid bilayer membrane comprising CD54. In some embodiments, about 70% or less of the megakaryocyte-derived extracellular vesicles comprise a lipid bilayer membrane comprising CD54. In some embodiments, about 80% or less of the megakaryocyte-derived extracellular vesicles comprise a lipid bilayer membrane comprising CD54. In some embodiments, about 90% or less of the megakaryocyte-derived extracellular vesicles comprise a lipid bilayer membrane comprising CD54. In some embodiments, about 95% or less of the megakaryocyte-derived extracellular vesicles comprise a lipid bilayer membrane comprising CD54. In some embodiments, about 99% or less of the megakaryocyte-derived extracellular vesicles comprise a lipid bilayer membrane comprising CD54.

In some embodiments, less than about 50% of the megakaryocyte-derived extracellular vesicles comprise a lipid bilayer membrane comprising CD54. In embodiments, less than about 40% of the megakaryocyte-derived extracellular vesicles comprise a lipid bilayer membrane comprising CD54. In some embodiments, less than about 30% of the megakaryocyte-derived extracellular vesicles comprise a lipid bilayer membrane comprising CD54. In some embodiments, less than about 25% of the megakaryocyte-derived extracellular vesicles comprise a lipid bilayer membrane comprising CD54. In some embodiments, less than about 20% of the megakaryocyte-derived extracellular vesicles comprise a lipid bilayer membrane comprising CD54. In some embodiments, less than about 15% of the megakaryocyte-derived extracellular vesicles comprise a lipid bilayer membrane comprising CD54. In some embodiments, less than about 10% of the megakaryocyte-derived extracellular vesicles comprise a lipid bilayer membrane comprising CD54. In some embodiments, less than about 5% of the megakaryocyte-derived extracellular vesicles comprise a lipid bilayer membrane comprising CD54. In some embodiments, less than about 1% of the megakaryocyte-derived extracellular vesicles comprise a lipid bilayer membrane comprising CD54.

In some embodiments, between about 1% to about 99% of the megakaryocyte-derived extracellular vesicles comprise a lipid bilayer membrane comprising CD54. In some embodiments, between about 1% to about 50% of the megakaryocyte-derived extracellular vesicles comprise a lipid bilayer membrane comprising CD54. In some embodiments, between about 1% to about 25% of the megakaryocyte-derived extracellular vesicles comprise a lipid bilayer membrane comprising CD54. In some embodiments, between about 1% to about 10% of the megakaryocyte-derived extracellular vesicles comprise a lipid bilayer membrane comprising CD54. In some embodiments, between about 1% to about 5% of the megakaryocyte-derived extracellular vesicles comprise a lipid bilayer membrane comprising CD54. In some embodiments, between about 1% to about 2% of the megakaryocyte-derived extracellular vesicles comprise a lipid bilayer membrane comprising CD54. In some embodiments, between about 50% to about 99% of the megakaryocyte-derived extracellular vesicles comprise a lipid bilayer membrane comprising CD54. In some embodiments, between about 75% to about 99% of the megakaryocyte-derived extracellular vesicles comprise a lipid bilayer membrane comprising CD54. In some embodiments, between about 90% to about 99% of the megakaryocyte-derived extracellular vesicles comprise a lipid bilayer membrane comprising CD54. In some embodiments, between about 95% to about 99% of the megakaryocyte-derived extracellular vesicles comprise a lipid bilayer membrane comprising CD54.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD54.

In embodiments, the megakaryocyte-derived extracellular vesicles are characterized by a higher expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold or about a 2-fold to about a 4-fold greater amount of CD54 than platelet free plasma (PFP) MkEVs. In embodiments, the megakaryocyte-derived extracellular vesicles have about a 3-fold greater amount of CD54 than platelet free plasma (PFP) MkEVs. In embodiments, the megakaryocyte-derived extracellular vesicles have about a 1.1-fold to about a 4-fold or about a 1.1-fold to about a 2-fold greater amount of CD54 than platelet derived extracellular vesicles (PLT EVs). In embodiments, the megakaryocyte-derived extracellular vesicles have about a 1.5-fold greater amount of CD54 than platelet derived extracellular vesicles (PLT EVs).

In embodiments, the megakaryocyte-derived extracellular vesicles are characterized by a lower expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD18. In some embodiments, greater than about 40% of the megakaryocyte-derived extracellular vesicles comprise a lipid bilayer membrane comprising CD18. In some embodiments, greater than about 60% of the megakaryocyte-derived extracellular vesicles comprise a lipid bilayer membrane comprising CD18. In some embodiments, greater than about 70% of the megakaryocyte-derived extracellular vesicles comprise a lipid bilayer membrane comprising CD18. In some embodiments, greater than about 80% of the megakaryocyte-derived extracellular vesicles comprise a lipid bilayer membrane comprising CD18. In some embodiments, greater than about 90% of the megakaryocyte-derived extracellular vesicles comprise a lipid bilayer membrane comprising CD18. In some embodiments, greater than about 95% of the megakaryocyte-derived extracellular vesicles comprise a lipid bilayer membrane comprising CD18. In some embodiments, greater than about 99% of the megakaryocyte-derived extracellular vesicles comprise a lipid bilayer membrane comprising CD18.

In embodiments, about 50% or less of the megakaryocyte-derived extracellular vesicles comprise a lipid bilayer membrane comprising CD18. In some embodiments, about 40% or less of the megakaryocyte-derived extracellular vesicles comprise a lipid bilayer membrane comprising CD18. In some embodiments, about 60% or less of the megakaryocyte-derived extracellular vesicles comprise a lipid bilayer membrane comprising CD18. In some embodiments, about 70% or less of the megakaryocyte-derived extracellular vesicles comprise a lipid bilayer membrane comprising CD18. In some embodiments, about 80% or less of the megakaryocyte-derived extracellular vesicles comprise a lipid bilayer membrane comprising CD18. In some embodiments, about 90% or less of the megakaryocyte-derived extracellular vesicles comprise a lipid bilayer membrane comprising CD18. In some embodiments, about 95% or less of the megakaryocyte-derived extracellular vesicles comprise a lipid bilayer membrane comprising CD18. In some embodiments, about 99% or less of the megakaryocyte-derived extracellular vesicles comprise a lipid bilayer membrane comprising CD18.

In some embodiments, less than about 50% of the megakaryocyte-derived extracellular vesicles comprise a lipid bilayer membrane comprising CD18. In embodiments, less than about 40% of the megakaryocyte-derived extracellular vesicles comprise a lipid bilayer membrane comprising CD18. In some embodiments, less than about 30% of the megakaryocyte-derived extracellular vesicles comprise a lipid bilayer membrane comprising CD18. In some embodiments, less than about 25% of the megakaryocyte-derived extracellular vesicles comprise a lipid bilayer membrane comprising CD18. In some embodiments, less than about 20% of the megakaryocyte-derived extracellular vesicles comprise a lipid bilayer membrane comprising CD18. In some embodiments, less than about 15% of the megakaryocyte-derived extracellular vesicles comprise a lipid bilayer membrane comprising CD18. In some embodiments, less than about 10% of the megakaryocyte-derived extracellular vesicles comprise a lipid bilayer membrane comprising CD18. In some embodiments, less than about 5% of the megakaryocyte-derived extracellular vesicles comprise a lipid bilayer membrane comprising CD18. In some embodiments, less than about 1% of the megakaryocyte-derived extracellular vesicles comprise a lipid bilayer membrane comprising CD18.

In some embodiments, between about 1% to about 99% of the megakaryocyte-derived extracellular vesicles comprise a lipid bilayer membrane comprising CD18. In some embodiments, between about 1% to about 50% of the megakaryocyte-derived extracellular vesicles comprise a lipid bilayer membrane comprising CD18. In some embodiments, between about 1% to about 25% of the megakaryocyte-derived extracellular vesicles comprise a lipid bilayer membrane comprising CD18. In some embodiments, between about 1% to about 10% of the megakaryocyte-derived extracellular vesicles comprise a lipid bilayer membrane comprising CD18. In some embodiments, between about 1% to about 5% of the megakaryocyte-derived extracellular vesicles comprise a lipid bilayer membrane comprising CD18. In some embodiments, between about 1% to about 2% of the megakaryocyte-derived extracellular vesicles comprise a lipid bilayer membrane comprising CD18. In some embodiments, between about 50% to about 99% of the megakaryocyte-derived extracellular vesicles comprise a lipid bilayer membrane comprising CD18. In some embodiments, between about 75% to about 99% of the megakaryocyte-derived extracellular vesicles comprise a lipid bilayer membrane comprising CD18. In some embodiments, between about 90% to about 99% of the megakaryocyte-derived extracellular vesicles comprise a lipid bilayer membrane comprising CD18. In some embodiments, between about 95% to about 99% of the megakaryocyte-derived extracellular vesicles comprise a lipid bilayer membrane comprising CD18.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD18.

In embodiments, the megakaryocyte-derived extracellular vesicles are characterized by a higher expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold, an 8-fold to about a 64-fold, or about a 16-fold to about a 32-fold, or about a 16-fold to about a 24-fold greater amount of CD18 than platelet free plasma (PFP) MkEVs. In embodiments, the megakaryocyte-derived extracellular vesicles have about a 20-fold greater amount of CD18 than platelet free plasma (PFP) MkEVs. In embodiments, the megakaryocyte-derived extracellular vesicles have about a 1.1-fold to about a 4-fold or about a 1.1-fold to about a 2-fold greater amount of CD18 than platelet derived extracellular vesicles (PLT EVs). In embodiments, the megakaryocyte-derived extracellular vesicles have about a 1.5-fold greater amount of CD18 than platelet derived extracellular vesicles (PLT EVs).

In embodiments, the megakaryocyte-derived extracellular vesicles are characterized by a lower expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the mega-karyocyte-derived extracellular vesicles comprise a lipid bilayer membrane comprising CD43. In some embodiments, greater than about 40% of the megakaryocyte-derived extra-cellular vesicles comprise a lipid bilayer membrane com-prising CD43. In some embodiments, greater than about 60% of the megakaryocyte-derived extracellular vesicles comprise a lipid bilayer membrane comprising CD43. In some embodiments, greater than about 70% of the mega-karyocyte-derived extracellular vesicles comprise a lipid bilayer membrane comprising CD43. In some embodiments, greater than about 80% of the megakaryocyte-derived extra-cellular vesicles comprise a lipid bilayer membrane com-prising CD43. In some embodiments, greater than about 90% of the megakaryocyte-derived extracellular vesicles comprise a lipid bilayer membrane comprising CD43. In some embodiments, greater than about 95% of the mega-karyocyte-derived extracellular vesicles comprise a lipid bilayer membrane comprising CD43. In some embodiments, greater than about 99% of the megakaryocyte-derived extra-cellular vesicles comprise a lipid bilayer membrane com-prising CD43.

In embodiments, about 50% or less of the megakaryocyte-derived extracellular vesicles comprise a lipid bilayer mem-brane comprising CD43. In some embodiments, about 40% or less of the megakaryocyte-derived extracellular vesicles comprise a lipid bilayer membrane comprising CD43. In some embodiments, about 60% or less of the megakaryo-cyte-derived extracellular vesicles comprise a lipid bilayer membrane comprising CD43. In some embodiments, about 70% or less of the megakaryocyte-derived extracellular vesicles comprise a lipid bilayer membrane comprising CD43. In some embodiments, about 80% or less of the megakaryocyte-derived extracellular vesicles comprise a lipid bilayer membrane comprising CD43. In some embodi-ments, about 90% or less of the megakaryocyte-derived extracellular vesicles comprise a lipid bilayer membrane comprising CD43. In some embodiments, about 95% or less of the megakaryocyte-derived extracellular vesicles com-prise a lipid bilayer membrane comprising CD43. In some embodiments, about 99% or less of the megakaryocyte-derived extracellular vesicles comprise a lipid bilayer mem-brane comprising CD43.

In some embodiments, less than about 50% of the mega-karyocyte-derived extracellular vesicles comprise a lipid bilayer membrane comprising CD43. In embodiments, less than about 40% of the megakaryocyte-derived extracellular vesicles comprise a lipid bilayer membrane comprising CD43. In some embodiments, less than about 30% of the megakaryocyte-derived extracellular vesicles comprise a lipid bilayer membrane comprising CD43. In some embodi-ments, less than about 25% of the megakaryocyte-derived extracellular vesicles comprise a lipid bilayer membrane comprising CD43. In some embodiments, less than about 20% of the megakaryocyte-derived extracellular vesicles comprise a lipid bilayer membrane comprising CD43. In some embodiments, less than about 15% of the megakaryo-cyte-derived extracellular vesicles comprise a lipid bilayer membrane comprising CD43. In some embodiments, less than about 10% of the megakaryocyte-derived extracellular vesicles comprise a lipid bilayer membrane comprising CD43. In some embodiments, less than about 5% of the megakaryocyte-derived extracellular vesicles comprise a lipid bilayer membrane comprising CD43. In some embodi-ments, less than about 1% of the megakaryocyte-derived extracellular vesicles comprise a lipid bilayer membrane comprising CD43.

In some embodiments, between about 1% to about 99% of the megakaryocyte-derived extracellular vesicles comprise a lipid bilayer membrane comprising CD43. In some embodi-ments, between about 1% to about 50% of the megakaryo-cyte-derived extracellular vesicles comprise a lipid bilayer membrane comprising CD43. In some embodiments, between about 1% to about 25% of the megakaryocyte-derived extracellular vesicles comprise a lipid bilayer mem-brane comprising CD43. In some embodiments, between about 1% to about 10% of the megakaryocyte-derived extracellular vesicles comprise a lipid bilayer membrane comprising CD43. In some embodiments, between about 1% to about 5% of the megakaryocyte-derived extracellular vesicles comprise a lipid bilayer membrane comprising CD43. In some embodiments, between about 1% to about 2% of the megakaryocyte-derived extracellular vesicles comprise a lipid bilayer membrane comprising CD43. In some embodiments, between about 50% to about 99% of the megakaryocyte-derived extracellular vesicles comprise a lipid bilayer membrane comprising CD43. In some embodi-ments, between about 75% to about 99% of the megakaryo-cyte-derived extracellular vesicles comprise a lipid bilayer membrane comprising CD43. In some embodiments, between about 90% to about 99% of the megakaryocyte-derived extracellular vesicles comprise a lipid bilayer mem-brane comprising CD43. In some embodiments, between about 95% to about 99% of the megakaryocyte-derived extracellular vesicles comprise a lipid bilayer membrane comprising CD43.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD43.

In embodiments, the megakaryocyte-derived extracellular vesicles are characterized by a higher expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 4-fold to about a 64-fold, or about a 8-fold to about a 32-fold, or about a 8-fold to about a 16-fold greater amount of CD43 than platelet free plasma (PFP) MkEVs. In embodiments, the megakaryocyte-derived extracellular vesicles have about a 10-fold or about a 12-fold greater amount of CD43 than platelet free plasma (PFP) MkEVs. In embodiments, the megakaryocyte-derived extracellular vesicles have about a 1.5-fold to about an 8-fold or about a 2-fold to about a 4-fold greater amount of CD43 than platelet derived extracellular vesicles (PLT EVs). In embodiments, the megakaryocyte-derived extracellular vesicles have about a 3-fold or about a 4-fold greater amount of CD43 than platelet derived extracellular vesicles (PLT EVs).

In embodiments, the megakaryocyte-derived extracellular vesicles are characterized by a lower expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD11b. In some embodiments, greater than about 40% of the megakaryocyte-derived extracellular vesicles comprise a lipid bilayer membrane comprising CD11b. In some embodiments, greater than about 60% of the megakaryocyte-derived extracellular vesicles comprise a lipid bilayer membrane comprising CD11 b. In some embodiments, greater than about 70% of the megakaryocyte-derived extracellular vesicles comprise a lipid bilayer membrane comprising CD11b. In some embodiments, greater than about 80% of the megakaryocyte-derived extracellular vesicles comprise a lipid bilayer membrane comprising CD11 b. In some embodiments, greater than about 90% of the megakaryocyte-derived extracellular vesicles comprise a lipid bilayer membrane comprising CD11 b. In some embodiments, greater than about 95% of the megakaryocyte-derived extracellular vesicles comprise a lipid bilayer membrane comprising CD11 b. In some embodiments, greater than about 99% of the megakaryocyte-derived extracellular vesicles comprise a lipid bilayer membrane comprising CD11 b.

In embodiments, about 50% or less of the megakaryocyte-derived extracellular vesicles comprise a lipid bilayer membrane comprising CD11 b. In some embodiments, about 40% or less of the megakaryocyte-derived extracellular vesicles comprise a lipid bilayer membrane comprising CD11b. In some embodiments, about 60% or less of the megakaryocyte-derived extracellular vesicles comprise a lipid bilayer membrane comprising CD11 b. In some embodiments, about 70% or less of the megakaryocyte-derived extracellular vesicles comprise a lipid bilayer membrane comprising CD11b. In some embodiments, about 80% or less of the megakaryocyte-derived extracellular vesicles comprise a lipid bilayer membrane comprising CD11 b. In some embodiments, about 90% or less of the megakaryocyte-derived extracellular vesicles comprise a lipid bilayer membrane comprising CD11b. In some embodiments, about 95% or less of the megakaryocyte-derived extracellular vesicles comprise a lipid bilayer membrane comprising CD11 b. In some embodiments, about 99% or less of the megakaryocyte-derived extracellular vesicles comprise a lipid bilayer membrane comprising CD11 b.

In some embodiments, less than about 50% of the megakaryocyte-derived extracellular vesicles comprise a lipid bilayer membrane comprising CD11 b. In embodiments, less than about 40% of the megakaryocyte-derived extracellular vesicles comprise a lipid bilayer membrane comprising CD11 b. In some embodiments, less than about 30% of the megakaryocyte-derived extracellular vesicles comprise a lipid bilayer membrane comprising CD11 b. In some embodiments, less than about 25% of the megakaryocyte-derived extracellular vesicles comprise a lipid bilayer membrane comprising CD11 b. In some embodiments, less than about 20% of the megakaryocyte-derived extracellular vesicles comprise a lipid bilayer membrane comprising CD11b. In some embodiments, less than about 15% of the megakaryocyte-derived extracellular vesicles comprise a lipid bilayer membrane comprising CD11 b. In some embodiments, less than about 10% of the megakaryocyte-derived extracellular vesicles comprise a lipid bilayer membrane comprising CD11b. In some embodiments, less than about 5% of the megakaryocyte-derived extracellular vesicles comprise a lipid bilayer membrane comprising CD11 b. In some embodiments, less than about 1% of the megakaryocyte-derived extracellular vesicles comprise a lipid bilayer membrane comprising CD11 b.

In some embodiments, between about 1% to about 99% of the megakaryocyte-derived extracellular vesicles comprise a lipid bilayer membrane comprising CD11 b. In some embodiments, between about 1% to about 50% of the megakaryocyte-derived extracellular vesicles comprise a lipid bilayer membrane comprising CD11 b. In some embodiments, between about 1% to about 25% of the megakaryocyte-derived extracellular vesicles comprise a lipid bilayer membrane comprising CD11b. In some embodiments, between about 1% to about 10% of the megakaryocyte-derived extracellular vesicles comprise a lipid bilayer membrane comprising CD11 b. In some embodiments, between about 1% to about 5% of the megakaryocyte-derived extracellular vesicles comprise a lipid bilayer membrane comprising CD11 b. In some embodiments, between about 1% to about 2% of the megakaryocyte-derived extracellular vesicles comprise a lipid bilayer membrane comprising CD11 b. In some embodiments, between about 50% to about 99% of the megakaryocyte-derived extracellular vesicles comprise a lipid bilayer membrane comprising CD11 b. In some embodiments, between about 75% to about 99% of the megakaryocyte-derived extracellular vesicles comprise a lipid bilayer membrane comprising CD11 b. In some embodiments, between about 90% to about 99% of the megakaryocyte-derived extracellular vesicles comprise a lipid bilayer membrane comprising CD11 b. In some embodiments, between about 95% to about 99% of the megakaryocyte-derived extracellular vesicles comprise a lipid bilayer membrane comprising CD11 b.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD11 b.

In embodiments, the megakaryocyte-derived extracellular vesicles are characterized by a higher expression and/or presence of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD11b than platelet free plasma (PFP) MkEVs. In embodiments, the megakaryocyte-derived extracellular vesicles have about a 3-fold greater amount of CD11b than platelet free plasma (PFP) MkEVs. In embodiments, the megakaryocyte-derived extracellular vesicles have about a 1.1-fold to about a 4-fold, or about a 1.1-fold to about a 2-fold greater amount of CD11b than platelet derived extracellular vesicles (PLT EVs). In embodiments, the megakaryocyte-derived extracellular vesicles have about a 1.5-fold greater amount of CD11b than platelet derived extracellular vesicles (PLT EVs).

In embodiments, the megakaryocyte-derived extracellular vesicles are characterized by a higher expression and/or presence of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD21. In some embodiments, greater than about 40% of the megakaryocyte-derived extracellular vesicles comprise a lipid bilayer membrane comprising CD21. In some embodiments, greater than about 60% of the megakaryocyte-derived extracellular vesicles comprise a lipid bilayer membrane comprising CD21. In some embodiments, greater than about 70% of the megakaryocyte-derived extracellular vesicles comprise a lipid bilayer membrane comprising CD21. In some embodiments, greater than about 80% of the megakaryocyte-derived extracellular vesicles comprise a lipid bilayer membrane comprising CD21. In some embodiments, greater than about 90% of the megakaryocyte-derived extracellular vesicles comprise a lipid bilayer membrane comprising CD21. In some embodiments, greater than about 95% of the megakaryocyte-derived extracellular vesicles comprise a lipid bilayer membrane comprising CD21. In some embodiments, greater than about 99% of the megakaryocyte-derived extracellular vesicles comprise a lipid bilayer membrane comprising CD21.

In embodiments, about 50% or less of the megakaryocyte-derived extracellular vesicles comprise a lipid bilayer membrane comprising CD21. In some embodiments, about 40% or less of the megakaryocyte-derived extracellular vesicles comprise a lipid bilayer membrane comprising CD21. In some embodiments, about 60% or less of the megakaryocyte-derived extracellular vesicles comprise a lipid bilayer membrane comprising CD21. In some embodiments, about 70% or less of the megakaryocyte-derived extracellular vesicles comprise a lipid bilayer membrane comprising CD21. In some embodiments, about 80% or less of the megakaryocyte-derived extracellular vesicles comprise a lipid bilayer membrane comprising CD21. In some embodiments, about 90% or less of the megakaryocyte-derived extracellular vesicles comprise a lipid bilayer membrane comprising CD21. In some embodiments, about 95% or less of the megakaryocyte-derived extracellular vesicles comprise a lipid bilayer membrane comprising CD21. In some embodiments, about 99% or less of the megakaryocyte-derived extracellular vesicles comprise a lipid bilayer membrane comprising CD21.

In some embodiments, less than about 50% of the megakaryocyte-derived extracellular vesicles comprise a lipid bilayer membrane comprising CD21. In embodiments, less than about 40% of the megakaryocyte-derived extracellular vesicles comprise a lipid bilayer membrane comprising CD21. In some embodiments, less than about 30% of the megakaryocyte-derived extracellular vesicles comprise a lipid bilayer membrane comprising CD21. In some embodiments, less than about 25% of the megakaryocyte-derived extracellular vesicles comprise a lipid bilayer membrane comprising CD21. In some embodiments, less than about 20% of the megakaryocyte-derived extracellular vesicles comprise a lipid bilayer membrane comprising CD21. In some embodiments, less than about 15% of the megakaryocyte-derived extracellular vesicles comprise a lipid bilayer membrane comprising CD21. In some embodiments, less than about 10% of the megakaryocyte-derived extracellular vesicles comprise a lipid bilayer membrane comprising CD21. In some embodiments, less than about 5% of the megakaryocyte-derived extracellular vesicles comprise a lipid bilayer membrane comprising CD21. In some embodiments, less than about 1% of the megakaryocyte-derived extracellular vesicles comprise a lipid bilayer membrane comprising CD21.

In some embodiments, between about 1% to about 99% of the megakaryocyte-derived extracellular vesicles comprise a lipid bilayer membrane comprising CD21. In some embodiments, between about 1% to about 50% of the megakaryocyte-derived extracellular vesicles comprise a lipid bilayer membrane comprising CD21. In some embodiments, between about 1% to about 25% of the megakaryocyte-derived extracellular vesicles comprise a lipid bilayer membrane comprising CD21. In some embodiments, between about 1% to about 10% of the megakaryocyte-derived extracellular vesicles comprise a lipid bilayer membrane comprising CD21. In some embodiments, between about 1% to about 5% of the megakaryocyte-derived extracellular vesicles comprise a lipid bilayer membrane comprising CD21. In some embodiments, between about 1% to about 2% of the megakaryocyte-derived extracellular vesicles comprise a lipid bilayer membrane comprising CD21. In some embodiments, between about 50% to about 99% of the megakaryocyte-derived extracellular vesicles comprise a lipid bilayer membrane comprising CD21. In some embodiments, between about 75% to about 99% of the megakaryocyte-derived extracellular vesicles comprise a lipid bilayer membrane comprising CD21. In some embodiments, between about 90% to about 99% of the megakaryocyte-derived extracellular vesicles comprise a lipid bilayer membrane comprising CD21. In some embodiments, between about 95% to about 99% of the megakaryocyte-derived extracellular vesicles comprise a lipid bilayer membrane comprising CD21.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD21.

In embodiments, the megakaryocyte-derived extracellular vesicles are characterized by a higher expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 64-fold, about a 4-fold to about a 32-fold, or about an 8-fold to about a 16-fold greater amount of CD21 than platelet free plasma (PFP) MkEVs. In embodiments, the megakaryocyte-derived extracellular vesicles have about a 10-fold or about a 12-fold greater amount of CD21 than platelet free plasma (PFP) MkEVs. In embodiments, the megakaryocyte-derived extracellular vesicles have about a 2-fold to about an 8-fold, or about a 4-fold to about an 8-fold greater amount of CD21 than platelet derived extracellular vesicles (PLT EVs). In embodiments, the megakaryocyte-derived extracellular vesicles have about a 4-fold or about a 5-fold greater amount of CD21 than platelet derived extracellular vesicles (PLT EVs).

In embodiments, the megakaryocyte-derived extracellular vesicles are characterized by a lower expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD51. In some embodiments, greater than about 40% of the megakaryocyte-derived extracellular vesicles comprise a lipid bilayer membrane comprising CD51. In some embodiments, greater than about 60% of the megakaryocyte-derived extracellular vesicles comprise a lipid bilayer membrane comprising CD51. In some embodiments, greater than about 70% of the megakaryocyte-derived extracellular vesicles comprise a lipid bilayer membrane comprising CD51. In some embodiments, greater than about 80% of the megakaryocyte-derived extracellular vesicles comprise a lipid bilayer membrane comprising CD51. In some embodiments, greater than about 90% of the megakaryocyte-derived extracellular vesicles comprise a lipid bilayer membrane comprising CD51. In some embodiments, greater than about 95% of the megakaryocyte-derived extracellular vesicles comprise a lipid bilayer membrane comprising CD51. In some embodiments, greater than about 99% of the megakaryocyte-derived extracellular vesicles comprise a lipid bilayer membrane comprising CD51.

In embodiments, about 50% or less of the megakaryocyte-derived extracellular vesicles comprise a lipid bilayer membrane comprising CD51. In some embodiments, about 40% or less of the megakaryocyte-derived extracellular vesicles comprise a lipid bilayer membrane comprising CD51. In some embodiments, about 60% or less of the megakaryocyte-derived extracellular vesicles comprise a lipid bilayer membrane comprising CD51. In some embodiments, about 70% or less of the megakaryocyte-derived extracellular vesicles comprise a lipid bilayer membrane comprising CD51. In some embodiments, about 80% or less of the megakaryocyte-derived extracellular vesicles comprise a lipid bilayer membrane comprising CD51. In some embodiments, about 90% or less of the megakaryocyte-derived extracellular vesicles comprise a lipid bilayer membrane comprising CD51. In some embodiments, about 95% or less of the megakaryocyte-derived extracellular vesicles comprise a lipid bilayer membrane comprising CD51. In some embodiments, about 99% or less of the megakaryocyte-derived extracellular vesicles comprise a lipid bilayer membrane comprising CD51.

In some embodiments, less than about 50% of the megakaryocyte-derived extracellular vesicles comprise a lipid bilayer membrane comprising CD51. In embodiments, less than about 40% of the megakaryocyte-derived extracellular vesicles comprise a lipid bilayer membrane comprising CD51. In some embodiments, less than about 30% of the megakaryocyte-derived extracellular vesicles comprise a lipid bilayer membrane comprising CD51. In some embodiments, less than about 25% of the megakaryocyte-derived extracellular vesicles comprise a lipid bilayer membrane comprising CD51. In some embodiments, less than about 20% of the megakaryocyte-derived extracellular vesicles comprise a lipid bilayer membrane comprising CD51. In some embodiments, less than about 15% of the megakaryocyte-derived extracellular vesicles comprise a lipid bilayer membrane comprising CD51. In some embodiments, less than about 10% of the megakaryocyte-derived extracellular vesicles comprise a lipid bilayer membrane comprising CD51. In some embodiments, less than about 5% of the megakaryocyte-derived extracellular vesicles comprise a lipid bilayer membrane comprising CD51. In some embodiments, less than about 1% of the megakaryocyte-derived extracellular vesicles comprise a lipid bilayer membrane comprising CD51.

In some embodiments, between about 1% to about 99% of the megakaryocyte-derived extracellular vesicles comprise a lipid bilayer membrane comprising CD51. In some embodiments, between about 1% to about 50% of the megakaryocyte-derived extracellular vesicles comprise a lipid bilayer membrane comprising CD51. In some embodiments, between about 1% to about 25% of the megakaryocyte-derived extracellular vesicles comprise a lipid bilayer membrane comprising CD51. In some embodiments, between about 1% to about 10% of the megakaryocyte-derived extracellular vesicles comprise a lipid bilayer membrane comprising CD51. In some embodiments, between about 1% to about 5% of the megakaryocyte-derived extracellular vesicles comprise a lipid bilayer membrane comprising CD51. In some embodiments, between about 1% to about 2% of the megakaryocyte-derived extracellular vesicles comprise a lipid bilayer membrane comprising CD51. In some embodiments, between about 50% to about 99% of the megakaryocyte-derived extracellular vesicles comprise a lipid bilayer membrane comprising CD51. In some embodiments, between about 75% to about 99% of the megakaryocyte-derived extracellular vesicles comprise a lipid bilayer membrane comprising CD51. In some embodiments, between about 90% to about 99% of the megakaryocyte-derived extracellular vesicles comprise a lipid bilayer membrane comprising CD51. In some embodiments, between about 95% to about 99% of the megakaryocyte-derived extracellular vesicles comprise a lipid bilayer membrane comprising CD51.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD51.

In embodiments, the megakaryocyte-derived extracellular vesicles are characterized by a higher expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD51 than platelet free plasma (PFP) MkEVs.

In embodiments, the megakaryocyte-derived extracellular vesicles have about a 1.5-fold lower amount of CD51 than platelet free plasma (PFP) MkEVs. In embodiments, the megakaryocyte-derived extracellular vesicles have about a 1.1-fold to about a 4-fold, or about a 1.1-fold to about a 2-fold lower amount of CD51 than platelet derived extracellular vesicles (PLT EVs). In embodiments, the megakaryocyte-derived extracellular vesicles have about a 1.5-fold lower amount of CD51 than platelet derived extracellular vesicles (PLT EVs).

In embodiments, greater than about 50% of the megakaryocyte-derived extracellular vesicles comprise a lipid bilayer membrane comprising CLEC-2. In some embodiments, greater than about 40% of the megakaryocyte-derived extracellular vesicles comprise a lipid bilayer membrane comprising CLEC-2. In some embodiments, greater than about 60% of the megakaryocyte-derived extracellular vesicles comprise a lipid bilayer membrane comprising CLEC-2. In some embodiments, greater than about 70% of the megakaryocyte-derived extracellular vesicles comprise a lipid bilayer membrane comprising CLEC-2. In some embodiments, greater than about 80% of the megakaryocyte-derived extracellular vesicles comprise a lipid bilayer membrane comprising CLEC-2. In some embodiments, greater than about 90% of the megakaryocyte-derived extracellular vesicles comprise a lipid bilayer membrane comprising CLEC-2. In some embodiments, greater than about 95% of the megakaryocyte-derived extracellular vesicles comprise a lipid bilayer membrane comprising CLEC-2. In some embodiments, greater than about 99% of the megakaryocyte-derived extracellular vesicles comprise a lipid bilayer membrane comprising CLEC-2.

In embodiments, about 50% or less of the megakaryocyte-derived extracellular vesicles comprise a lipid bilayer membrane comprising CLEC-2. In some embodiments, about 40% or less of the megakaryocyte-derived extracellular vesicles comprise a lipid bilayer membrane comprising CLEC-2. In some embodiments, about 60% or less of the megakaryocyte-derived extracellular vesicles comprise a lipid bilayer membrane comprising CLEC-2. In some embodiments, about 70% or less of the megakaryocyte-derived extracellular vesicles comprise a lipid bilayer membrane comprising CLEC-2. In some embodiments, about 80% or less of the megakaryocyte-derived extracellular vesicles comprise a lipid bilayer membrane comprising CLEC-2. In some embodiments, about 90% or less of the megakaryocyte-derived extracellular vesicles comprise a lipid bilayer membrane comprising CLEC-2. In some embodiments, about 95% or less of the megakaryocyte-derived extracellular vesicles comprise a lipid bilayer membrane comprising CLEC-2. In some embodiments, about 99% or less of the megakaryocyte-derived extracellular vesicles comprise a lipid bilayer membrane comprising CLEC-2.

In some embodiments, less than about 50% of the megakaryocyte-derived extracellular vesicles comprise a lipid bilayer membrane comprising CLEC-2. In embodiments, less than about 40% of the megakaryocyte-derived extracellular vesicles comprise a lipid bilayer membrane comprising CLEC-2. In some embodiments, less than about 30% of the megakaryocyte-derived extracellular vesicles comprise a lipid bilayer membrane comprising CLEC-2. In some embodiments, less than about 25% of the megakaryocyte-derived extracellular vesicles comprise a lipid bilayer membrane comprising CLEC-2. In some embodiments, less than about 20% of the megakaryocyte-derived extracellular vesicles comprise a lipid bilayer membrane comprising CLEC-2. In some embodiments, less than about 15% of the megakaryocyte-derived extracellular vesicles comprise a lipid bilayer membrane comprising CLEC-2. In some embodiments, less than about 10% of the megakaryocyte-derived extracellular vesicles comprise a lipid bilayer membrane comprising CLEC-2. In some embodiments, less than about 5% of the megakaryocyte-derived extracellular vesicles comprise a lipid bilayer membrane comprising CLEC-2. In some embodiments, less than about 1% of the megakaryocyte-derived extracellular vesicles comprise a lipid bilayer membrane comprising CLEC-2.

In some embodiments, between about 1% to about 99% of the megakaryocyte-derived extracellular vesicles comprise a lipid bilayer membrane comprising CLEC-2. In some embodiments, between about 1% to about 50% of the megakaryocyte-derived extracellular vesicles comprise a lipid bilayer membrane comprising CLEC-2. In some embodiments, between about 1% to about 25% of the megakaryocyte-derived extracellular vesicles comprise a lipid bilayer membrane comprising CLEC-2. In some embodiments, between about 1% to about 10% of the megakaryocyte-derived extracellular vesicles comprise a lipid bilayer membrane comprising CLEC-2. In some embodiments, between about 1% to about 5% of the megakaryocyte-derived extracellular vesicles comprise a lipid bilayer membrane comprising CLEC-2. In some embodiments, between about 1% to about 2% of the megakaryocyte-derived extracellular vesicles comprise a lipid bilayer membrane comprising CLEC-2. In some embodiments, between about 50% to about 99% of the megakaryocyte-derived extracellular vesicles comprise a lipid bilayer membrane comprising CLEC-2. In some embodiments, between about 75% to about 99% of the megakaryocyte-derived extracellular vesicles comprise a lipid bilayer membrane comprising CLEC-2. In some embodiments, between about 90% to about 99% of the megakaryocyte-derived extracellular vesicles comprise a lipid bilayer membrane comprising CLEC-2. In some embodiments, between about 95% to about 99% of the megakaryocyte-derived extracellular vesicles comprise a lipid bilayer membrane comprising CLEC-2.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CLEC-2.

In embodiments, the megakaryocyte-derived extracellular vesicles are characterized by a higher expression and/or presence of CLEC-2 than naturally-occurring meg akaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 16-fold, or about a 4-fold to about an 8-fold lower amount of CLEC-2 than platelet free plasma (PFP) MkEVs. In embodiments, the megakaryocyte-derived extracellular vesicles have about a 4-fold or about a 5-fold lower amount of CLEC-2 than platelet free plasma (PFP) MkEVs. In embodiments, the megakaryocyte-derived extracellular vesicles have about a 4-fold to about a 32-fold, or about an 8-fold to about a 16-fold lower amount of CLEC-2 than platelet derived extracellular vesicles (PLT EVs). In embodiments, the megakaryocyte-derived extracellular vesicles have about a 10-fold or about a 12-fold lower amount of CLEC-2 than platelet derived extracellular vesicles (PLT EVs).

In embodiments, greater than about 50% of the megakaryocyte-derived extracellular vesicles comprise a lipid bilayer membrane comprising LAMP-1 (CD107A). In some embodiments, greater than about 40% of the megakaryocyte-derived extracellular vesicles comprise a lipid bilayer membrane comprising LAMP-1 (CD107A). In some embodiments, greater than about 60% of the megakaryocyte-derived extracellular vesicles comprise a lipid bilayer membrane comprising LAMP-1 (CD107A). In some embodiments, greater than about 70% of the megakaryocyte-derived extracellular vesicles comprise a lipid bilayer membrane comprising LAMP-1 (CD107A). In some embodiments, greater than about 80% of the megakaryocyte-derived extracellular vesicles comprise a lipid bilayer membrane comprising LAMP-1 (CD107A). In some embodiments, greater than about 90% of the megakaryocyte-derived extracellular vesicles comprise a lipid bilayer membrane comprising LAMP-1 (CD107A). In some embodiments, greater than about 95% of the megakaryocyte-derived extracellular vesicles comprise a lipid bilayer membrane comprising LAMP-1 (CD107A). In some embodiments, greater than about 99% of the megakaryocyte-derived extracellular vesicles comprise a lipid bilayer membrane comprising LAMP-1 (CD107A).

In embodiments, about 50% or less of the megakaryocyte-derived extracellular vesicles comprise a lipid bilayer membrane comprising LAMP-1 (CD107A). In some embodiments, about 40% or less of the megakaryocyte-derived extracellular vesicles comprise a lipid bilayer membrane comprising LAMP-1 (CD107A). In some embodiments, about 60% or less of the megakaryocyte-derived extracellular vesicles comprise a lipid bilayer membrane comprising LAMP-1 (CD107A). In some embodiments, about 70% or less of the megakaryocyte-derived extracellular vesicles comprise a lipid bilayer membrane comprising LAMP-1 (CD107A). In some embodiments, about 80% or less of the megakaryocyte-derived extracellular vesicles comprise a lipid bilayer membrane comprising LAMP-1 (CD107A). In some embodiments, about 90% or less of the megakaryocyte-derived extracellular vesicles comprise a lipid bilayer membrane comprising LAMP-1 (CD107A). In some embodiments, about 95% or less of the megakaryocyte-derived extracellular vesicles comprise a lipid bilayer membrane comprising LAMP-1 (CD107A). In some embodiments, about 99% or less of the megakaryocyte-derived extracellular vesicles comprise a lipid bilayer membrane comprising LAMP-1 (CD107A).

In some embodiments, less than about 50% of the megakaryocyte-derived extracellular vesicles comprise a lipid bilayer membrane comprising LAMP-1 (CD107A). In embodiments, less than about 40% of the megakaryocyte-derived extracellular vesicles comprise a lipid bilayer membrane comprising LAMP-1 (CD107A). In some embodiments, less than about 30% of the megakaryocyte-derived extracellular vesicles comprise a lipid bilayer membrane comprising LAMP-1 (CD107A). In some embodiments, less than about 25% of the megakaryocyte-derived extracellular vesicles comprise a lipid bilayer membrane comprising LAMP-1 (CD107A). In some embodiments, less than about 20% of the megakaryocyte-derived extracellular vesicles comprise a lipid bilayer membrane comprising LAMP-1 (CD107A). In some embodiments, less than about 15% of the megakaryocyte-derived extracellular vesicles comprise a lipid bilayer membrane comprising LAMP-1 (CD107A). In some embodiments, less than about 10% of the megakaryocyte-derived extracellular vesicles comprise a lipid bilayer membrane comprising LAMP-1 (CD107A). In some embodiments, less than about 5% of the megakaryocyte-derived extracellular vesicles comprise a lipid bilayer membrane comprising LAMP-1 (CD107A). In some embodiments, less than about 1% of the megakaryocyte-derived extracellular vesicles comprise a lipid bilayer membrane comprising LAMP-1 (CD107A).

In some embodiments, between about 1% to about 99% of the megakaryocyte-derived extracellular vesicles comprise a lipid bilayer membrane comprising LAMP-1 (CD107A). In some embodiments, between about 1% to about 50% of the megakaryocyte-derived extracellular vesicles comprise a lipid bilayer membrane comprising LAMP-1 (CD107A). In some embodiments, between about 1% to about 25% of the megakaryocyte-derived extracellular vesicles comprise a lipid bilayer membrane comprising LAMP-1 (CD107A). In some embodiments, between about 1% to about 10% of the megakaryocyte-derived extracellular vesicles comprise a lipid bilayer membrane comprising LAMP-1 (CD107A). In some embodiments, between about 1% to about 5% of the megakaryocyte-derived extracellular vesicles comprise a lipid bilayer membrane comprising LAMP-1 (CD107A). In some embodiments, between about 1% to about 2% of the megakaryocyte-derived extracellular vesicles comprise a lipid bilayer membrane comprising LAMP-1 (CD107A). In some embodiments, between about 50% to about 99% of the megakaryocyte-derived extracellular vesicles comprise a lipid bilayer membrane comprising LAMP-1 (CD107A). In some embodiments, between about 75% to about 99% of the megakaryocyte-derived extracellular vesicles comprise a lipid bilayer membrane comprising LAMP-1 (CD107A). In some embodiments, between about 90% to about 99% of the megakaryocyte-derived extracellular vesicles comprise a lipid bilayer membrane comprising LAMP-1 (CD107A). In some embodiments, between about 95% to about 99% of the megakaryocyte-derived extracellular vesicles comprise a lipid bilayer membrane comprising LAMP-1 (CD107A).

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising LAMP-1 (CD107A).

In embodiments, the megakaryocyte-derived extracellular vesicles are free of, or substantially free of LAMP-1 (CD107A).

In embodiments, the megakaryocyte-derived extracellular vesicles are characterized by a higher expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1-fold to about a 2-fold, lower amount of LAMP-1 (CD107A) than platelet free plasma (PFP) MkEVs. In embodiments, the megakaryocyte-derived extracellular vesicles have an amount of LAMP-1 (CD107A) that is substantially the same as platelet free plasma (PFP) MkEVs. In embodiments, the megakaryocyte-derived extracellular vesicles have about a 2-fold to about a 8-fold, or about a 2-fold to about a 4-fold lower amount of LAMP-1 (CD107A) than platelet derived extracellular vesicles (PLT EVs). In embodiments, the megakaryocyte-derived extracellular vesicles have about a 3-fold or about a 4-fold lower amount of LAMP-1 (CD107A) than platelet derived extracellular vesicles (PLT EVs).

In embodiments, greater than about 50% of the megakaryocyte-derived extracellular vesicles comprise a lipid bilayer membrane comprising CD63. In some embodiments, greater than about 40% of the megakaryocyte-derived extracellular vesicles comprise a lipid bilayer membrane comprising CD63. In some embodiments, greater than about 60% of the megakaryocyte-derived extracellular vesicles comprise a lipid bilayer membrane comprising CD63. In some embodiments, greater than about 70% of the megakaryocyte-derived extracellular vesicles comprise a lipid bilayer membrane comprising CD63. In some embodiments, greater than about 80% of the megakaryocyte-derived extracellular vesicles comprise a lipid bilayer membrane comprising CD63. In some embodiments, greater than about 90% of the megakaryocyte-derived extracellular vesicles comprise a lipid bilayer membrane comprising CD63. In some embodiments, greater than about 95% of the megakaryocyte-derived extracellular vesicles comprise a lipid bilayer membrane comprising CD63. In some embodiments, greater than about 99% of the megakaryocyte-derived extracellular vesicles comprise a lipid bilayer membrane comprising CD63.

In embodiments, about 50% or less of the megakaryocyte-derived extracellular vesicles comprise a lipid bilayer membrane comprising CD63. In some embodiments, about 40% or less of the megakaryocyte-derived extracellular vesicles comprise a lipid bilayer membrane comprising CD63. In some embodiments, about 60% or less of the megakaryocyte-derived extracellular vesicles comprise a lipid bilayer membrane comprising CD63. In some embodiments, about 70% or less of the megakaryocyte-derived extracellular vesicles comprise a lipid bilayer membrane comprising CD63. In some embodiments, about 80% or less of the megakaryocyte-derived extracellular vesicles comprise a lipid bilayer membrane comprising CD63. In some embodiments, about 90% or less of the megakaryocyte-derived extracellular vesicles comprise a lipid bilayer membrane comprising CD63. In some embodiments, about 95% or less of the megakaryocyte-derived extracellular vesicles comprise a lipid bilayer membrane comprising CD63. In some embodiments, about 99% or less of the megakaryocyte-derived extracellular vesicles comprise a lipid bilayer membrane comprising CD63.

In some embodiments, less than about 50% of the megakaryocyte-derived extracellular vesicles comprise a lipid bilayer membrane comprising CD63. In embodiments, less than about 40% of the megakaryocyte-derived extracellular vesicles comprise a lipid bilayer membrane comprising CD63. In some embodiments, less than about 30% of the megakaryocyte-derived extracellular vesicles comprise a lipid bilayer membrane comprising CD63. In some embodiments, less than about 25% of the megakaryocyte-derived extracellular vesicles comprise a lipid bilayer membrane comprising CD63. In some embodiments, less than about 20% of the megakaryocyte-derived extracellular vesicles comprise a lipid bilayer membrane comprising CD63. In some embodiments, less than about 15% of the megakaryocyte-derived extracellular vesicles comprise a lipid bilayer membrane comprising CD63. In some embodiments, less than about 10% of the megakaryocyte-derived extracellular vesicles comprise a lipid bilayer membrane comprising CD63. In some embodiments, less than about 5% of the megakaryocyte-derived extracellular vesicles comprise a lipid bilayer membrane comprising CD63. In some embodiments, less than about 1% of the megakaryocyte-derived extracellular vesicles comprise a lipid bilayer membrane comprising CD63.

In some embodiments, between about 1% to about 99% of the megakaryocyte-derived extracellular vesicles comprise a lipid bilayer membrane comprising CD63. In some embodiments, between about 1% to about 50% of the megakaryocyte-derived extracellular vesicles comprise a lipid bilayer membrane comprising CD63. In some embodiments, between about 1% to about 25% of the megakaryocyte-derived extracellular vesicles comprise a lipid bilayer membrane comprising CD63. In some embodiments, between about 1% to about 10% of the megakaryocyte-derived extracellular vesicles comprise a lipid bilayer membrane comprising CD63. In some embodiments, between about 1% to about 5% of the megakaryocyte-derived extracellular vesicles comprise a lipid bilayer membrane comprising CD63. In some embodiments, between about 1% to about 2% of the megakaryocyte-derived extracellular vesicles comprise a lipid bilayer membrane comprising CD63. In some embodiments, between about 50% to about 99% of the megakaryocyte-derived extracellular vesicles comprise a lipid bilayer membrane comprising CD63. In some embodiments, between about 75% to about 99% of the megakaryocyte-derived extracellular vesicles comprise a lipid bilayer membrane comprising CD63. In some embodiments, between about 90% to about 99% of the megakaryocyte-derived extracellular vesicles comprise a lipid bilayer membrane comprising CD63. In some embodiments, between about 95% to about 99% of the megakaryocyte-derived extracellular vesicles comprise a lipid bilayer membrane comprising CD63.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD63.

In some embodiments, between about 1% to about 30% of the megakaryocyte-derived extracellular vesicles comprise a lipid bilayer membrane comprising CD63. In some embodiments, between about 5% to about 25% of the megakaryocyte-derived extracellular vesicles comprise a lipid bilayer membrane comprising CD63. In some embodiments, between about 10% to about 20% of the megakaryocyte-derived extracellular vesicles comprise a lipid bilayer membrane comprising CD63. In some embodiments, between about 13% to about 19% of the megakaryocyte-derived extracellular vesicles comprise a lipid bilayer membrane comprising CD63.

In embodiments, the megakaryocyte-derived extracellular vesicles are characterized by a higher expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD63 than platelet free plasma (PFP) MkEVs. In embodiments, the megakaryocyte-derived extracellular vesicles have about a 2-fold or about a 3-fold greater amount of CD63 than platelet free plasma (PFP) MkEVs. In embodiments, the megakaryocyte-derived extracellular vesicles have about a 1.1-fold to about a 2-fold lower amount of CD63 than platelet derived extracellular vesicles (PLT EVs). In embodiments, the megakaryocyte-derived extracellular vesicles have about a 1.1- fold or about a 1.2-fold lower amount of CD63 than platelet derived extracellular vesicles (PLT EVs). In embodiments, the megakaryocyte-derived extracellular vesicles have an amount of CD63 that is substantially the same as platelet derived extracellular vesicles (PLT EVs).

In embodiments, greater than about 50% of the mega-karyocyte-derived extracellular vesicles comprise a lipid bilayer membrane comprising CD42b. In some embodiments, greater than about 40% of the megakaryocyte-derived extracellular vesicles comprise a lipid bilayer membrane comprising CD42b. In some embodiments, greater than about 60% of the megakaryocyte-derived extracellular vesicles comprise a lipid bilayer membrane comprising CD42b. In some embodiments, greater than about 70% of the megakaryocyte-derived extracellular vesicles comprise a lipid bilayer membrane comprising CD42b.

In some embodiments, greater than about 80% of the megakaryocyte-derived extracellular vesicles comprise a lipid bilayer membrane comprising CD42b. In some embodiments, greater than about 90% of the megakaryo-cyte-derived extracellular vesicles comprise a lipid bilayer membrane comprising CD42b. In some embodiments, greater than about 95% of the megakaryocyte-derived extra-cellular vesicles comprise a lipid bilayer membrane comprising CD42b. In some embodiments, greater than about 99% of the megakaryocyte-derived extracellular vesicles comprise a lipid bilayer membrane comprising CD42b.

In embodiments, about 50% or less of the megakaryocyte-derived extracellular vesicles comprise a lipid bilayer membrane comprising CD42b. In some embodiments, about 40% or less of the megakaryocyte-derived extracellular vesicles comprise a lipid bilayer membrane comprising CD42b. In some embodiments, about 60% or less of the megakaryo-cyte-derived extracellular vesicles comprise a lipid bilayer membrane comprising CD42b. In some embodiments, about 70% or less of the megakaryocyte-derived extracellular vesicles comprise a lipid bilayer membrane comprising CD42b. In some embodiments, about 80% or less of the megakaryocyte-derived extracellular vesicles comprise a lipid bilayer membrane comprising CD42b. In some embodiments, about 90% or less of the megakaryocyte-derived extracellular vesicles comprise a lipid bilayer membrane comprising CD42b. In some embodiments, about 95% or less of the megakaryocyte-derived extracellular vesicles comprise a lipid bilayer membrane comprising CD42b. In some embodiments, about 99% or less of the megakaryo-cyte-derived extracellular vesicles comprise a lipid bilayer membrane comprising CD42b.

In some embodiments, less than about 50% of the mega-karyocyte-derived extracellular vesicles comprise a lipid bilayer membrane comprising CD42b. In embodiments, less than about 40% of the megakaryocyte-derived extracellular vesicles comprise a lipid bilayer membrane comprising CD42b. In some embodiments, less than about 30% of the megakaryocyte-derived extracellular vesicles comprise a lipid bilayer membrane comprising CD42b. In some embodiments, less than about 25% of the megakaryocyte-derived extracellular vesicles comprise a lipid bilayer membrane comprising CD42b. In some embodiments, less than about 20% of the megakaryocyte-derived extracellular vesicles comprise a lipid bilayer membrane comprising CD42b. In some embodiments, less than about 15% of the megakaryocyte-derived extracellular vesicles comprise a lipid bilayer membrane comprising CD42b. In some embodiments, less than about 10% of the megakaryocyte-derived extracellular vesicles comprise a lipid bilayer membrane comprising CD42b. In some embodiments, less than about 5% of the megakaryocyte-derived extracellular vesicles comprise a lipid bilayer membrane comprising CD42b. In some embodiments, less than about 1% of the megakaryocyte-derived extracellular vesicles comprise a lipid bilayer membrane comprising CD42b.

In some embodiments, between about 1% to about 99% of the megakaryocyte-derived extracellular vesicles comprise a lipid bilayer membrane comprising CD42b. In some embodiments, between about 1% to about 50% of the megakaryocyte-derived extracellular vesicles comprise a lipid bilayer membrane comprising CD42b. In some embodiments, between about 1% to about 25% of the megakaryocyte-derived extracellular vesicles comprise a lipid bilayer membrane comprising CD42b. In some embodiments, between about 1% to about 10% of the megakaryocyte-derived extracellular vesicles comprise a lipid bilayer membrane comprising CD42b. In some embodiments, between about 1% to about 5% of the mega-karyocyte-derived extracellular vesicles comprise a lipid bilayer membrane comprising CD42b. In some embodi-ments, between about 1% to about 2% of the megakaryo-cyte-derived extracellular vesicles comprise a lipid bilayer membrane comprising CD42b. In some embodiments, between about 50% to about 99% of the megakaryocyte-derived extracellular vesicles comprise a lipid bilayer mem-brane comprising CD42b. In some embodiments, between about 75% to about 99% of the megakaryocyte-derived extracellular vesicles comprise a lipid bilayer membrane comprising CD42b. In some embodiments, between about 90% to about 99% of the megakaryocyte-derived extracel-lular vesicles comprise a lipid bilayer membrane comprising CD42b. In some embodiments, between about 95% to about 99% of the megakaryocyte-derived extracellular vesicles comprise a lipid bilayer membrane comprising CD42b.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD42b.

In embodiments, the megakaryocyte-derived extracellular vesicles are characterized by a higher expression and/or presence of CD42b than naturally-occurring megakaryo-cyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 32-fold, or about a 10-fold to about a 20-fold lower amount of CD42b than platelet free plasma (PFP) MkEVs. In embodiments, the megakaryocyte-derived extracellular vesicles have about a 16-fold or about a 20-fold lower amount of CD42b than platelet free plasma (PFP) MkEVs. In embodiments, the megakaryocyte-derived extracellular vesicles have about a 64-fold to about a 128-fold, or about a 50-fold to about a 75-fold lower amount of CD42b than platelet derived extracellular vesicles (PLT EVs). In embodiments, the megakaryocyte-derived extracellular vesicles have about a 64-fold or about a 70-fold lower amount of CD42b than platelet derived extracellular vesicles (PLT EVs).

In embodiments, greater than about 50% of the megakaryocyte-derived extracellular vesicles comprise a lipid bilayer membrane comprising CD9. In some embodiments, greater than about 40% of the megakaryocyte-derived extracellular vesicles comprise a lipid bilayer membrane comprising CD9. In some embodiments, greater than about 60% of the megakaryocyte-derived extracellular vesicles comprise a lipid bilayer membrane comprising CD9. In some embodiments, greater than about 70% of the megakaryocyte-derived extracellular vesicles comprise a lipid bilayer membrane comprising CD9. In some embodiments, greater than about 80% of the megakaryocyte-derived extracellular vesicles comprise a lipid bilayer membrane comprising CD9. In some embodiments, greater than about 90% of the megakaryocyte-derived extracellular vesicles comprise a lipid bilayer membrane comprising CD9. In some embodiments, greater than about 95% of the megakaryocyte-derived extracellular vesicles comprise a lipid bilayer membrane comprising CD9. In some embodiments, greater than about 99% of the megakaryocyte-derived extracellular vesicles comprise a lipid bilayer membrane comprising CD9.

In embodiments, about 50% or less of the megakaryocyte-derived extracellular vesicles comprise a lipid bilayer membrane comprising CD9. In some embodiments, about 40% or less of the megakaryocyte-derived extracellular vesicles comprise a lipid bilayer membrane comprising CD9. In some embodiments, about 60% or less of the megakaryocyte-derived extracellular vesicles comprise a lipid bilayer membrane comprising CD9. In some embodiments, about 70% or less of the megakaryocyte-derived extracellular vesicles comprise a lipid bilayer membrane comprising CD9. In some embodiments, about 80% or less of the megakaryocyte-derived extracellular vesicles comprise a lipid bilayer membrane comprising CD9. In some embodiments, about 90% or less of the megakaryocyte-derived extracellular vesicles comprise a lipid bilayer membrane comprising CD9. In some embodiments, about 95% or less of the megakaryocyte-derived extracellular vesicles comprise a lipid bilayer membrane comprising CD9. In some embodiments, about 99% or less of the megakaryocyte-derived extracellular vesicles comprise a lipid bilayer membrane comprising CD9.

In some embodiments, less than about 50% of the megakaryocyte-derived extracellular vesicles comprise a lipid bilayer membrane comprising CD9. In embodiments, less than about 40% of the megakaryocyte-derived extracellular vesicles comprise a lipid bilayer membrane comprising CD9. In some embodiments, less than about 30% of the megakaryocyte-derived extracellular vesicles comprise a lipid bilayer membrane comprising CD9. In some embodiments, less than about 25% of the megakaryocyte-derived extracellular vesicles comprise a lipid bilayer membrane comprising CD9. In some embodiments, less than about 20% of the megakaryocyte-derived extracellular vesicles comprise a lipid bilayer membrane comprising CD9. In some embodiments, less than about 15% of the megakaryocyte-derived extracellular vesicles comprise a lipid bilayer membrane comprising CD9. In some embodiments, less than about 10% of the megakaryocyte-derived extracellular vesicles comprise a lipid bilayer membrane comprising CD9. In some embodiments, less than about 5% of the megakaryocyte-derived extracellular vesicles comprise a lipid bilayer membrane comprising CD9. In some embodiments, less than about 1% of the megakaryocyte-derived extracellular vesicles comprise a lipid bilayer membrane comprising CD9.

In some embodiments, between about 1% to about 99% of the megakaryocyte-derived extracellular vesicles comprise a lipid bilayer membrane comprising CD9. In some embodiments, between about 1% to about 50% of the megakaryocyte-derived extracellular vesicles comprise a lipid bilayer membrane comprising CD9. In some embodiments, between about 1% to about 25% of the megakaryocyte-derived extracellular vesicles comprise a lipid bilayer membrane comprising CD9. In some embodiments, between about 1% to about 10% of the megakaryocyte-derived extracellular vesicles comprise a lipid bilayer membrane comprising CD9. In some embodiments, between about 1% to about 5% of the megakaryocyte-derived extracellular vesicles comprise a lipid bilayer membrane comprising CD9. In some embodiments, between about 1% to about 2% of the megakaryocyte-derived extracellular vesicles comprise a lipid bilayer membrane comprising CD9. In some embodiments, between about 50% to about 99% of the megakaryocyte-derived extracellular vesicles comprise a lipid bilayer membrane comprising CD9. In some embodiments, between about 75% to about 99% of the megakaryocyte-derived extracellular vesicles comprise a lipid bilayer membrane comprising CD9. In some embodiments, between about 90% to about 99% of the megakaryocyte-derived extracellular vesicles comprise a lipid bilayer membrane comprising CD9. In some embodiments, between about 95% to about 99% of the megakaryocyte-derived extracellular vesicles comprise a lipid bilayer membrane comprising CD9.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD9.

In some embodiments, between about 50% to about 70% of the megakaryocyte-derived extracellular vesicles comprise a lipid bilayer membrane comprising CD9. In some embodiments, between about 60% to about 70% of the megakaryocyte-derived extracellular vesicles comprise a lipid bilayer membrane comprising CD9. In some embodiments, between about 62% to about 68% of the megakaryocyte-derived extracellular vesicles comprise a lipid bilayer membrane comprising CD9. In some embodiments, between about 65% to about 66% of the megakaryocyte-derived extracellular vesicles comprise a lipid bilayer membrane comprising CD9.

In some embodiments, between about 50% to about 99% of the megakaryocyte-derived extracellular vesicles comprise a lipid bilayer membrane comprising CD9.

In embodiments, the megakaryocyte-derived extracellular vesicles are characterized by a higher expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.5-fold to about a 4-fold, or about a 2-fold to about a 4-fold greater amount of CD9 than platelet free plasma (PFP) MkEVs. In embodiments, the megakaryocyte-derived extracellular vesicles have about a 2-fold greater amount of CD9 than platelet free plasma (PFP) MkEVs. In embodiments, the megakaryocyte-derived extracellular vesicles have about a 1.1-fold to about a 2-fold lower amount of CD9 than platelet derived extracellular vesicles (PLT EVs). In embodiments, the megakaryocyte-derived extracellular vesicles have about a 1.1-fold or about a 1.2-fold lower amount of CD9 than platelet derived extracellular vesicles (PLT EVs). In embodiments, the megakaryocyte-derived extracellular vesicles have an amount of CD9 that is substantially the same as platelet derived extracellular vesicles (PLT EVs).

In embodiments, greater than about 50% of the megakaryocyte-derived extracellular vesicles comprise a lipid bilayer membrane comprising CD31. In some embodiments, greater than about 40% of the megakaryocyte-derived extracellular vesicles comprise a lipid bilayer membrane comprising CD31. In some embodiments, greater than about 60% of the megakaryocyte-derived extracellular vesicles comprise a lipid bilayer membrane comprising CD31. In some embodiments, greater than about 70% of the megakaryocyte-derived extracellular vesicles comprise a lipid bilayer membrane comprising CD31. In some embodiments, greater than about 80% of the megakaryocyte-derived extracellular vesicles comprise a lipid bilayer membrane comprising CD31. In some embodiments, greater than about 90% of the megakaryocyte-derived extracellular vesicles comprise a lipid bilayer membrane comprising CD31.

In some embodiments, greater than about 95% of the megakaryocyte-derived extracellular vesicles comprise a lipid bilayer membrane comprising CD31. In some embodiments, greater than about 99% of the megakaryocyte-derived extracellular vesicles comprise a lipid bilayer membrane comprising CD31.

In embodiments, about 50% or less of the megakaryocyte-derived extracellular vesicles comprise a lipid bilayer membrane comprising CD31. In some embodiments, about 40% or less of the megakaryocyte-derived extracellular vesicles comprise a lipid bilayer membrane comprising CD31. In some embodiments, about 60% or less of the megakaryocyte-derived extracellular vesicles comprise a lipid bilayer membrane comprising CD31. In some embodiments, about 70% or less of the megakaryocyte-derived extracellular vesicles comprise a lipid bilayer membrane comprising CD31. In some embodiments, about 80% or less of the megakaryocyte-derived extracellular vesicles comprise a lipid bilayer membrane comprising CD31. In some embodiments, about 90% or less of the megakaryocyte-derived extracellular vesicles comprise a lipid bilayer membrane comprising CD31. In some embodiments, about 95% or less of the megakaryocyte-derived extracellular vesicles comprise a lipid bilayer membrane comprising CD31. In some embodiments, about 99% or less of the megakaryocyte-derived extracellular vesicles comprise a lipid bilayer membrane comprising CD31.

In some embodiments, less than about 50% of the megakaryocyte-derived extracellular vesicles comprise a lipid bilayer membrane comprising CD31. In embodiments, less than about 40% of the megakaryocyte-derived extracellular vesicles comprise a lipid bilayer membrane comprising CD31. In some embodiments, less than about 30% of the megakaryocyte-derived extracellular vesicles comprise a lipid bilayer membrane comprising CD31. In some embodiments, less than about 25% of the megakaryocyte-derived extracellular vesicles comprise a lipid bilayer membrane comprising CD31. In some embodiments, less than about 20% of the megakaryocyte-derived extracellular vesicles comprise a lipid bilayer membrane comprising CD31. In some embodiments, less than about 15% of the megakaryocyte-derived extracellular vesicles comprise a lipid bilayer membrane comprising CD31. In some embodiments, less than about 10% of the megakaryocyte-derived extracellular vesicles comprise a lipid bilayer membrane comprising CD31. In some embodiments, less than about 5% of the megakaryocyte-derived extracellular vesicles comprise a lipid bilayer membrane comprising CD31. In some embodiments, less than about 1% of the megakaryocyte-derived extracellular vesicles comprise a lipid bilayer membrane comprising CD31.

In some embodiments, between about 1% to about 99% of the megakaryocyte-derived extracellular vesicles comprise a lipid bilayer membrane comprising CD31. In some embodiments, between about 1% to about 50% of the megakaryocyte-derived extracellular vesicles comprise a lipid bilayer membrane comprising CD31. In some embodiments, between about 1% to about 25% of the megakaryocyte-derived extracellular vesicles comprise a lipid bilayer membrane comprising CD31. In some embodiments, between about 1% to about 10% of the megakaryocyte-derived extracellular vesicles comprise a lipid bilayer membrane comprising CD31. In some embodiments, between about 1% to about 5% of the megakaryocyte-derived extracellular vesicles comprise a lipid bilayer membrane comprising CD31. In some embodiments, between about 1% to about 2% of the megakaryocyte-derived extracellular vesicles comprise a lipid bilayer membrane comprising CD31. In some embodiments, between about 50% to about 99% of the megakaryocyte-derived extracellular vesicles comprise a lipid bilayer membrane comprising CD31. In some embodiments, between about 75% to about 99% of the megakaryocyte-derived extracellular vesicles comprise a lipid bilayer membrane comprising CD31. In some embodiments, between about 90% to about 99% of the megakaryocyte-derived extracellular vesicles comprise a lipid bilayer membrane comprising CD31. In some embodiments, between about 95% to about 99% of the megakaryocyte-derived extracellular vesicles comprise a lipid bilayer membrane comprising CD31.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD31.

In some embodiments, between about 5% to about 50% of the megakaryocyte-derived extracellular vesicles comprise a lipid bilayer membrane comprising CD31. In some embodiments, between about 10% to about 40% of the megakaryocyte-derived extracellular vesicles comprise a lipid bilayer membrane comprising CD31. In some embodiments, between about 10% to about 35% of the megakaryocyte-derived extracellular vesicles comprise a lipid bilayer membrane comprising CD31. In some embodiments, between about 13% to about 31% of the megakaryocyte-derived extracellular vesicles comprise a lipid bilayer membrane comprising CD31.

In embodiments, the megakaryocyte-derived extracellular vesicles are characterized by a higher expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD31 than platelet free plasma (PFP) MkEVs. In embodiments, the megakaryocyte-derived extracellular vesicles have about a 1.5-fold lower amount of CD31 than platelet free plasma (PFP) MkEVs. In embodiments, the megakaryocyte-derived extracellular vesicles have about a 2-fold to about a 4-fold lower amount of CD31 than platelet derived extracellular vesicles (PLT EVs). In embodiments, the megakaryocyte-derived extracellular vesicles have about a 2-fold or about a 3-fold lower amount of CD31 than platelet derived extracellular vesicles (PLT EVs).

In embodiments, greater than about 50% of the megakaryocyte-derived extracellular vesicles comprise a lipid bilayer membrane comprising CD47. In some embodiments, greater than about 40% of the megakaryocyte-derived extracellular vesicles comprise a lipid bilayer membrane comprising CD47. In some embodiments, greater than about 60% of the megakaryocyte-derived extracellular vesicles comprise a lipid bilayer membrane comprising CD47. In some embodiments, greater than about 70% of the megakaryocyte-derived extracellular vesicles comprise a lipid bilayer membrane comprising CD47. In some embodiments, greater than about 80% of the megakaryocyte-derived extracellular vesicles comprise a lipid bilayer membrane comprising CD47. In some embodiments, greater than about 90% of the megakaryocyte-derived extracellular vesicles comprise a lipid bilayer membrane comprising CD47. In some embodiments, greater than about 95% of the megakaryocyte-derived extracellular vesicles comprise a lipid bilayer membrane comprising CD47. In some embodiments, greater than about 99% of the megakaryocyte-derived extracellular vesicles comprise a lipid bilayer membrane comprising CD47.

In embodiments, about 50% or less of the megakaryocyte-derived extracellular vesicles comprise a lipid bilayer membrane comprising CD47. In some embodiments, about 40% or less of the megakaryocyte-derived extracellular vesicles comprise a lipid bilayer membrane comprising CD47. In some embodiments, about 60% or less of the megakaryocyte-derived extracellular vesicles comprise a lipid bilayer membrane comprising CD47. In some embodiments, about 70% or less of the megakaryocyte-derived extracellular vesicles comprise a lipid bilayer membrane comprising CD47. In some embodiments, about 80% or less of the megakaryocyte-derived extracellular vesicles comprise a lipid bilayer membrane comprising CD47. In some embodiments, about 90% or less of the megakaryocyte-derived extracellular vesicles comprise a lipid bilayer membrane comprising CD47. In some embodiments, about 95% or less of the megakaryocyte-derived extracellular vesicles comprise a lipid bilayer membrane comprising CD47. In some embodiments, about 99% or less of the megakaryocyte-derived extracellular vesicles comprise a lipid bilayer membrane comprising CD47.

In some embodiments, less than about 50% of the megakaryocyte-derived extracellular vesicles comprise a lipid bilayer membrane comprising CD47. In embodiments, less than about 40% of the megakaryocyte-derived extracellular vesicles comprise a lipid bilayer membrane comprising CD47. In some embodiments, less than about 30% of the megakaryocyte-derived extracellular vesicles comprise a lipid bilayer membrane comprising CD47. In some embodiments, less than about 25% of the megakaryocyte-derived extracellular vesicles comprise a lipid bilayer membrane comprising CD47. In some embodiments, less than about 20% of the megakaryocyte-derived extracellular vesicles comprise a lipid bilayer membrane comprising CD47. In some embodiments, less than about 15% of the megakaryocyte-derived extracellular vesicles comprise a lipid bilayer membrane comprising CD47. In some embodiments, less than about 10% of the megakaryocyte-derived extracellular vesicles comprise a lipid bilayer membrane comprising CD47. In some embodiments, less than about 5% of the megakaryocyte-derived extracellular vesicles comprise a lipid bilayer membrane comprising CD47. In some embodiments, less than about 1% of the megakaryocyte-derived extracellular vesicles comprise a lipid bilayer membrane comprising CD47.

In some embodiments, between about 1% to about 99% of the megakaryocyte-derived extracellular vesicles comprise a lipid bilayer membrane comprising CD47. In some embodiments, between about 1% to about 50% of the megakaryocyte-derived extracellular vesicles comprise a lipid bilayer membrane comprising CD47. In some embodiments, between about 1% to about 25% of the megakaryocyte-derived extracellular vesicles comprise a lipid bilayer membrane comprising CD47. In some embodiments, between about 1% to about 10% of the megakaryocyte-derived extracellular vesicles comprise a lipid bilayer membrane comprising CD47. In some embodiments, between about 1% to about 5% of the megakaryocyte-derived extracellular vesicles comprise a lipid bilayer membrane comprising CD47. In some embodiments, between about 1% to about 2% of the megakaryocyte-derived extracellular vesicles comprise a lipid bilayer membrane comprising CD47. In some embodiments, between about 50% to about 99% of the megakaryocyte-derived extracellular vesicles comprise a lipid bilayer membrane comprising CD47. In some embodiments, between about 75% to about 99% of the megakaryocyte-derived extracellular vesicles comprise a lipid bilayer membrane comprising CD47. In some embodiments, between about 90% to about 99% of the megakaryocyte-derived extracellular vesicles comprise a lipid bilayer membrane comprising CD47. In some embodiments, between about 95% to about 99% of the megakaryocyte-derived extracellular vesicles comprise a lipid bilayer membrane comprising CD47.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD47.

In some embodiments, between about 1% to about 50% of the megakaryocyte-derived extracellular vesicles comprise a lipid bilayer membrane comprising CD47. In some embodiments, between about 10% to about 40% of the megakaryocyte-derived extracellular vesicles comprise a lipid bilayer membrane comprising CD47. In some embodiments, between about 20% to about 40% of the megakaryocyte-derived extracellular vesicles comprise a lipid bilayer membrane comprising CD47. In some embodiments, between about 25% to about 35% of the megakaryocyte-derived extracellular vesicles comprise a lipid bilayer membrane comprising CD47.

In embodiments, the megakaryocyte-derived extracellular vesicles are characterized by a higher expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 128-fold to about a 512-fold, or about a 256-fold to about a 512-fold, or about a 250-fold to about a 300-fold greater amount of CD47 than platelet free plasma (PFP) MkEVs. In embodiments, the megakaryocyte-derived extracellular vesicles have about a 256-fold or about a 300-fold greater amount of CD47 than platelet free plasma (PFP) MkEVs. In embodiments, the megakaryocyte-derived extracellular vesicles have about a 1.1-fold to about a 2-fold lower amount of CD47 than platelet derived extracellular vesicles (PLT EVs). In embodiments, the megakaryocyte-derived extracellular vesicles have about a 1.1-fold or about a 1.5-fold lower amount of CD47 than platelet derived extracellular vesicles (PLT EVs). In embodiments, the megakaryocyte-derived extracellular vesicles have an amount of CD47 that is substantially the same as platelet derived extracellular vesicles (PLT EVs).

In embodiments, greater than about 50% of the megakaryocyte-derived extracellular vesicles comprise a lipid bilayer membrane comprising CD147. In some embodiments, greater than about 40% of the megakaryocyte-derived extracellular vesicles comprise a lipid bilayer membrane comprising CD147. In some embodiments, greater than about 60% of the megakaryocyte-derived extracellular vesicles comprise a lipid bilayer membrane comprising CD147. In some embodiments, greater than about 70% of the megakaryocyte-derived extracellular vesicles comprise a lipid bilayer membrane comprising CD147. In some embodiments, greater than about 80% of the megakaryocyte-derived extracellular vesicles comprise a lipid bilayer membrane comprising CD147. In some embodiments, greater than about 90% of the megakaryocyte-derived extracellular vesicles comprise a lipid bilayer membrane comprising CD147. In some embodiments, greater than about 95% of the megakaryocyte-derived extracellular vesicles comprise a lipid bilayer membrane comprising CD147. In some embodiments, greater than about 99% of the megakaryocyte-derived extracellular vesicles comprise a lipid bilayer membrane comprising CD147.

In embodiments, about 50% or less of the megakaryocyte-derived extracellular vesicles comprise a lipid bilayer membrane comprising CD147. In some embodiments, about 40% or less of the megakaryocyte-derived extracellular vesicles comprise a lipid bilayer membrane comprising CD147. In some embodiments, about 60% or less of the megakaryocyte-derived extracellular vesicles comprise a lipid bilayer membrane comprising CD147. In some embodiments, about 70% or less of the megakaryocyte-derived extracellular vesicles comprise a lipid bilayer membrane comprising CD147. In some embodiments, about 80% or less of the megakaryocyte-derived extracellular vesicles comprise a lipid bilayer membrane comprising CD147. In some embodiments, about 90% or less of the megakaryocyte-derived extracellular vesicles comprise a lipid bilayer membrane comprising CD147. In some embodiments, about 95% or less of the megakaryocyte-derived extracellular vesicles comprise a lipid bilayer membrane comprising CD147. In some embodiments, about 99% or less of the megakaryocyte-derived extracellular vesicles comprise a lipid bilayer membrane comprising CD147.

In some embodiments, less than about 50% of the megakaryocyte-derived extracellular vesicles comprise a lipid bilayer membrane comprising CD147. In embodiments, less than about 40% of the megakaryocyte-derived extracellular vesicles comprise a lipid bilayer membrane comprising CD147. In some embodiments, less than about 30% of the megakaryocyte-derived extracellular vesicles comprise a lipid bilayer membrane comprising CD147. In some embodiments, less than about 25% of the megakaryocyte-derived extracellular vesicles comprise a lipid bilayer membrane comprising CD147. In some embodiments, less than about 20% of the megakaryocyte-derived extracellular vesicles comprise a lipid bilayer membrane comprising CD147. In some embodiments, less than about 15% of the megakaryocyte-derived extracellular vesicles comprise a lipid bilayer membrane comprising CD147. In some embodiments, less than about 10% of the megakaryocyte-derived extracellular vesicles comprise a lipid bilayer membrane comprising CD147. In some embodiments, less than about 5% of the megakaryocyte-derived extracellular vesicles comprise a lipid bilayer membrane comprising CD147. In some embodiments, less than about 1% of the megakaryocyte-derived extracellular vesicles comprise a lipid bilayer membrane comprising CD147.

In some embodiments, between about 1% to about 99% of the megakaryocyte-derived extracellular vesicles comprise a lipid bilayer membrane comprising CD147. In some embodiments, between about 1% to about 50% of the megakaryocyte-derived extracellular vesicles comprise a lipid bilayer membrane comprising CD147. In some embodiments, between about 1% to about 25% of the megakaryocyte-derived extracellular vesicles comprise a lipid bilayer membrane comprising CD147. In some embodiments, between about 1% to about 10% of the megakaryocyte-derived extracellular vesicles comprise a lipid bilayer membrane comprising CD147. In some embodiments, between about 1% to about 5% of the megakaryocyte-derived extracellular vesicles comprise a lipid bilayer membrane comprising CD147. In some embodiments, between about 1% to about 2% of the megakaryocyte-derived extracellular vesicles comprise a lipid bilayer membrane comprising CD147. In some embodiments, between about 50% to about 99% of the megakaryocyte-derived extracellular vesicles comprise a lipid bilayer membrane comprising CD147. In some embodiments, between about 75% to about 99% of the megakaryocyte-derived extracellular vesicles comprise a lipid bilayer membrane comprising CD147. In some embodiments, between about 90% to about 99% of the megakaryocyte-derived extracellular vesicles comprise a lipid bilayer membrane comprising CD147. In some embodiments, between about 95% to about 99% of the megakaryocyte-derived extracellular vesicles comprise a lipid bilayer membrane comprising CD147.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD147.

In some embodiments, between about 1% to about 15% of the megakaryocyte-derived extracellular vesicles comprise a lipid bilayer membrane comprising CD147. In some embodiments, between about 1% to about 10% of the megakaryocyte-derived extracellular vesicles comprise a lipid bilayer membrane comprising CD147. In some embodiments, between about 3% to about 8% of the megakaryocyte-derived extracellular vesicles comprise a lipid bilayer membrane comprising CD147. In some embodiments, between about 4% to about 7% of the megakaryocyte-derived extracellular vesicles comprise a lipid bilayer membrane comprising CD147.

In embodiments, the megakaryocyte-derived extracellular vesicles are characterized by a higher expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold lower amount of CD147 than platelet free plasma (PFP) MkEVs. In embodiments, the megakaryocyte-derived extracellular vesicles have about a 2-fold or about a 3-fold lower amount of CD147 than platelet free plasma (PFP) MkEVs. In embodiments, the megakaryocyte-derived extracellular vesicles have about a 1.1-fold to about a 2-fold lower amount of CD147 than platelet derived extracellular vesicles (PLT EVs). In embodiments, the megakaryocyte-derived extracellular vesicles have about a 1.1-fold or about a 1.2-fold lower amount of CD147 than platelet derived extracellular vesicles (PLT EVs). In embodiments, the megakaryocyte-derived extracellular vesicles have an amount of CD147 that is substantially the same as platelet derived extracellular vesicles (PLT EVs).

In embodiments, greater than about 50% of the megakaryocyte-derived extracellular vesicles comprise a lipid bilayer membrane comprising CD32a. In some embodiments, greater than about 40% of the megakaryocyte-derived extracellular vesicles comprise a lipid bilayer membrane comprising CD32a. In some embodiments, greater than about 60% of the megakaryocyte-derived extracellular vesicles comprise a lipid bilayer membrane comprising CD32a. In some embodiments, greater than about 70% of the megakaryocyte-derived extracellular vesicles comprise a lipid bilayer membrane comprising CD32a. In some embodiments, greater than about 80% of the megakaryocyte-derived extracellular vesicles comprise a lipid bilayer membrane comprising CD32a. In some embodiments, greater than about 90% of the megakaryocyte-derived extracellular vesicles comprise a lipid bilayer membrane comprising CD32a. In some embodiments, greater than about 95% of the megakaryocyte-derived extracellular vesicles comprise a lipid bilayer membrane comprising CD32a. In some embodiments, greater than about 99% of the megakaryocyte-derived extracellular vesicles comprise a lipid bilayer membrane comprising CD32a.

In embodiments, about 50% or less of the megakaryocyte-derived extracellular vesicles comprise a lipid bilayer membrane comprising CD32a. In some embodiments, about 40% or less of the megakaryocyte-derived extracellular vesicles comprise a lipid bilayer membrane comprising CD32a. In some embodiments, about 60% or less of the megakaryocyte-derived extracellular vesicles comprise a lipid bilayer membrane comprising CD32a. In some embodiments, about 70% or less of the megakaryocyte-derived extracellular vesicles comprise a lipid bilayer membrane comprising CD32a. In some embodiments, about 80% or less of the megakaryocyte-derived extracellular vesicles comprise a lipid bilayer membrane comprising CD32a. In some embodiments, about 90% or less of the megakaryocyte-derived extracellular vesicles comprise a lipid bilayer membrane comprising CD32a. In some embodiments, about 95% or less of the megakaryocyte-derived extracellular vesicles comprise a lipid bilayer membrane comprising CD32a. In some embodiments, about 99% or less of the megakaryocyte-derived extracellular vesicles comprise a lipid bilayer membrane comprising CD32a.

In some embodiments, less than about 50% of the megakaryocyte-derived extracellular vesicles comprise a lipid bilayer membrane comprising CD32a. In embodiments, less than about 40% of the megakaryocyte-derived extracellular vesicles comprise a lipid bilayer membrane comprising CD32a. In some embodiments, less than about 30% of the megakaryocyte-derived extracellular vesicles comprise a lipid bilayer membrane comprising CD32a. In some embodiments, less than about 25% of the megakaryocyte-derived extracellular vesicles comprise a lipid bilayer membrane comprising CD32a. In some embodiments, less than about 20% of the megakaryocyte-derived extracellular vesicles comprise a lipid bilayer membrane comprising CD32a. In some embodiments, less than about 15% of the megakaryocyte-derived extracellular vesicles comprise a lipid bilayer membrane comprising CD32a. In some embodiments, less than about 10% of the megakaryocyte-derived extracellular vesicles comprise a lipid bilayer membrane comprising CD32a. In some embodiments, less than about 5% of the megakaryocyte-derived extracellular vesicles comprise a lipid bilayer membrane comprising CD32a. In some embodiments, less than about 1% of the megakaryocyte-derived extracellular vesicles comprise a lipid bilayer membrane comprising CD32a.

In some embodiments, between about 1% to about 99% of the megakaryocyte-derived extracellular vesicles comprise a lipid bilayer membrane comprising CD32a. In some embodiments, between about 1% to about 50% of the megakaryocyte-derived extracellular vesicles comprise a lipid bilayer membrane comprising CD32a. In some embodiments, between about 1% to about 25% of the megakaryocyte-derived extracellular vesicles comprise a lipid bilayer membrane comprising CD32a. In some embodiments, between about 1% to about 10% of the megakaryocyte-derived extracellular vesicles comprise a lipid bilayer membrane comprising CD32a. In some embodiments, between about 1% to about 5% of the megakaryocyte-derived extracellular vesicles comprise a lipid bilayer membrane comprising CD32a. In some embodiments, between about 1% to about 2% of the megakaryocyte-derived extracellular vesicles comprise a lipid bilayer membrane comprising CD32a. In some embodiments, between about 50% to about 99% of the megakaryocyte-derived extracellular vesicles comprise a lipid bilayer membrane comprising CD32a. In some embodiments, between about 75% to about 99% of the megakaryocyte-derived extracellular vesicles comprise a lipid bilayer membrane comprising CD32a. In some embodiments, between about 90% to about 99% of the megakaryocyte-derived extracellular vesicles comprise a lipid bilayer membrane comprising CD32a. In some embodiments, between about 95% to about 99% of the megakaryocyte-derived extracellular vesicles comprise a lipid bilayer membrane comprising CD32a.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD32a.

In embodiments, the megakaryocyte-derived extracellular vesicles are free of, or substantially free of CD32a.

In embodiments, the megakaryocyte-derived extracellular vesicles are characterized by a higher expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 50-fold to about 100-fold, 128-fold to about a 512-fold, or about a 256-fold to about a 512-fold, or about a 250-fold to about a 300-fold lower amount of CD32a than platelet free plasma (PFP) MkEVs. In embodiments, the megakaryocyte-derived extracellular vesicles have about a 250-fold or about a 256-fold lower amount of CD32a than platelet free plasma (PFP) MkEVs. In embodiments, the megakaryocyte-derived extracellular vesicles have about a 250-fold to about a 400-fold, or a 256-fold to about a 512-fold lower amount of CD32a than platelet derived extracellular vesicles (PLT EVs). In embodiments, the megakaryocyte-derived extracellular vesicles have about a 256-fold or about a 300-fold lower amount of CD32a than platelet derived extracellular vesicles (PLT EVs).

In embodiments, greater than about 50% of the megakaryocyte-derived extracellular vesicles comprise a lipid bilayer membrane comprising GPVI. In some embodiments, greater than about 40% of the megakaryocyte-derived extracellular vesicles comprise a lipid bilayer membrane comprising GPVI. In some embodiments, greater than about 60% of the megakaryocyte-derived extracellular vesicles comprise a lipid bilayer membrane comprising GPVI. In some embodiments, greater than about 70% of the megakaryocyte-derived extracellular vesicles comprise a lipid bilayer membrane comprising GPVI a. In some embodiments, greater than about 80% of the megakaryocyte-derived extracellular vesicles comprise a lipid bilayer membrane comprising GPVI. In some embodiments, greater than about 90% of the megakaryocyte-derived extracellular vesicles comprise a lipid bilayer membrane comprising GPVI. In some embodiments, greater than about 95% of the megakaryocyte-derived extracellular vesicles comprise a lipid bilayer membrane comprising GVPI. In some embodiments, greater than about 99% of the megakaryocyte-derived extracellular vesicles comprise a lipid bilayer membrane comprising GVPI.

In embodiments, about 50% or less of the megakaryocyte-derived extracellular vesicles comprise a lipid bilayer membrane comprising GVPI. In some embodiments, about 40% or less of the megakaryocyte-derived extracellular vesicles comprise a lipid bilayer membrane comprising GVPI. In some embodiments, about 60% or less of the megakaryocyte-derived extracellular vesicles comprise a lipid bilayer membrane comprising GVPI. In some embodiments, about 70% or less of the megakaryocyte-derived extracellular vesicles comprise a lipid bilayer membrane comprising GVPI. In some embodiments, about 80% or less of the megakaryocyte-derived extracellular vesicles comprise a lipid bilayer membrane comprising GVPI. In some embodiments, about 90% or less of the megakaryocyte-derived extracellular vesicles comprise a lipid bilayer membrane comprising GVPI. In some embodiments, about 95% or less of the megakaryocyte-derived extracellular vesicles comprise a lipid bilayer membrane comprising GVPI. In some embodiments, about 99% or less of the megakaryocyte-derived extracellular vesicles comprise a lipid bilayer membrane comprising GVPI.

In some embodiments, less than about 50% of the megakaryocyte-derived extracellular vesicles comprise a lipid bilayer membrane comprising GVPI. In embodiments, less than about 40% of the megakaryocyte-derived extracellular vesicles comprise a lipid bilayer membrane comprising GVPI. In some embodiments, less than about 30% of the megakaryocyte-derived extracellular vesicles comprise a lipid bilayer membrane comprising GVPI. In some embodiments, less than about 25% of the megakaryocyte-derived extracellular vesicles comprise a lipid bilayer membrane comprising GVPI. In some embodiments, less than about 20% of the megakaryocyte-derived extracellular vesicles comprise a lipid bilayer membrane comprising GVPI. In some embodiments, less than about 15% of the megakaryocyte-derived extracellular vesicles comprise a lipid bilayer membrane comprising GVPI. In some embodiments, less than about 10% of the megakaryocyte-derived extracellular vesicles comprise a lipid bilayer membrane comprising GVPI. In some embodiments, less than about 5% of the megakaryocyte-derived extracellular vesicles comprise a lipid bilayer membrane comprising GVPI. In some embodiments, less than about 1% of the megakaryocyte-derived extracellular vesicles comprise a lipid bilayer membrane comprising GVPI.

In some embodiments, between about 1% to about 99% of the megakaryocyte-derived extracellular vesicles comprise a lipid bilayer membrane comprising GVPI. In some embodiments, between about 1% to about 50% of the megakaryocyte-derived extracellular vesicles comprise a lipid bilayer membrane comprising GVPI. In some embodiments, between about 1% to about 25% of the megakaryocyte-derived extracellular vesicles comprise a lipid bilayer membrane comprising GVPI. In some embodiments, between about 1% to about 10% of the megakaryocyte-derived extracellular vesicles comprise a lipid bilayer membrane comprising GVPI. In some embodiments, between about 1% to about 5% of the megakaryocyte-derived extracellular vesicles comprise a lipid bilayer membrane comprising GVPI. In some embodiments, between about 1% to about 2% of the megakaryocyte-derived extracellular vesicles comprise a lipid bilayer membrane comprising GVPI. In some embodiments, between about 50% to about 99% of the megakaryocyte-derived extracellular vesicles comprise a lipid bilayer membrane comprising GVPI. In some embodiments, between about 75% to about 99% of the megakaryocyte-derived extracellular vesicles comprise a lipid bilayer membrane comprising GVPI. In some embodiments, between about 90% to about 99% of the megakaryocyte-derived extracellular vesicles comprise a lipid bilayer membrane comprising GVPI. In some embodiments, between about 95% to about 99% of the megakaryocyte-derived extracellular vesicles comprise a lipid bilayer membrane comprising GVPI.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising GVPI.

In embodiments, the megakaryocyte-derived extracellular vesicles are characterized by a higher expression and/or presence of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of GPVI than naturally-occurring meg akaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold or about a 1000-fold lower amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 64-fold, or about a 16-fold to about a 32-fold greater amount of GPVI than platelet free plasma (PFP) MkEVs. In embodiments, the megakaryocyte-derived extracellular vesicles have about a 30-fold or about a 32-fold greater amount of GPVI than platelet free plasma (PFP) MkEVs. In embodiments, the megakaryocyte-derived extracellular vesicles have about a 2-fold to about a 16-fold, or about a 4-fold to about an 8-fold lower amount of GPVI than platelet derived extracellular vesicles (PLT EVs). In embodiments, the megakaryocyte-derived extracellular vesicles have about a 4-fold or about a 5-fold lower amount of GPVI than platelet derived extracellular vesicles (PLT EVs).

In embodiments, the megakaryocyte-derived extracellular vesicles are free of, or substantially free of LAMP-1 (CD107A). In embodiments, the megakaryocyte-derived extracellular vesicles have less LAMP-1 (CD107A) than naturally-occurring megakaryocyte-derived extracellular vesicles and/or vesicles or extracellular vesicles derived from platelets.

In embodiments, less than about 20%, or less than about 15%, or less than about 10%, or less than about 5% of the megakaryocyte-derived extracellular vesicles comprise a lipid bilayer membrane comprising LAMP-1 (CD107A).

In embodiments, the megakaryocyte-derived extracellular vesicles are characterized by having CD62P and being free of, or substantially free of LAMP-1 (CD107A).

In embodiments, the megakaryocyte-derived extracellular vesicles are characterized by a population of megakaryocyte-derived extracellular vesicles wherein less than about 20%, or less than about 15%, or less than about 10%, or less than about 5% of the megakaryocyte-derived extracellular vesicles comprise a lipid bilayer membrane comprising LAMP-1 (CD107A) and greater than about 40%, greater than about 50%, greater than about 60%, greater than about 70%, greater than about 80%, greater than about 90%, greater than about 95%, or greater than about 99% comprises a lipid bilayer membrane comprising CD62P.

In some embodiments, less than about 70%, or less than about 60%, or less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS).

In embodiments, the megakaryocyte-derived extracellular vesicles are characterized by a lower expression and/or presence of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by being free of, or substantially free of phosphatidylserine (PS).

In some embodiments, the megakaryocyte-derived extracellular vesicles are characterized by a population of megakaryocyte-derived extracellular vesicles wherein less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS), and greater than about 40%, greater than about 50%, greater than about 60%, greater than about 70%, greater than about 80%, greater than about 90%, greater than about 95%, or greater than about 99% of the megakaryocyte-derived extracellular vesicles comprise a lipid bilayer membrane comprising CD47.

In embodiments, the megakaryocyte-derived extracellular vesicles are characterized by a higher expression and/or presence or CD41 than naturally-occurring megakaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles and/or vesicles or extracellular vesicles derived from platelets.

In embodiments, the megakaryocyte-derived extracellular vesicles are characterized by a lower expression and/or presence or CD41 than naturally-occurring megakaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles and/or vesicles or extracellular vesicles derived from platelets.

In embodiments, the megakaryocyte-derived extracellular vesicles contain full-length filamin A.

In embodiments, the megakaryocyte-derived extracellular vesicles comprise a lipid bilayer membrane that comprises phosphatidylserine. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, greater than about 95%, or greater than about 99% comprises a lipid bilayer membrane that comprises phosphatidylserine.

In embodiments, the megakaryocyte-derived extracellular vesicles comprise a lipid bilayer membrane positive for Annexin V. For instance, Annexin V, which interacts with phosphatidylserine (PS), can be used as a surrogate for phosphatidylserine expression and/or presence or absence. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, or greater than about 95% are positive for PS.

In some embodiments, substantially all of the megakaryocyte-derived extracellular vesicles in the population comprise 2, 3, 4, 5, 6, 7, or 8 of Phosphatidylserine (PS), CD62P, LAMP-1 (CD107a), CD42b, CD9, CD43, CD31, and CD11b. In some embodiments, substantially all of the megakaryocyte-derived extracellular vesicles in the population comprise 2, 3, or 4 of PS, CD62P, CD9, and CD11b. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CD42b, CD9, CD43, CD31, and CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, or 6 of Phosphatidylserine (PS), CD61, CD62P, LAMP-1 (CD107a), CLEC-2, and CD63. In some embodiments, substantially all of the megakaryocyte-derived extracellular vesicles in the population comprise 2 or 3 of PS, CD61, and CD63. In some embodiments, substantially all of the megakaryocyte-derived extracellular vesicles in the population comprise Phosphatidylserine (PS) and CD61. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD61, CD62P, LAMP-1 (CD107a), CLEC-2, and CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, 6, 7, or 8 of Phosphatidylserine (PS), CD62P, CLEC-2, CD9, CD31, CD147, CD32a, and GPVI. In some embodiments, substantially all of the megakaryocyte-derived extracellular vesicles in the population comprise 2, 3, or 4 of Phosphatidylserine (PS), CD9, CD31, and CD147. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, CLEC-2, CD9, CD31, CD147, CD32a, and GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, of 6 of Phosphatidylserine (PS), CD62P, LAMP-1 (CD107a), CLEC-2, CD9, and CD31. In some embodiments, substantially all of the megakaryocyte-derived extracellular vesicles in the population comprise 2 or 3 of Phosphatidylserine (PS), CD62P, and CD9. In some embodiments, substantially all of the megakaryocyte-derived extracellular vesicles in the population comprise PS and CD9. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CLEC-2, CD9, and CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, the megakaryocyte-derived extracellular vesicles and/or plurality of megakaryocyte-derived extracellular vesicles and/or population of megakaryocyte-derived extracellular vesicles comprise a lipid bilayer membrane, wherein less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD54, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD18 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD43 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD11 b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD62P and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD41 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD21 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD51 and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD61 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD147 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD31 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD47 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD32a and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD9 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CLEC-2 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising LAMP-1 (CD107a) and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD24b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising GVPI and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD63, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising phosphatidylserine (PS). In some embodiments, greater than about 40%, greater than about 50%, or greater than about 60%, or greater than about 70%, or greater than about 80%, or greater than about 90%, greater than about 95%, or greater than about 99% of the megakaryocyte-derived extracellular vesicles and/or plurality of megakaryocyte-derived extracellular vesicles and/or population of megakaryocyte-derived extracellular vesicles comprise a lipid bilayer membrane comprising CD41.

Size Profile or Fingerprint

In various embodiments, the present megakaryocyte-derived extracellular vesicles are characterized by a unique size (e.g. vesicle diameter) profile or fingerprint that distinguishes them from, for instance, naturally-occurring megakaryocyte-derived extracellular vesicles and/or vesicles or extracellular vesicles derived from platelets. In various embodiments, the present megakaryocyte-derived extracellular vesicles are characterized by a such a size profile or fingerprint, which favors larger particles, e.g. as compared to naturally-occurring megakaryocyte-derived extracellular vesicles and/or vesicles or extracellular vesicles derived from platelets, that are desirable for, e.g., their higher carrying capacity.

In various embodiments, the present megakaryocyte-derived extracellular vesicles are characterized by a bias for particles of about 30 nm to about 100 nm.

In various embodiments, the present megakaryocyte-derived extracellular vesicles are characterized by a bias for particles of about 30 nm to about 400 nm.

In various embodiments, the present megakaryocyte-derived extracellular vesicles are characterized by a bias for particles of about 100 nm to about 200 nm.

In various embodiments, the present megakaryocyte-derived extracellular vesicles are characterized by a bias for particles of about 100 nm to about 300 nm.

In various embodiments, the present megakaryocyte-derived extracellular vesicles are characterized by a bias for particles of about 100 nm to about 500 nm.

In various embodiments, the present megakaryocyte-derived extracellular vesicles are characterized by a bias for particles of about 100 nm to about 600 nm.

In various embodiments, the present megakaryocyte-derived extracellular vesicles are characterized by a bias for particles of about 200 nm in diameter, on average.

In various embodiments, the present megakaryocyte-derived extracellular vesicles are characterized by a bias for particles of about 250 nm in diameter, on average.

In embodiments, the megakaryocyte-derived extracellular vesicles are substantially of a diameter of less than about 100 nm. In embodiments, the megakaryocyte-derived extracellular vesicles are substantially of a diameter in the range between about 30 nm to about 300 nm. In embodiments, the megakaryocyte-derived extracellular vesicles are substantially of a diameter in the range between about 30 nm to about 400 nm. In embodiments, the megakaryocyte-derived extracellular vesicles are substantially of a diameter in the range between about 100 nm to about 300 nm. In embodiments, the megakaryocyte-derived extracellular vesicles are substantially of a diameter in the range between about 200 nm to about 300 nm. In embodiments, the megakaryocyte-derived extracellular vesicles are substantially of a diameter in the range between about 300 nm to about 400 nm. In embodiments, the megakaryocyte-derived extracellular vesicles are substantially of a diameter in the range between about 400 nm to about 500 nm. In embodiments, the megakaryocyte-derived extracellular vesicles are substantially of a diameter in the range between about 500 nm to about 600 nm. In embodiments, the megakaryocyte-derived extracellular vesicles are substantially of a diameter in the range between about 600 nm to about 700 nm. In embodiments, the megakaryocyte-derived extracellular vesicles are substantially of a diameter in the range between about 700 nm to about 800 nm. In embodiments, the megakaryocyte-derived extracellular vesicles are substantially of a diameter in the range between about 800 nm to about 900 nm. In embodiments, the megakaryocyte-derived extracellular vesicles are substantially of a diameter in the range between about 900 nm to about 1000 nm. In embodiments, the megakaryocyte-derived extracellular vesicles are substantially of a diameter in the range between about 500 nm to about 1000 nm. In embodiments, the megakaryocyte-derived extracellular vesicles are substantially of a diameter in the range between about 600 nm to about 1000 nm. In embodiments, the megakaryocyte-derived extracellular vesicles are substantially of a diameter in the range between about 100 nm to about 500 nm. In embodiments, the megakaryocyte-derived extracellular vesicles are substantially of a diameter in the range between about 100 nm to about 600 nm. In embodiments, the megakaryocyte-derived extracellular vesicles are substantially of a diameter in the range between about 150 nm to about 500 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 200 nm to about 600 nm. In some embodiments, the megakaryocyte-derived extracellular vesicles are substantially of a diameter in the range between about 30 nm to 100 nm, or between about 30 nm to 400 nm, or between about 100 nm to about 200 nm, or between about 100 nm to about 500 nm, or between about 200 nm to about 350 nm, or between about 400 nm to about 600 nm.

In embodiments, about 90% or more, or about 95% or more, or about 97% or more, or about 99% or more of the megakaryocyte-derived extracellular vesicles are of a diameter of between about 30 to 100 nm.

In embodiments, about 90% or more, or about 95% or more, or about 97% or more, or about 99% or more of the megakaryocyte-derived extracellular vesicles are of a diameter of between about 30 to 400 nm.

In embodiments, about 90% or more, or about 95% or more, or about 97% or more, or about 99% or more of the megakaryocyte-derived extracellular vesicles are of a diameter of between about 100 nm to about 200 nm.

In embodiments, about 90% or more, or about 95% or more, or about 97% or more, or about 99% or more of the megakaryocyte-derived extracellular vesicles are of a diameter of between about 100 nm to about 300 nm.

In some embodiments, about 90% or more, or about 95% or more, or about 97% or more, or about 99% or more of the megakaryocyte-derived extracellular vesicles are of a diameter of between about 200 nm to about 350 nm.

In some embodiments, about 90% or more, or about 95% or more, or about 97% or more, or about 99% or more of the megakaryocyte-derived extracellular vesicles are of a diameter of between about 100 nm to about 600 nm.

In some embodiments, about 90% or more, or about 95% or more, or about 97% or more, or about 99% or more of the megakaryocyte-derived extracellular vesicles are of a diameter of between about 400 nm to about 600 nm.

In some embodiments, about 90% or more, or about 95% or more, or about 97% or more, or about 99% or more of the megakaryocyte-derived extracellular vesicles are of a diameter of between about 200 nm to about 600 nm.

In some embodiments, about 90% or more, or about 95% or more, or about 97% or more, or about 99% or more of the megakaryocyte-derived extracellular vesicles are of a diameter of between about 30 to about 100 nm and/or about 30 to about 400 nm and/or about 100 nm to about 200 nm and/or about 100 nm to about 300 nm and/or between about 200 nm to about 350 nm and/or between about 400 nm to about 600 nm.

In embodiments, the present compositions comprise various subpopulations of vesicles of different diameter. For example, in embodiments, present compositions comprise one or more of (e.g. one, or two, or three, or four of): a subpopulation of about 50 nm in diameter, a subpopulation of about 150 nm in diameter, a subpopulation of about 200 nm in diameter, a subpopulation of about 250 nm in diameter, a subpopulation of about 300 nm in diameter, a subpopulation of about 400 nm in diameter, a subpopulation of about 500 nm in diameter and a subpopulation of about 600 nm in diameter. In embodiments, present compositions comprise one or more of (e.g. one, or two, or three, or four of): a subpopulation of about 45 nm in diameter, a subpopulation of about 135 nm in diameter, a subpopulation of about 285 nm in diameter, and a subpopulation of about 525 nm in diameter.

In some embodiments, about 90% or more, or about 95% or more, or about 97% or more, or about 99% or more of the megakaryocyte-derived extracellular vesicles are of about 50 nm in diameter and/or about 150 nm in diameter and/or about 300 nm in diameter and/or about 500 nm in diameter.

In some embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;

b) about 90% or more, or about 95% or more, or about 97% or more, or about 99% or more of the megakaryocyte-derived extracellular vesicles are of a diameter of between about 100 nm to about 600 nm.;

c) about 40% or more, about 50% or more, about 60% or more, about 70% or more, about 80% or more, or about 90% or more of the megakaryocyte-derived extracellular vesicles in the population comprise CD41; and d) the population comprises about $1\times10^7$ or more, about $1.5\times10^7$ or more, about $5\times10^7$ or more, about $1\times10^8$ or more, about $1.5\times10^8$ or more, about $5\times10^8$ or more, about $1\times10^9$ or more, about $5\times10^9$ or more, about $1\times10^{10}$ or more, or about $1\times10^{10}$ or more megakaryocyte-derived extracellular vesicles.

In some embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;

b) about 90% or more, or about 95% or more, or about 97% or more, or about 99% or more of the megakaryocyte-derived extracellular vesicles are of a diameter of between about 100 nm to about 600 nm.;

c) about 40% or more, about 50% or more, about 60% or more, about 70% or more, about 80% or more, or about 90% or more of the megakaryocyte-derived extracellular vesicles in the population comprise CD61; and d) the population comprises about $1\times10^7$ or more, about $1.5\times10^7$ or more, about $5\times10^7$ or more, about $1\times10^8$ or more, about $1.5\times10^8$ or more, about $5\times10^8$ or more, about $1\times10^9$ or more, about $5\times10^9$ or more, about $1\times10^{10}$ or more, or about $1\times10^{10}$ or more megakaryocyte-derived extracellular vesicles.

Any method for determining the amount of nuclei in the population of megakaryocyte-derived extracellular vesicles is contemplated by the present disclosure. Non-limiting examples of methods include staining the megakaryocyte-derived extracellular vesicles with a nuclear stain such as DRAQ5, wherein a lack of staining indicates that the mega-karyocyte-derived extracellular vesicles are substantially free of nuclei.

Sources and Characterization of Megakaryocyte-Derived Extracellular Vesicles

Megakaryocytes are large, polyploid cells derived from hematopoietic stem and progenitor cells, contained within the CD34+-cell compartment. In embodiments, the mega-karyocyte is characterized by the expression and/or presence of one or more of CD41, CD62P, GPVI, CLEC-2, CD42b and CD61. In embodiments, the megakaryocyte is one or more of CD42b+, CD61+, and DNA+. One morphological characteristic of mature megakaryocytes is the development of a large, multi-lobed nucleus. Mature megakaryocytes can stop proliferating, but continue to increase their DNA content through endomitosis, with a parallel increase in cell size.

In some embodiments, in addition to extracellular vesicles, megakaryocytes can shed pre- and proplatelets and platelet-like particles. These shed moieties can mature into platelets. In some embodiments, the pre- and proplatelets and platelet-like particles are all different products, which can be differentiated by size, morphology, biomarker expression and/or presence, and function.

Megakaryocytes are derived from pluripotent hematopoi-etic stem cell (HSC) precursors. HSCs are produced primarily by the liver, kidney, spleen, and bone marrow and are capable of producing a variety of blood cells depending on the signals they receive.

Thrombopoietin (TPO) is a primary signal for inducing an HSC to differentiate into a megakaryocyte. Other molecular signals for inducing megakaryocyte differentiation include granulocyte-macrophage colony-stimulating factor (GM-CSF), Interleukin-3 (IL-3), IL-6, IL-11, SCF, fms-like tyro-sine kinase 3 ligand (FLT3L), interleukin 9 (IL-9), and the like. Production details are also described elsewhere herein.

In some embodiments, the composition comprises sub-stantially purified megakaryocyte-derived extracellular vesicles derived from a human pluripotent stem cell.

In embodiments, the human pluripotent stem cell is a primary CD34+ hematopoietic stem cell. In embodiments, the primary CD34+ hematopoietic stem cell is sourced from peripheral blood or cord blood. In embodiments, the periph-eral blood is granulocyte colony-stimulating factor-mobi-lized adult peripheral blood (mPB). In some embodiments, the human pluripotent stem cell is an HSC produced by the liver, kidney, spleen, or bone marrow. In some embodi-ments, the HSC is produced by the liver. In some embodi-ments, the HSC is produced by the kidney. In some embodi-ments, the HSC is produced by the spleen. In some embodiments, the HSC is produced by the bone marrow. In some embodiments, the HSC is induced to differentiate into a megakaryocyte by receiving a molecular signal selected from one or more of TPO, GM-CSF, IL-3, IL-6, IL-11, SCF, Flt3L, IL-9, and the like. In some embodiments, the molecu-lar signal is TPO. In some embodiments, the molecular signal is GM-CSF. In some embodiments, the molecular signal is IL-3. In some embodiments, the molecular signal is IL-6. In some embodiments, the molecular signal is IL-11. In some embodiments, the molecular signal is IL-6. In some embodiments, the molecular signal is SCF. In some embodi-ments, the molecular signal is IL-6. In some embodiments, the molecular signal is Flt3L. In some embodiments, the molecular signal is IL-6. In some embodiments, the molecu-lar signal is IL-9.

In some embodiments, the molecular signal is a chemo-kine.

In some embodiments, the molecular signal promotes cell fate decision toward megakaryopoiesis.

In some embodiments, the molecular signal is devoid of erythropoietin (EPO).

In embodiments, the human pluripotent stem cell is an embryonic stem cell (ESC). ESCs have the capacity to form cells from all three germ layers of the body, regardless of the method by which the ESCs are derived. ESCs are function-ally stem cells that can have one or more of the following characteristics: (a) be capable of inducing teratomas when transplanted in immunodeficient mice; (b) be capable of differentiating to cell types of all three germ layers (i.e. ectodermal, mesodermal, and endodermal cell types); and (c) express one or more markers of embryonic stem cells (e.g., Oct 4, alkaline phosphatase. SSEA-3 surface antigen, SSEA-4 surface antigen, SSEA-5 surface antigen, Nanog, TRA-I-60, TRA-1-81, SOX2, REX1, and the like).

In embodiments, the human pluripotent stem cell is an induced pluripotent stem cell (iPCs). Mature differentiated cells can be reprogrammed and dedifferentiated into embry-onic-like cells, with embryonic stem cell-like properties. iPSCs can be generated using fetal, postnatal, newborn, juvenile, or adult somatic cells. Fibroblast cells can be reversed into pluripotency via, for example, retroviral trans-duction of certain transcription factors, resulting in iPSs. In some embodiments, iPSs are generated from various tissues, including fibroblasts, keratinocytes, melanocyte blood cells, bone marrow cells, adipose cells, and tissue-resident pro-genitor cells. In some embodiments, iPSCs are generated via one or more reprogramming or Yamanaka factors, e.g. Oct3/4, Sox2, Klf4, and c-Myc. In certain embodiments, at least two, three, or four reprogramming factors are expressed in a somatic cell to reprogram the somatic cell.

Once a pluripotent cell has completed differentiation and become a mature megakaryocyte, it begins the process of producing platelets, which do not contain a nucleus and may be about 1-3 um in diameter. Megakaryocytes also produce extracellular vesicles.

In embodiments, the present megakaryocytes are induced to favor production of megakaryocyte-derived extracellular vesicles over platelets. That is, in embodiments, the present megakaryocytes produce substantially more megakaryo-cyte-derived extracellular vesicles than platelets. In embodi-ments, the present compositions are substantially free of platelets. In some embodiments, the present compositions contain less than about 10%, or less than about 7%, or less than about 5%, or less than about 3%, or less than about 2%, or less than about 1% platelets.

In embodiments, the present compositions are substan-tially free of extracellular vesicles derived from platelets. In some embodiments, the present compositions contain less than about 10%, or less than about 7%, or less than about 5%, or less than about 3%, or less than about 2%, or less than about 1% of extracellular vesicles derived from platelets.

In some embodiments, the megakaryocyte-derived extracellular vesicles of the disclosure are substantially free of organelles. Non-limiting examples of contaminating organelles include, but are not limited to, mitochondria, and nuclei. In some embodiments, the megakaryocyte-derived extracellular vesicles of the disclosure are substantially free of mitochondria. In some embodiments, the preparation comprising the megakaryocyte-derived extracellular vesicles of the disclosure is substantially free of exosomes. In some embodiments, megakaryocyte-derived extracellular vesicles of the disclosure comprise organelles.

In some embodiments, the megakaryocyte-derived extracellular vesicles of the disclosure are substantially free of nuclei. In some embodiments, about 80% to about 100%, about 85% to about 100%, about 90% to about 100%, or about 95% to about 100% of the megakaryocyte-derived extracellular vesicles in the population are substantially free of nuclei. In some embodiments, greater than about 80%, greater than about 85%, greater than about 90%, greater than about 95%, greater than about 99%, or about 100% of the megakaryocyte-derived extracellular vesicles in the population are substantially free of nuclei.

Targeting

Megakaryocyte-derived extracellular vesicles can home to a range of target cells. When megakaryocyte-derived extracellular vesicles bind to a target cell, they can release their cargo via various mechanisms of megakaryocyte-derived extracellular vesicle internalization by the target cell.

In embodiments, the megakaryocyte-derived extracellular vesicles are suitable for homing to bone marrow in vivo. In embodiments, the megakaryocyte-derived extracellular vesicles are suitable for homing to bone marrow in vitro. In some embodiments, the megakaryocyte-derived extracellular vesicles home in vivo to bone marrow with about a 2-fold, or about a 3-fold, or about a 4-fold, or about a 5-fold, or about a 6-fold, or about a 7-fold, or about a 8-fold, or about a 9-fold, or about a 10-fold greater specificity than to another cell type, or to another organ, or to all other cell types combined.

In some embodiments, the megakaryocyte-derived extracellular vesicles home in vivo to one or more myelopoeitic cells in bone marrow. In some embodiments, the one or more myelopoeitic cells are selected from myeloblasts, promyelocytes, neutrophilic myelocytes, eosinophilic myelocytes, neutrophilic metamyelocytes, eosinophilic metamyelocytes, neutrophilic band cells, eosinophilic band cells, segmented neutrophils, segmented eosinophils, segmented basophils, and mast cells. In some embodiments, the megakaryocyte-derived extracellular vesicles home in vivo to one or more erythropoietic cells in bone marrow. In some embodiments, the one or more erythropoietic cells are selected from pronormoblasts, basophilic normoblasts, polychromatic normoblasts, and orthochromatic normoblasts. In some embodiments, the megakaryocyte-derived extracellular vesicles home in vivo to one or more of plasma cells, reticular cells, lymphocytes, monocytes, and megakaryocytes.

In some embodiments, the megakaryocyte-derived extracellular vesicles home in vivo to one or more hematopoietic cells in bone marrow. In some embodiments, the megakaryocyte-derived extracellular vesicles home in vivo to one or more hematopoietic cells in bone marrow, e.g. thrombopoietic cells.

In some embodiments, the megakaryocyte-derived extracellular vesicles home in vivo to one or more hematopoietic stem cells in bone marrow.

In embodiments, the megakaryocyte-derived extracellular vesicles are suitable for homing to an HSC in vivo. In embodiments, the megakaryocyte-derived extracellular vesicles are suitable for homing to an HSC in vitro. In some embodiments, the megakaryocyte-derived extracellular vesicles home in vivo to an HSC with about a 2-fold greater specificity than to another cell type, or than to another organ, or than to all other cell types combined. In some embodiments, the megakaryocyte-derived extracellular vesicles home in vivo to an HSC with about a 3-fold greater specificity than to another cell type, or than to another organ, or than to all other cell types combined. In some embodiments, the megakaryocyte-derived extracellular vesicles home in vivo to an HSC with about a 4-fold greater specificity than to another cell type, or to another organ, or to all other cell types combined. In some embodiments, the megakaryocyte-derived extracellular vesicles home in vivo to an HSC with about a 5-fold greater specificity than to another cell type, or to another organ, or to all other cell types combined. In some embodiments, the megakaryocyte-derived extracellular vesicles home in vivo to an HSC with about a 6-fold greater specificity than to another cell type, or to another organ, or to all other cell types combined. In some embodiments, the megakaryocyte-derived extracellular vesicles home in vivo to an HSC with about a 7-fold greater specificity than to another cell type, or to another organ, or to all other cell types combined. In some embodiments, the megakaryocyte-derived extracellular vesicles home in vivo to an HSC with about a 8-fold greater specificity than to another cell type, or to another organ, or to all other cell types combined. In some embodiments, the megakaryocyte-derived extracellular vesicles home in vivo to an HSC with about a 9-fold greater specificity than to another cell type, or to another organ, or to all other cell types combined. In some embodiments, the megakaryocyte-derived extracellular vesicles home in vivo to an HSC with about a 10-fold greater specificity than to another cell type, or to another organ, or to all other cell types combined.

In embodiments, the megakaryocyte-derived extracellular vesicles are suitable for homing to a lymphatic cell in vivo. In embodiments, the megakaryocyte-derived extracellular vesicles are suitable for homing to a lymphatic cell in vitro. In some embodiments, the megakaryocyte-derived extracellular vesicles home in vivo to a lymphatic cell with about a 2-fold greater specificity than to another cell type, or to another organ, or to all other cell types combined. In some embodiments, the megakaryocyte-derived extracellular vesicles home in vivo to a lymphatic cell with about a 3-fold greater specificity than to another cell type, or to another organ, or to all other cell types combined. In some embodiments, the megakaryocyte-derived extracellular vesicles home in vivo to a lymphatic cell with about a 4-fold greater specificity than to another cell type, or to another organ, or to all other cell types combined. In some embodiments, the megakaryocyte-derived extracellular vesicles home in vivo to a lymphatic cell with about a 5-fold greater specificity than to another cell type, or to another organ, or to all other cell types combined. In some embodiments, the megakaryocyte-derived extracellular vesicles home in vivo to a lymphatic cell with about a 6-fold greater specificity than to another cell type, or to another organ, or to all other cell types combined. In some embodiments, the megakaryocyte-derived extracellular vesicles home in vivo to a lymphatic cell with about a 7-fold greater specificity than to another cell type, or to another organ, or to all other cell types combined. In some embodiments, the megakaryocyte-derived extracellular vesicles home in vivo to a lymphatic cell with about a 8-fold greater specificity than to another cell type, or to another organ, or to all other cell types combined. In some embodiments, the megakaryocyte-derived extracellular vesicles home in vivo to a lymphatic cell with about a 9-fold greater specificity than to another cell type, or to another organ, or to all other cell types combined. In some embodiments, the megakaryocyte-derived extracellular vesicles home in vivo to a lymphatic cell with about a 10-fold greater specificity than to another cell type, or to another organ, or to all other cell types combined.

In embodiments, the megakaryocyte-derived extracellular vesicles are suitable for homing to a regulatory T cell in vivo. In embodiments, the megakaryocyte-derived extracellular vesicles are suitable for homing to a regulatory T cell in vitro. In some embodiments, the megakaryocyte-derived extracellular vesicles home in vivo to a regulatory T cell with about a 2-fold greater specificity than to another cell type, or to another organ, or to all other cell types combined. In some embodiments, the megakaryocyte-derived extracellular vesicles home in vivo to a regulatory T cell with about a 3-fold greater specificity than to another cell type, or to another organ, or to all other cell types combined. In some embodiments, the megakaryocyte-derived extracellular vesicles home in vivo to a regulatory T cell with about a 4-fold greater specificity than to another cell type, or to another organ, or to all other cell types combined. In some embodiments, the megakaryocyte-derived extracellular vesicles home in vivo to a regulatory T cell with about a 5-fold greater specificity than to another cell type, or to another organ, or to all other cell types combined. In some embodiments, the megakaryocyte-derived extracellular vesicles home in vivo to a regulatory T cell with about a 6-fold greater specificity than to another cell type, or to another organ, or to all other cell types combined. In some embodiments, the megakaryocyte-derived extracellular vesicles home in vivo to a regulatory T cell with about a 7-fold greater specificity than to another cell type, or to another organ, or to all other cell types combined. In some embodiments, the megakaryocyte-derived extracellular vesicles home in vivo to a regulatory T cell with about a 8-fold greater specificity than to another cell type, or to another organ, or to all other cell types combined. In some embodiments, the megakaryocyte-derived extracellular vesicles home in vivo to a regulatory T cell with about a 9-fold greater specificity than to another cell type, or to another organ, or to all other cell types combined. In some embodiments, the megakaryocyte-derived extracellular vesicles home in vivo to a regulatory T cell with about a 10-fold greater specificity than to another cell type, or to another organ, or to all other cell types combined.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent to allow the therapeutic agent to associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In one aspect, the disclosure provides ex vivo methods for transferring a deliverable therapeutic agent. In some embodiments, the method comprises: (a) obtaining an megakaryocyte-derived extracellular vesicle; (b) incubating the megakaryocyte-derived extracellular vesicle with a therapeutic agent to allow the therapeutic agent to populate the lumen of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In some embodiments, the method comprises: (a) obtaining an megakaryocyte-derived extracellular vesicle; (b) incubating the megakaryocyte-derived extracellular vesicle with a therapeutic agent to allow the therapeutic agent to associate with the surface of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In some embodiments, the contacting of the deliverable therapeutic agent with the biological cell comprises co-culturing the deliverable therapeutic agent with the biological cell to provide a transfer of the cargo from the deliverable therapeutic agent to the biological cell.

In embodiments, the megakaryocyte-derived extracellular vesicles bind to a cell surface receptor on a cell of the patient. In embodiments, the megakaryocyte-derived extracellular vesicles bind to a cell surface receptor on the contacted biological cell of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles fuse with the extracellular membrane of a cell of the patient. In embodiments, the megakaryocyte-derived extracellular vesicles fuse with the extracellular membrane of the biological cells of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles are endocytosed by a cell of the patient. In embodiments, the megakaryocyte-derived extracellular vesicles are endocytosed by the biological cells of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

Methods of Producing Megakaryocyte-Derived Extracellular Vesicles

In some embodiments, a cell culture process is adapted to produce allogeneic megakaryocyte-derived extracellular vesicles from primary human peripheral blood CD34+ HSCs. In some embodiments, the megakaryocyte-derived extracellular vesicles are produced by a method comprising obtaining primary human peripheral blood CD34+ HSCs sourced from a commercial supplier and transitioning from a stem cell maintenance medium to an HSC expansion medium. In some embodiments, the megakaryocyte-derived extracellular vesicles are produced by a method comprising obtaining primary human cord blood CD34+ HSCs. In some embodiments, the megakaryocyte-derived extracellular vesicles are produced by a method comprising obtaining primary human bone marrow CD34+ HSCs. In embodiments, the method further involves placing HSC cultures in a megakaryocyte differentiation medium and collecting megakaryocyte-derived extracellular vesicles from culture supernatant. Accordingly, in embodiments, the present megakaryocyte-derived extracellular vesicles are produced from starting CD34+ HSCs.

In some embodiments, the megakaryocyte differentiation is confirmed by biomarker expression and/or presence of one or more of CD41, CD61, CD42b, megakaryocyte-specific cytoskeletal proteins 131-tubulin, alpha granule components (e.g. platelet factor 4 and von Willebrand Factor), secretory granules, and ultrastructural characteristics (e.g. invaginated membrane system, dense tubular system, multivesicular bodies).

In some embodiments, the megakaryocytes yield between about 500 to about 1500 megakaryocyte-derived extracellular vesicles/cell, which are between about 100 and about 600 nm in diameter (average about 200 nm), DNA−, and CD41+. In some embodiments, the megakaryocyte-derived extracellular vesicles are further isolated/concentrated by tangential flow filtration and packaged at targeted concentrations of about $1.5 \times 10^8$ megakaryocyte-derived extracellular vesicles/mL. In some embodiments, the megakaryocyte-derived extracellular vesicles exhibit robust expression and/or presence of megakaryocyte and platelet-specific biomarkers, RNA, and cytosolic proteins.

In some embodiments, nanoparticle analysis, electron microscopy, flow cytometry, and/or western blots are used to confirm biomarker expression and/or presence and composition of megakaryocyte-derived extracellular vesicles.

In embodiments, the megakaryocyte-derived extracellular vesicles are isolated from megakaryocytes, which are generated in the absence of added erythropoietin. In embodiments, the megakaryocyte-derived extracellular vesicles are isolated from megakaryocytes which are generated in the presence of added thrombopoietin.

In some embodiments, the megakaryocyte-derived extracellular vesicles are isolated from the source cell, such as a megakaryocyte, using a method which is substantially free of the external application of biomechanical stress (e.g. to the source cell). Non-limiting examples of methods of isolation that are substantially free of the external application of biomechanical stress include tangential flow filtration and differential centrifugation.

In some embodiments, the megakaryocyte-derived extracellular vesicles are substantially free of nucleic acids. In some embodiments, the megakaryocyte-derived extracellular vesicles are substantially free of autologous nucleic acids. In some embodiments, the megakaryocyte-derived extracellular vesicles are substantially free of RNA. In some embodiments, the megakaryocyte-derived extracellular vesicles comprise nucleic acids. In some embodiments, the megakaryocyte-derived extracellular vesicles comprise autologous nucleic acids. In some embodiments, the mega-karyocyte-derived extracellular vesicles comprise autolo-gous RNA. Non-limiting examples of RNA include rRNA, siRNA, microRNA, regulating RNA, and/or non-coding and coding RNA. In some embodiments, the megakaryocyte-derived extracellular vesicles are substantially free of RNA from the cell from which the vesicles are derived. In non-limiting examples, the megakaryocyte-derived extracellular vesicles do not contain RNA due to the method of preparing the vesicles and/or due to the use of RNase to remove native RNAs.

In some embodiments, the megakaryocyte-derived extracellular vesicles are substantially free of autologous DNA. In some embodiments, the megakaryocyte-derived extracellular vesicles are substantially free of DNA from the cell from which the vesicles are derived. In non-limiting examples, the megakaryocyte-derived extracellular vesicles do not contain DNA due to the method of preparing the vesicles and/or due to the use of DNase to remove native DNAs. In embodiments, the megakaryocyte-derived extracellular vesicles are substantially free of one or more of: (a) megakaryocytes, (b) megakaryocyte-derived platelets, and (c) extracellular vesicles derived from platelets.

In some embodiments, frozen granulocyte colony-stimulating factor (G-CSF) mobilized human peripheral blood CD34+ cells are obtained and cultured to megakaryocytes before subsequently enriching CD41+ cells (megakaryocytes) prior to culturing, and then measuring the CD41 expression and/or presence and concentration of megakaryocyte-derived extracellular vesicles in the cell culture by flow cytometer or nanoparticle analysis. In some embodiments, the megakaryocyte-derived extracellular vesicles are generated by a series of centrifugations, e.g. at escalating speeds/force. In some embodiments, the megakaryocyte-derived extracellular vesicles are generated by: (a) removing cells from culture medium at, e.g., about 150×g centrifugation for, e.g., about 10 min; (b) removing platelet-like particles (PLPs) and cell debris by centrifugation at, e.g., about 1000×g for, e.g., about 10 min; and (c) enriching the megakaryocyte-derived extracellular vesicles from the supernatant by ultracentrifugation at, e.g., about 25,000 rpm (38000×g) for, e.g., about 1 hour at, e.g., about 4° C.

In some embodiments, a multi-phase culture process with differing pH and $pO_2$ or $pCO_2$ and different cytokine cocktails is used to greatly increase megakaryocyte production.

In some embodiments, the megakaryocytes are generated by: (a) culturing CD34+ HSCs with a molecular signal/factor/cytokine cocktail that promotes megakaryocyte progenitor production; and (b) shifting cells to different conditions to expand mature megakaryocytes from progenitors. In some embodiments, commercial media is used. In some embodiments, serum-free media is used. In some embodiments, pH is shifted to increase megakaryocyte production. In some embodiments, percent $CO_2$ is shifted to increase megakaryocyte production. In some embodiments, the identity of the molecular signals/factors/cytokines is altered to increase megakaryocyte production. In embodiments, the molecular signal/factor/cytokine cocktail contains one or more of TPO, GM-CSF, IL-3, IL-6, IL-11, SCF, Flt3L, IL-9, and the like.

In embodiments, the present production methods further involve the step of characterizing the resultant megakaryocyte-derived extracellular vesicles for one or more of CD54, CD18, CD43, CD11 b, CD62P, CD41, CD61, CD21, CD51, CLEC-2, LAMP-1 (CD107a), CD63, CD42b, CD9, CD31, CD47, CD147, CD32a, and GPVI. e.g., without limitation by nanoparticle analysis, electron microscopy, flow cytometry, and/or western blot analysis. In embodiments, the present production methods further involve the step of characterizing the resultant megakaryocyte-derived extracellular vesicles for phosphatidylserine, e.g., without limitation by testing for Annexin V, e.g., without limitation by nanoparticle analysis, electron microscopy, flow cytometry, and/or western blot analysis.

In some embodiments, the megakaryocyte-derived extracellular vesicles are generated from mature megakaryocytes. In some embodiments, the megakaryocyte-derived extracellular vesicles are generated from immature megakaryocytes.

In some embodiments, methods to generate megakaryocyte-derived extracellular vesicles are standardized to enable large-scale production.

In some embodiments, the present methods to generate megakaryocyte-derived extracellular vesicles inter-batch/donor variability is of less than about 20%, or less than about 15%, or less than about 10%, or less than about 5%. In some embodiments, methods to generate megakaryocyte-derived extracellular vesicles are developed such that inter-batch/donor variability is less than 12.5%. In some embodiments, methods to generate megakaryocyte-derived extracellular vesicles are developed such that inter-batch/donor variability is less than 10%. In some embodiments, methods to generate megakaryocyte-derived extracellular vesicles are developed such that inter-batch/donor variability is less than 7.5%. In some embodiments, methods to generate megakaryocyte-derived extracellular vesicles are developed such that inter-batch/donor variability is less than 5%. In some embodiments, methods to generate megakaryocyte-derived extracellular vesicles are developed such that inter-batch/donor variability is less than 2.5%.

In some embodiments, the population comprises about $1 \times 10^7$ or more, about $1.5 \times 10^7$ or more, about $5 \times 10^7$ or more, $1 \times 10^8$ or more, about $1.5 \times 10^8$ or more, about $5 \times 10^8$ or more, about $1 \times 10^9$ or more, about $5 \times 10^9$ or more, about $1 \times 10^{10}$ or more, or about $1 \times 10^{10}$ or more megakaryocyte-derived extracellular vesicles.

In some embodiments, the megakaryocyte-derived extracellular vesicles are isolated as a population. In some embodiments, the population of megakaryocyte-derived extracellular vesicles is substantially homogenous.

In some embodiments, substantially all of the megakaryocyte-derived extracellular vesicles in the population comprise CD54. In some embodiments, about 0% to about 5%, about 0% to about 10%, about 15% to about 90%, about 30% to about 80%, or about 50% to about 70% of the megakaryocyte-derived extracellular vesicles in the population comprise CD54. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD54. In some embodiments, less than about 30%, less than about 25%, less than about 20%, less than about 15%, less than about 10%, less than about 5%, or less than about 1% of the megakaryocyte-derived extracellular vesicles in the population comprise CD54. In some embodiments, all of the megakaryocyte-derived extracellular vesicles in the population are free of, or substantially free of CD54.

In some embodiments, substantially all of the megakaryocyte-derived extracellular vesicles in the population comprise CD18. In some embodiments, about 0% to about 5%, about 0% to about 10%, about 15% to about 90%, about 30% to about 80%, or about 50% to about 70% of the megakaryocyte-derived extracellular vesicles in the population comprise CD18. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD18. In some embodiments, less than about 30%, less than about 25%, less than about 20%, less than about 15%, less than about 10%, less than about 5%, or less than about 1% of the megakaryocyte-derived extracellular vesicles in the population comprise CD18. In some embodiments, all of the megakaryocyte-derived extracellular vesicles in the population are free of, or substantially free of CD18.

In some embodiments, substantially all of the megakaryocyte-derived extracellular vesicles in the population comprise CD43. In some embodiments, about 1% to about 30%, about 1% to about 25%, about 1% to about 20%, or about 1% to about 15%, about 0% to about 5% or about 0% to about 10% of the megakaryocyte-derived extracellular vesicles in the population comprise CD43. In some embodiments, less than about 30%, less than about 25%, less than about 20%, less than about 15%, less than about 10%, less than about 5%, or less than about 1% of the megakaryocyte-derived extracellular vesicles in the population comprise CD43. In some embodiments, all of the megakaryocyte-derived extracellular vesicles in the population are free of, or substantially free of CD43.

In some embodiments, substantially all of the megakaryocyte-derived extracellular vesicles in the population comprise CD11 b. In some embodiments, about 0% to about 5%, about 0% to about 10%, about 1% to about 50%, about 5% to about 40%, or about 10% to about 35% of the megakaryocyte-derived extracellular vesicles in the population comprise CD11 b. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD11b. In some embodiments, all of the megakaryocyte-derived extracellular vesicles in the population are free of, or substantially free of CD11 b.

In some embodiments, substantially all of the megakaryocyte-derived extracellular vesicles in the population comprise CD62P. In some embodiments, about 0% to about 40%, about 0% to about 30%, about 0% to about 20%, about 0% to about 10%, or about 0% to about 5%, of the megakaryocyte-derived extracellular vesicles in the population comprise CD62P. In some embodiments, less than about 40%, less than about 30%, less than about 20%, less than about 10% of the megakaryocyte-derived extracellular vesicles in the population comprise CD62P. In some embodiments, all of the megakaryocyte-derived extracellular vesicles in the population are free of, or substantially free of CD62P.

In some embodiments, substantially all of the megakaryocyte-derived extracellular vesicles in the population comprise CD41. In some embodiments, about 15% to about 90%, about 30% to about 80%, or about 50% to about 70% of the megakaryocyte-derived extracellular vesicles in the population comprise CD41. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD41.

In some embodiments, substantially all of the megakaryocyte-derived extracellular vesicles in the population comprise CD61. In some embodiments, about 40% to about 100%, about 60% to about 100%, or about 85% to about 10% of the megakaryocyte-derived extracellular vesicles in the population comprise CD61. In some embodiments, greater than about 40%, greater than about 50%, greater than about 60%, greater than about 70%, greater than about 80%, greater than about 85%, greater than about 90%, or greater than about 95%, or greater than about 99% of the megakaryocyte-derived extracellular vesicles in the population comprise CD61.

In some embodiments, substantially all of the megakaryocyte-derived extracellular vesicles in the population comprise CD21. In some embodiments, about 0% to about 10%, about 0% to about 5%, about 15% to about 90%, about 30% to about 80%, or about 50% to about 70% of the megakaryocyte-derived extracellular vesicles in the population comprise CD21. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD21. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD21. In some embodiments, all of the megakaryocyte-derived extracellular vesicles in the population are free of, or substantially free of CD21.

In some embodiments, substantially all of the megakaryocyte-derived extracellular vesicles in the population comprise CD51. In some embodiments, about 0% to about 10%, about 0% to about 5%, about 15% to about 90%, about 30% to about 80%, or about 50% to about 70% of the megakaryocyte-derived extracellular vesicles in the population comprise CD51. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD51. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD51. In some embodiments, all of the megakaryocyte-derived extracellular vesicles in the population are free of, or substantially free of CD51.

In some embodiments, substantially all of the megakaryocyte-derived extracellular vesicles in the population comprise CLEC-2. In some embodiments, about 0% to about 10%, about 0% to about 5%, or about 0% to about 12% of the megakaryocyte-derived extracellular vesicles in the population comprise CLEC-2. In some embodiments, less than about 10%, less than about 5%, or less than about 2% of the megakaryocyte-derived extracellular vesicles in the population comprise CLEC-2. In some embodiments, all of the megakaryocyte-derived extracellular vesicles in the population are free of, or substantially free of CLEC-2.

In some embodiments, substantially all of the megakaryocyte-derived extracellular vesicles in the population comprise LAMP-1 (CD107a). In some embodiments, about 0% to about 20%, about 1% to about 15%, about 2% to about 10%, about 0% to about 5%, or about 0% to about 5% of the megakaryocyte-derived extracellular vesicles in the population comprise LAMP-1 (CD107a). In some embodiments, less than about 20%, less than about 15%, less than about 10%, or less than about 5% of the megakaryocyte-derived extracellular vesicles in the population comprise LAMP-1 (CD107a). In some embodiments, all of the megakaryocyte-derived extracellular vesicles in the population are free of, or substantially free of LAMP-1 (CD107a).

In some embodiments, less than about 20%, less than about 15%, less than about 10%, or less than about 5% of a population of CD41+ megakaryocyte-derived extracellular vesicles comprise LAMP-1 (CD107a).

In some embodiments, the megakaryocyte-derived extracellular vesicles in the population are substantially free of DRAQ5. In some embodiments, about 0% to about 20%, about 0% to about 15%, about 0% to about 10%, or about 0% to about 5% of the megakaryocyte-derived extracellular vesicles in the population comprise DRAQ5. In some embodiments, less than about 20%, less than about 15%, less than about 10%, or less than about 5% of the megakaryocyte-derived extracellular vesicles in the population comprise DRAQ5.

In some embodiments, substantially all of the megakaryocyte-derived extracellular vesicles in the population comprise CD63. In some embodiments, about 1% to about 20%, about 1% to about 15%, or about 1% to about 10% of the megakaryocyte-derived extracellular vesicles in the population comprise CD63. In some embodiments, less than about 20%, less than about 15%, less than about 10%, less than about 5%, or less than about 1% of the megakaryocyte-derived extracellular vesicles in the population comprise CD63. In some embodiments, all of the megakaryocyte-derived extracellular vesicles in the population are free of, or substantially free of CD63.

In some embodiments, substantially all of the megakaryocyte-derived extracellular vesicles in the population comprise CD42b. In some embodiments, about 0% to about 20%, about 0% to about 15%, about 0% to about 10%, or about 0% to about 5% of the megakaryocyte-derived extracellular vesicles in the population comprise CD42b. In some embodiments, less than about 20%, less than about 15%, less than about 10%, less than about 5%, or less than about 1% of the megakaryocyte-derived extracellular vesicles in the population comprise CD42b. In some embodiments, all of the megakaryocyte-derived extracellular vesicles in the population are free of, or substantially free of CD42b In some embodiments, substantially all of the megakaryocyte-derived extracellular vesicles in the population comprise CD9. In some embodiments, about 40% to about 100%, about 50% to about 80%, or about 60% to about 70% of the megakaryocyte-derived extracellular vesicles in the population comprise CD9. In some embodiments, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD9.

In some embodiments, substantially all of the megakaryocyte-derived extracellular vesicles in the population comprise CD31. In some embodiments, about 1% to about 30%, about 1% to about 25%, about 1% to about 20%, or about 1% to about 15% of the megakaryocyte-derived extracellular vesicles in the population comprise CD31. In some embodiments, less than about 30%, less than about 25%, less than about 20%, less than about 15%, less than about 10%, less than about 5%, or less than about 1% of the megakaryocyte-derived extracellular vesicles in the population comprise CD31. In some embodiments, all of the megakaryocyte-derived extracellular vesicles in the population are free of, or substantially free of CD31.

In some embodiments, substantially all of the megakaryocyte-derived extracellular vesicles in the population comprise CD47. In some embodiments, about 1% to about 40%, about 1% to about 35%, about 1% to about 20%, about 20% to about 30%, about 30% to about 40%, or about 1% to about 15% of the megakaryocyte-derived extracellular vesicles in the population comprise CD47. In some embodiments, less than about 40%, less than about 30%, less than about 25%, less than about 20%, less than about 15%, less than about 10%, less than about 5%, or less than about 1% of the megakaryocyte-derived extracellular vesicles in the population comprise CD47. In some embodiments, all of the megakaryocyte-derived extracellular vesicles in the population are free of, or substantially free of CD47.

In some embodiments, substantially all of the megakaryocyte-derived extracellular vesicles in the population comprise CD147. In some embodiments, about 1% to about 30%, about 1% to about 25%, about 1% to about 20%, about 20% to about 30%, or about 1% to about 15% of the megakaryocyte-derived extracellular vesicles in the population comprise CD147. In some embodiments, less than about 30%, less than about 25%, less than about 20%, less than about 15%, less than about 10%, less than about 5%, or less than about 1% of the megakaryocyte-derived extracellular vesicles in the population comprise CD147. In some embodiments, all of the megakaryocyte-derived extracellular vesicles in the population are free of, or substantially free of CD147.

In some embodiments, substantially all of the megakaryocyte-derived extracellular vesicles in the population comprise CD32a. In some embodiments, about 0% to about 20%, about 1% to about 15%, or about 1% to about 10% of the megakaryocyte-derived extracellular vesicles in the population comprise CD32a. In some embodiments, less than about 20%, less than about 15%, less than about 10%, less than about 5%, or less than about 1% of the megakaryocyte-derived extracellular vesicles in the population comprise CD32a. In some embodiments, all of the megakaryocyte-derived extracellular vesicles in the population are free of, or substantially free of CD32a.

In some embodiments, substantially all of the megakaryocyte-derived extracellular vesicles in the population comprise GVPI. In some embodiments, about 0% to about 5%, about 0% to about 10%, about 0% to about 30%, about 0% to about 15%, or about 0% to about 10% of the megakaryocyte-derived extracellular vesicles in the population comprise GVPI. In some embodiments, less than about 30%, less than about 25%, less than about 20%, less than about 15%, less than about 10%, less than about 5%, or less than about 1% of the megakaryocyte-derived extracellular vesicles in the population comprise GVPI. In some embodiments, all of the megakaryocyte-derived extracellular vesicles in the population are free of, or substantially free of GVPI.

In some embodiments, substantially all of the megakaryocyte-derived extracellular vesicles in the population comprise phosphatidylserine. In some embodiments, about 15% to about 90%, about 30% to about 80%, or about 50% to about 70% of the megakaryocyte-derived extracellular vesicles in the population comprise phosphatidylserine. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise phosphatidylserine. In some embodiments, less than about 30%, less than about 25%, less than about 20%, less than about 15%, less than about 10%, less than about 5%, or less than about 1% of the megakaryocyte-derived extracellular vesicles in the population comprise GVPI. In some embodiments, all of the megakaryocyte-derived extracellular vesicles in the population are free of, or substantially free of phosphatidylserine.

In some embodiments, the megakaryocyte-derived extracellular vesicles are generated by: (a) obtaining a human pluripotent stem cell being a primary CD34+ HSC sourced from peripheral blood or cord blood; (b) differentiating the human pluripotent stem cell to a megakaryocyte in the absence of added EPO and in the presence of added TPO; and (c) isolating the megakaryocyte-derived extracellular vesicles from the megakaryocytes.

In embodiments, the method is an in vivo method. In embodiments, the method is an ex vivo method.

In embodiments, the CD34+ HSC sourced from peripheral blood are multipotent stem cells derived from volunteers whose stem cells are mobilized into the bloodstream by administration of a mobilization agent such as granulocyte colony stimulating factor (G-CSF) and granulocyte-macrophage colony stimulating factor (GM-CSF).

In embodiments, the cord blood comprises multipotent stem cells derived from blood that remains in the placenta and the attached umbilical cord after childbirth.

In embodiments, the megakaryocyte-derived extracellular vesicles are autologous with the patient. In some embodiments, human pluripotent stem cells are extracted from the patient and used to generate megakaryocytes, from which megakaryocyte-derived extracellular vesicles comprising a cargo of choice are generated and then administered to the patient. In some embodiments, differentiated cells are extracted from the patient and used to generate iPSCs, which in turn are used to generate megakaryocytes, from which megakaryocyte-derived extracellular vesicles comprising a cargo of choice are generated and then administered to the patient.

In embodiments, the megakaryocyte-derived extracellular vesicles are allogeneic with the patient. In some embodiments, human pluripotent stem cells are extracted from a human subject who is not the patient and used to generate megakaryocytes, from which megakaryocyte-derived extracellular vesicles comprising a cargo of choice are generated and then administered to the patient. In some embodiments, differentiated cells are extracted from a human subject who is not the patient and used to generate iPSCs, which in turn are used to generate megakaryocytes, from which megakaryocyte-derived extracellular vesicles comprising a cargo of choice are generated and then administered to the patient.

In embodiments, the megakaryocyte-derived extracellular vesicles are heterologous with the patient. In some embodiments, pluripotent stem cells are extracted from a non-human subject and used to generate megakaryocytes, from which megakaryocyte-derived extracellular vesicles comprising a cargo of choice are generated and then administered to the patient. In some embodiments, differentiated cells are extracted from a non-human subject and used to generate iPSCs, which in turn are used to generate megakaryocytes, from which megakaryocyte-derived extracellular vesicles comprising a cargo of choice are generated and then administered to the patient.

In embodiments, the incubating comprises one or more of sonication, saponin permeabilization, mechanical vibration, hypotonic dialysis, extrusion through porous membranes, cholesterol conjugation, application of electric current and combinations thereof. In embodiments, the incubating comprises one or more of electroporating, transforming, transfecting, and microinjecting.

In embodiments, the method further comprises (d) contacting the megakaryocyte-derived extracellular vesicles with radiation. In embodiments, the radiation is gamma radiation. In embodiments, the gamma radiation is at an amount greater than 12 kGy, 25 kGy, or 50 kGy. In some embodiments, the gamma radiation is at an amount between about 12 kGy and 15 kGy. In some embodiments, the gamma radiation is at an amount between about 15 kGy and 20 kGy. In some embodiments, the gamma radiation is at an amount between about 20 kGy and 25 kGy. In some embodiments, the gamma radiation is at an amount between about 25 kGy and 30 kGy. In some embodiments, the gamma radiation is at an amount between about 30 kGy and 35 kGy. In some embodiments, the gamma radiation is at an amount between about 35 kGy and 40 kGy. In some embodiments, the gamma radiation is at an amount between about 40 kGy and 45 kGy. In some embodiments, the gamma radiation is at an amount between about 45 kGy and 50 kGy. In some embodiments, the gamma radiation is at an amount between about 50 kGy and 55 kGy. In some embodiments, the gamma radiation is at an amount between about 55 kGy and 60 kGy.

In embodiments, the method is substantially serum free. In some embodiments, the method is greater than 60% serum free. In some embodiments, the method is greater than 70% serum free. In some embodiments, the method is greater than 80% serum free. In some embodiments, the method is greater than 90% serum free.

In various embodiments, the compositions comprise substantially purified megakaryocyte-derived extracellular vesicles. In embodiments, substantially purified is synonymous with biologically pure. In embodiments, the substantially purified megakaryocyte-derived extracellular vesicles are largely free to varying degrees from components which normally accompany it as found in its native state. "Isolate" denotes a degree of separation from original source or surroundings. In embodiments, the substantially purified megakaryocyte-derived extracellular vesicles are sufficiently free of other materials such that any impurities do not materially affect the biological properties of the megakaryocyte-derived extracellular vesicles or cause other adverse consequences. In embodiments, the substantially purified megakaryocyte-derived extracellular vesicles are sufficiently free of cellular material, viral material, or culture medium that may be needed for production. Purity and homogeneity are typically determined using biochemical techniques known in the art. In some embodiments, the megakaryocyte-derived extracellular vesicles are purified using size exclusion filtration. In some embodiments, the filter has a pore size of about 650 nm. In some embodiments, the megakaryocyte-derived extracellular vesicles are purified using size exclusion filtration. In some embodiments, the filter has a pore size ranging from about 50 nm to about 600 nm. In some embodiments, the filter has a pore size of at least 50 nm. In some embodiments, the filter has a pore size of about 600 nm.

Cargo of Megakaryocyte-Derived Extracellular Vesicles

Megakaryocyte-derived extracellular vesicles may contain diverse cargo such as mRNAs, microRNAs, and cytokines. Megakaryocyte-derived extracellular vesicles are able to transfer their cargo to alter the function of target cells. They exert their influence on the target cells through surface receptor signaling, plasma membrane fusion, and internalization. By loading megakaryocytes or megakaryocyte-derived extracellular vesicles with biologic or therapeutic cargo, megakaryocyte-derived extracellular vesicles can be further used as delivery vehicles to achieve a targeted therapeutic effect. Until now, small RNAs (siRNA and miRNA), small linear DNA, and plasmid DNA have all been successfully loaded into megakaryocyte-derived extracellular vesicles for a variety of delivery applications. Megakaryocyte-derived extracellular vesicles targeting is defined by their complement of surface proteins and can be further engineered to express or remove specific biomarkers of interest to refine biodistribution and cell-cell recognition. For instance, the present megakaryocyte-derived extracellular vesicles, with their unique biomarker profiles, are particularly suited for delivery of payloads, e.g. therapies.

In embodiments, the megakaryocyte-derived extracellular vesicles are suitable for loading with cargo into the lumen. In some embodiments, the cargo is selected from one or more of a RNA, DNA, protein, carbohydrate, lipid, biomolecule, and small molecule. In some embodiments, the cargo is a biologically produced component. In some embodiments, the cargo is a synthetically produced component. In some embodiments, the cargo is pre-loaded into megakaryocyte-derived extracellular vesicles. In some embodiments, a biological component is overexpressed in megakaryocytes so that generated megakaryocyte-derived extracellular vesicles comprise the biological component. In some embodiments, the cargo is post-loaded into megakaryocyte-derived extracellular vesicles. In some embodiments, purified megakaryocyte-derived extracellular vesicles are mixed with cargo to generate cargo-loaded megakaryocyte-derived extracellular vesicles. In some embodiments, the cargo is hydrophobic. In some embodiments, the cargo is hydrophilic. In some embodiments, the cargo is integrated into the lipid bilayer of the megakaryocyte-derived extracellular vesicles. In some embodiments, the cargo is located in the lumen of the megakaryocyte-derived extracellular vesicles.

In some embodiments, in addition to or as an alternative to the cargo located in the lumen of the megakaryocyte-derived extracellular vesicles, the cargo is associated with the megakaryocyte-derived extracellular vesicles. In some embodiments, the cargo is associated with the surface and/or the exterior of the megakaryocyte-derived extracellular vesicles. Non-limiting examples of cargo associated with the megakaryocyte-derived extracellular vesicles includes cargo that is covalently conjugated to the surface of the vesicle or cargo that is associated with the surface via electrostatic interactions. As would be understood by one of ordinary skill in the art, cargo associated with the megakaryocyte-derived extracellular vesicles can still be transported even when not loaded into the lumen of the vesicle.

In some embodiments, the cargo is loaded into the megakaryocyte-derived extracellular vesicle using an active loading strategy, which is physically-induced and/or chemically-induced. In some embodiments, the active loading strategy is physically-induced. In some embodiments, the physically-induced active loading strategy comprises the mechanical or physical disruption of the megakaryocyte-derived extracellular vesicle lipid bilayer through external forces, such as electroporation, sonication, freeze-thaw cycling, and extrusion. In some embodiments, the electroporation involves the use of an electric field to induce spontaneous pore formation in the megakaryocyte-derived extracellular vesicle lipid bilayer, wherein the presence of the electric field disrupts the lipid bilayer, while removal of the field enables closure of pores and reformation of the lipid layer after the cargo has been taken up by the megakaryocyte-derived extracellular vesicle. In some embodiments, the sonication involves ultrasound energy applied through a sonicator probe that decreases the rigidity of the megakaryocyte-derived extracellular vesicle lipid bilayer, enabling cargo diffusion. In some embodiments, the freeze-thaw cycling uses thermal energy to facilitate megakaryocyte-derived extracellular vesicle cargo loading. In some embodiments, extrusion is performed following established protocols for formation of synthetic liposomes, wherein megakaryocyte-derived extracellular vesicles are mixed with free cargo and passed through membranes containing nanoscale pores, wherein the sheer force disrupts the lipid bilayer, allowing exogenous cargo to enter megakaryocyte-derived extracellular vesicles.

In some embodiments, the active loading strategy is chemically-induced. In some embodiments, the chemically-induced active loading strategy comprises the use of chemical agents, such as saponin or transfection reagents, to bypass the megakaryocyte-derived extracellular vesicle lipid bilayer. In some embodiments, the chemical agent is a detergent, such as saponin. In some embodiments, the saponin is used to selectively remove cholesterol from the megakaryocyte-derived extracellular vesicle lipid bilayer, opening pores in the lipid bilayer. In some embodiments, the chemical agent is a transfection agent. In some embodiments, the transfection agent is used to deliver nucleic acids into the megakaryocyte-derived extracellular vesicle by exploiting cationic substances that promote interactions with the lipid bilayer and subsequent internalization. In some embodiments, the transfection agent is lipofectamine and/or a lipid-based agent.

In some embodiments, the loading ratio of a nucleic acid (i.e. copies of nucleic acid per vesicle) into megakaryocyte-derived extracellular vesicles of the disclosure ranges from about 1 to about 1000, about 1 to about 500, about 1 to about 100, about 10 to about 1000, about 100 to about 1000, about 500 to about 1000, about 100 to about 500,000, about 1000 to about 300,000, about 100,000 to about 300,000, about 1000, to about 10,000, or about 1000 to about 5000. In some embodiments, the nucleic acid is DNA. In some embodiments, the nucleic acid is plasmid DNA.

In some embodiments, the loading efficiency for loading cargo, such as a nucleic acid, into megakaryocyte-derived extracellular vesicles of the disclosure ranges from about 1% to about 99%, about 10% to about 90%, about 30% to about 70%, about 40% to about 60%, about 40% to about 50%, or about 50% to about 60%. In some embodiments, the cargo is a nucleic acid. In some embodiments, the nucleic acid is DNA. In some embodiments, the nucleic acid is plasmid DNA. In some embodiments, loading efficiency is calculated using the following equation:

$$\text{Loading efficiency (\%)}=\text{cargo}+MV\#/\text{Total } MV\#$$

In some embodiments, the surface of megakaryocyte-derived extracellular vesicles is modified to impact biodistribution and targeting capabilities of megakaryocyte-derived extracellular vesicles. In some embodiments, surface ligands are added to megakaryocyte-derived extracellular vesicles through genetic engineering. In some embodiments, the megakaryocyte-derived extracellular vesicles are generated that express fusion proteins in their lipid bilayers. In some embodiments, the endogenous proteins in megakaryocyte-derived extracellular vesicle lipid bilayers are fused with targeting ligands through cell engineering.

In embodiments, the cargo is one or more therapeutic agents. In embodiments, the therapeutic agent is a nucleic acid therapeutic agent. In embodiments, the nucleic acid therapeutic agent encodes a functional protein.

In embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, DNA fragments, or DNA plasmids. In some embodiments, the nucleic acid therapeutic agent is selected from one or more of mRNA, miRNA, siRNA, and snoRNA.

In embodiments, the nucleic acid therapeutic agent encodes a wild type gene, which is defective in the patient. In embodiments, the nucleic acid therapeutic agent is mRNA, and optionally: is in vitro transcribed or synthetic and/or comprises one or more non-canonical nucleotides, optionally selected from pseudouridine and 5-methoxyuridine.

In some embodiments, the one or more non-canonical nucleotides are selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio methyl-5-azauridine, 4-thio-5-amino-5-azauridine, 4-thio-5-hydroxy-5-azauridine, 4-thio methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, the present methods comprise gene-editing and/or gene correction. In some embodiments, the present methods encompass synthetic RNA-based gene-editing and/or gene correction, e.g. with RNA comprising non-canonical nucleotides, e.g. RNA encoding one or more of a nuclease, a transcription activator-like effector nuclease (TALEN), a zinc-finger nuclease, a meganuclease, a nickase, a clustered regularly interspaced short palindromic repeat (CRISPR)-associated protein a DNA-repair protein, a DNA-modification protein, a base-modification protein, a DNA methyltransferase, a protein that causes DNA demethylation, an enzyme for which DNA is a substrate or a natural or engineered variant, family-member, orthologue, fragment or fusion construct thereof. In some embodiments, the efficiency of the gene-editing and/or gene correction is high, for example, higher than DNA-based gene editing and/or gene correction. In some embodiments, the present methods of gene-editing and/or gene correction are efficient enough for in vivo application. In some embodiments, the present methods of gene-editing and/or gene correction are efficient enough to not require cellular selection (e.g. selection of cells that have been edited). In some embodiments, the efficiency of gene-editing of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100%. In some embodiments, the efficiency of gene-correction of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100%

In some embodiments, the present methods comprise high-efficiency gene-editing proteins comprising engineered nuclease cleavage or DNA-modification domains. In some embodiments, the methods comprise high-fidelity gene-editing proteins comprising engineered nuclease cleavage or DNA-modification domains. In some embodiments, the high-efficiency gene-editing proteins comprising engineered DNA-binding domains. In some embodiments, the high-fidelity gene-editing proteins comprising engineered DNA-binding domains. In some embodiments, the methods comprise gene-editing proteins comprising engineered repeat sequences. In some embodiments, the methods comprise gene-editing proteins comprising one or more CRISPR associated family members. In some embodiments, the methods comprise altering the DNA sequence of a cell by transfecting the cell with or inducing the cell to express a gene-editing protein. In some embodiments, the methods comprise altering the DNA sequence of a cell that is present in an in vitro culture. In some embodiments, the methods comprise altering the DNA sequence of a cell that is present in vivo.

In some embodiments, the methods comprise one or more steroids and/or one or more antioxidants in the transfection medium can increase in vivo transfection efficiency, in vivo reprogramming efficiency, and in vivo gene-editing efficiency. In some embodiments, the methods comprise contacting a cell or patient with a glucocorticoid, such as hydrocortisone, prednisone, prednisolone, methylprednisolone, dexamethasone or betamethasone. In some embodiments, the methods comprise inducing a cell to express a protein of interest by contacting a cell with a medium containing a steroid and contacting the cell with one or more nucleic acid molecules. In some embodiments, the nucleic acid molecule comprises synthetic RNA. In some embodiments, the steroid is hydrocortisone. In some embodiments, the hydrocortisone is present in the medium at a concentration of between about 0.1 uM and about 10 uM, or about 1 uM. In some embodiments, the methods comprise inducing a cell in vivo to express a protein of interest by contacting the cell with a medium containing an antioxidant and contacting the cell with one or more nucleic acid molecules. In some embodiments, the antioxidant is ascorbic acid or ascorbic-acid-2-phosphate. In some embodiments, the ascorbic acid or ascorbic-acid-2-phosphate is present in the medium at a concentration of between about 0.5 mg/L and about 500 mg/L, including about 50 mg/L. In some embodiments, the methods comprise reprogramming and/or gene-editing a cell in vivo by contacting the cell with a medium containing a steroid and/or an antioxidant and contacting the cell with one or more nucleic acid molecules, wherein the one or more nucleic acid molecules encodes one or more reprogramming and/or gene-editing proteins. In some embodiments, the cell is present in an organism, and the steroid and/or antioxidant are delivered to the organism.

In embodiments, the nucleic acid therapeutic agent encodes a gene-editing protein and/or associated elements for gene-editing functionality. In embodiments, the gene-editing protein is selected from a zinc finger (ZF), transcription activator-like effector (TALE), meganuclease, and clustered regularly interspaced short palindromic repeat (CRISPR)-associated protein. In embodiments, the CRISPR-associated protein is selected from Cas9, CasX, CasY, Cpf1, and gRNA complexes thereof. In some embodiments, the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

In embodiments, the therapeutic agent is a biologic therapeutic agent. In embodiments, the biologic therapeutic agent is a protein. In some embodiments, the biologic therapeutic agent is an interferon, a monoclonal antibody, and/or an interleukin. In some embodiments, the biologic therapeutic agent is used to effect immunotherapy selected from one or more of specific active immunotherapy, nonspecific active immunotherapy, passive immunotherapy, and cytotoxic therapy.

In embodiments, the biologic therapeutic agent is a recombinant protein.

In embodiments, the biologic therapeutic agent is a virus.

In embodiments, the biologic therapeutic agent is one of an antibody or an antibody fragment, fusion protein, gene-editing protein, cytokine, antigen, and peptide.

In embodiments, the therapeutic agent is a small molecule therapeutic agent. In some embodiments, the small molecule therapeutic agent is one or more of a drug, inhibitor, or cofactor. In some embodiments, the drug for use in cancer therapy. In some embodiments, the inhibitor is one or more of a kinase inhibitor, proteasome inhibitor, and inhibitor targeting apoptosis.

In embodiments, the therapeutic agent is a vaccine and/or an immunogenic antigen.

Methods of Treatment Using Megakaryocyte-Derived Extracellular Vesicles

In various embodiments, the compositions and methods disclosed herein may be utilized for drug delivery and treatment of one or more genetic disorders.

Infectious Disease

Infectious diseases are disorders that are caused by pathogenic microorganisms, such as bacteria, viruses, fungi, or parasites. Zoonotic diseases are infectious diseases of animals that can cause disease when transmitted to humans.

In another aspect, the present invention relates to a method for treating or preventing an infectious disease, comprising administering an effective amount of a composition disclosed herein.

In another aspect, the present invention relates to a method for treating or preventing an infectious disease, comprising administering an effective amount of a composition comprising a cell, which is contacted with a composition disclosed herein in vitro.

In another aspect, the present invention relates to a method for treating or preventing an infectious disease, comprising administering an effective amount of a composition disclosed herein, wherein the composition comprises megakaryocyte-derived extracellular vesicles, which comprise cargo. In some embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In some embodiments, in addition to or as an alternative to the cargo located in the lumen of the megakaryocyte-derived extracellular vesicle, the cargo is associated with the surface of the vesicle. In some embodiments, the cargo is selected from one or more of a RNA, DNA, protein, carbohydrate, lipid, biomolecule, and small molecule. In some embodiments, the cargo is one or more therapeutic agents.

In some embodiments, the megakaryocyte-derived extracellular vesicles of the present compositions and methods are used to treat an infection caused by a virus (a viral infection) in a patient, wherein the viral infection is selected from one or more of: (a) the common cold, which mainly occurs due to rhinovirus, coronavirus, and adenovirus; (b) encephalitis and meningitis, resulting from enteroviruses and the herpes simplex virus (HSV), as well as West Nile Virus; (c) warts and skin infections, for which HPV and HSV are responsible; (d) gastroenteritis, caused by norovirus; (e) Zika; (f) AIDS/HIV; (g) Hepatitis; (h) polio; (i) influenza, including H1N1 swine flu; (j) Dengue fever; and (k) Ebola.

In some embodiments, the megakaryocyte-derived extracellular vesicles are used to treat an infection caused by a bacterium (a bacterial infection) in a patient, wherein the bacterial infection is selected from one or more of: cholera, diphtheria, dysentery, bubonic plague, tuberculosis, typhoid, typhus, bacterial meningitis, otitis media, pneumonia, upper respiratory tract infection, gastritis, food poisoning, eye infection, sinusitis, urinary tract infection, skin infection, and sexually transmitted infection.

In some embodiments, the megakaryocyte-derived extracellular vesicles are used to treat an infection caused by a fungus (a fungal infection) in a patient, wherein the fungal infection is selected from one or more of: valley fever (coccidioidomycosis), histoplasmosis, candidiasis, athlete's foot, ringworm, eye infection, and skin infection.

In some embodiments, the megakaryocyte-derived extracellular vesicles are used to treat an infection caused by a parasite (a parasitic infection) in a patient, wherein the parasitic infection is selected from one or more of: malaria, sleeping sickness, amebiasis, trypanosomiasis, pediculosis, Chagas disease, cyclosporiasis, tapeworm infection, echinococcosis, foodborne disease, giardiasis, keratitis, leishmaniasis, onchocerciasis, trichinosis, waterborne disease, and zoonotic disease.

In some embodiments, the megakaryocyte-derived extracellular vesicles are used to treat one or more symptoms associated with a coronavirus infection.

Coronaviruses (CoVs) are members of the family Coronaviridae, including betacoronavirus and alphacoronavirus-respiratory pathogens that have relatively recently become known to invade humans. The Coronaviridae family includes such betacoronavirus as Severe acute respiratory syndrome coronavirus 2 (SARS-CoV-2), SARS-CoV, Middle East Respiratory Syndrome-Corona Virus (MERS-CoV), HCoV-HKU1, and HCoV-0C43. Alphacoronavirus includes, e.g., HCoV-NL63 and HCoV-229E. In some embodiments, the present invention relates to the therapeutic use of the present megakaryocyte-derived extracellular vesicles for the treatment of one or more symptoms of infection with any of Severe acute respiratory syndrome coronavirus 2 (SARS-CoV-2), SARS-CoV, Middle East Respiratory Syndrome-Corona Virus (MERS-CoV), HCoV-HKU1, and HCoV-0C43. Alphacoronavirus includes, e.g., HCoV-NL63 and HCoV-229E.

Without wishing to be bound by theory, coronaviruses invade cells through utilization of their "spike" surface glycoprotein that is responsible for viral recognition of Angiotensin Converting Enzyme 2 (ACE2), a transmembrane receptor on mammalian hosts that facilitate viral entrance into host cells. (Zhou et al., A pneumonia outbreak associated with a new coronavirus of probable bat origin, Nature 2020).

Symptoms associated with coronavirus infections include, but are not limited to, fever, tiredness, dry cough, aches and pains, shortness of breath and other breathing difficulties, diarrhea, upper respiratory symptoms (e.g. sneezing, runny nose, nasal congestion, cough, sore throat), and/or pneumonia. In embodiments, the present compositions and methods are useful in treating or mitigating any of these symptoms.

In some embodiments, the present invention relates to the therapeutic use of the present megakaryocyte-derived extracellular vesicles for the treatment of one or more symptoms of infection with SARS-CoV-2, including Coronavirus infection 2019 (COVID-19), caused by SARS-CoV-2 (e.g., 2019-nCoV).

In embodiments, the infectious disease is a coronavirus infection. In embodiments, the coronavirus infection is infection by a betacoronavirus or an alphacoronavirus, optionally wherein the betacoronavirus is selected from a SARS-CoV-2, SARS-CoV, MERS-CoV, HCoV-HKU1, and HCoV-0C43 or the alphacoronavirus is selected from a HCoV-NL63 and HCoV-229E. In embodiments, the coronavirus infection is infection by SARS-CoV-2. In embodiments, the infectious disease is COVID-19.

In embodiments, the infectious disease is an influenza infection, optionally selected from Type A, Type B, Type C, and Type D influenza.

In embodiments, the infectious disease is a retroviral infection, optionally selected from human immune deficiency (HIV) and simian immune deficiency (SIV).

In embodiments, the composition comprises megakaryocyte-derived extracellular vesicles, which comprise a nucleic acid molecule encoding a vaccine protein and/or an immunogenic antigen. In embodiments, the composition comprises megakaryocyte-derived extracellular vesicles, which comprise a nucleic acid molecule encoding a protein related to infectivity.

In embodiments, the vaccine protein is a betacoronavirus protein or an alphacoronavirus protein, optionally wherein the betacoronavirus protein is selected from a SARS-CoV-2, SARS-CoV, MERS-CoV, HCoV-HKU1, and HCoV-0C43 protein, or an antigenic fragment thereof or the alphacoronavirus protein is selected from a HCoV-NL63 and HCoV-229E protein, or an antigenic fragment thereof.

In embodiments, the SARS-CoV-2 protein is the spike surface glycoprotein, membrane glycoprotein M, envelope protein E, and nucleocapsid phosphoprotein, or an antigenic fragment thereof. In embodiments, the spike surface glycoprotein is the S1 or S2 subunit, or an antigenic fragment thereof.

In embodiments, the nucleic acid molecule encoding a protein related to infectivity is mRNA, and the mRNA is optionally in vitro transcribed or synthetic. In embodiments, the mRNA comprises one or more non-canonical nucleotides, optionally selected from pseudouridine and 5-methoxyuridine.

In embodiments, the mRNA encodes SARS-CoV-2 spike surface glycoprotein, membrane glycoprotein M, envelope protein E, and nucleocapsid phosphoprotein, or an antigenic fragment thereof.

In embodiments, the composition comprises megakaryocyte-derived extracellular vesicles, which comprise a nucleic acid encoding a protein having reduced C-C chemokine receptor type 5 (CCR5) and C-X-C chemokine receptor type 4 (CXCR4) activity. In embodiments, the composition comprises megakaryocyte-derived extracellular vesicles, which comprise a nucleic acid molecule encoding a mutant CCR5 or CXCR4.

In embodiments, the composition comprises megakaryocyte-derived extracellular vesicles, which comprise a nucleic acid molecule encoding a gene-editing protein that is capable of reducing C-C chemokine receptor type 5 (CCR5) and C-X-C chemokine receptor type 4 (CXCR4) activity. In some embodiments, the nucleic acid molecule encoding a gene-editing protein reduces the chemokine receptor type 5 (CCR5) and C-X-C chemokine receptor type 4 (CXCR4) activity by between about 10% to about 20%. In some embodiments, the nucleic acid molecule encoding a gene-editing protein reduces the chemokine receptor type 5 (CCR5) and C-X-C chemokine receptor type 4 (CXCR4) activity by between about 20% to about 30%. In some embodiments, the nucleic acid molecule encoding a gene-editing protein reduces the chemokine receptor type 5 (CCR5) and C-X-C chemokine receptor type 4 (CXCR4) activity by between about 30% to about 40%. In some embodiments, the nucleic acid molecule encoding a gene-editing protein reduces the chemokine receptor type 5 (CCR5) and C-X-C chemokine receptor type 4 (CXCR4) activity by between about 40% to about 50%. In some embodiments, the nucleic acid molecule encoding a gene-editing protein reduces the chemokine receptor type 5 (CCR5) and C-X-C chemokine receptor type 4 (CXCR4) activity by between about 50% to about 60%. In some embodiments, the nucleic acid molecule encoding a gene-editing protein reduces the chemokine receptor type 5 (CCR5) and C-X-C chemokine receptor type 4 (CXCR4) activity by between about 60% to about 70%. In some embodiments, the nucleic acid molecule encoding a gene-editing protein reduces the chemokine receptor type 5 (CCR5) and C-X-C chemokine receptor type 4 (CXCR4) activity by between about 70% to about 80%.

Thrombocytopenias/Anemias

In various embodiments, the present invention relates to a method for treating a disease or disorder characterized by abnormal numbers or functionality of a blood cell. Such disease or disorder is, in embodiments, a genetic disease or disorder.

In various embodiments, the present invention relates to a method for treating a disease or disorder of hematopoiesis.

Thrombocytopenias relates to a serum platelet count of less than 150,000/μL. Thrombocytopenias can be stratified into mild, moderate, and severe (corresponding to platelet counts of 75,000-150,000/μL, 50,000-75,000/μL, and less than 50,000/μL, respectively).

In an aspect, the present invention relates to a method for treating a thrombocytopenia, comprising administering an effective amount of a composition disclosed herein, wherein the composition comprises megakaryocyte-derived extracellular vesicles, which comprise cargo. In some embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In some embodiments, in addition to or as an alternative to the cargo located in the lumen of the megakaryocyte-derived extracellular vesicle, the cargo is associated with the surface of the vesicle. In some embodiments, the cargo is selected from one or more of a RNA, DNA, protein, carbohydrate, lipid, biomolecule, and small molecule. In some embodiments, the cargo is one or more therapeutic agents.

In an aspect, the present invention relates to a method for treating a thrombocytopenia, comprising administering an effective amount of a composition disclosed herein, wherein the composition comprises megakaryocyte-derived extracellular vesicles, which comprise a nucleic acid encoding a functional thrombocytopenia-related gene, or a protein product thereof, or a nucleic acid encoding a gene-editing protein capable of creating a functional thrombocytopenia-related gene, or a protein product thereof.

In another aspect, the present invention relates to a method for treating a thrombocytopenia, comprising administering an effective amount of a composition comprising a cell which is contacted with a composition disclosed herein in vitro, wherein the composition comprises meg akaryocyte-derived extracellular vesicles which comprise a nucleic acid encoding a functional thrombocytopenia-related gene, or a protein product thereof, or a nucleic acid encoding a gene-editing protein capable of creating a functional thrombocytopenia-related gene, or a protein product thereof.

In some embodiments, the megakaryocyte-derived extracellular vesicles of the present compositions and methods are used to treat patients having mild thrombocytopenia. In some embodiments, the megakaryocyte-derived extracellular vesicles of the present compositions and methods are used to treat patients having moderate thrombocytopenia. In some embodiments, the megakaryocyte-derived extracellular vesicles of the present compositions and methods are used to treat patients having severe thrombocytopenia.

In some embodiments, a patient having thrombocytopenia is administered a treatment comprising megakaryocyte-derived extracellular vesicles in combination with a treatment selected from one or more of (a) platelet transfusion and (b) administration of a TPO receptor agonist.

In embodiments, the thrombocytopenia is selected from congenital amegaryocytic thrombocytopenia (CAMT), thrombocytopenia with absent radii, radio ulnar synostosis with congenital thrombocytopenia, X-linked macrothrombocytopenia with thalassemia, GB11b-related thrombocytopenia, X-Linked Thrombocytopenia/Wiskott-Aldrich syndrome, Von Willebrand diseases Type 2B, platelet-type Von Willebrand disease, CYCS-Related thrombocytopenia, immune thrombocytopenia (idiopathic thrombocytopenic purpura), and myeloablation/chemotherapy induced thrombocytopenia.

In embodiments, the thrombocytopenia is CAMT.

In embodiments, the method promotes megakaryopoeisis in the patient.

In embodiments, the method causes an increase in platelet counts in the patient.

In embodiments, the increase in platelet counts is greater than about $100 \times 10^7$ platelets/L, or greater than about $100 \times 10^8$ platelets/L, or greater than about $100 \times 10^9$ platelets/L, or greater than about $110 \times 10^9$ platelets/L, or greater than about $120 \times 10^9$ platelets/L, or greater than about $130 \times 10^9$ platelets/ L, or greater than about $140 \times 10^9$ platelets/L, or greater than about $150 \times 10^9$ platelets/L.

In embodiments, the method reduces the likelihood of the patient developing aplastic anemia and/or leukemia.

In embodiments, the method obviates the need for hematopoietic stem cell (HSC) transplantation.

In some embodiments, the patient has advanced liver disease. In some embodiments, the patient with advanced liver disease has increased concentration of von Willebrand factor as compared to a human without advanced liver disease. In some embodiments, the patient with advanced liver disease has decreased concentrations of anticoagulant factors, such as antithrombin and protein C, and/or elevated levels of procoagulant factor VIII.

In embodiments, the patient is an infant.

In embodiments, the method provides a functional thrombopoietin (TPO) receptor in the patient.

In embodiments, the gene is a functional c-Mpl gene or encodes a gene-editing protein that is capable of forming a functional c-Mpl gene.

In embodiments, the disease or disorder is characterized by abnormal (e.g. reduced relative to an undiseased state) blood cell functionality. For instance, in embodiments, the present disease or disorder may not be characterized by a reduction in blood cells numbers but activity (e.g. due to a misfunctional protein).

Hemoglobinopathies

Hemoglobinopathies are among the most common inherited diseases around the world. In some embodiments, the megakaryocyte-derived extracellular vesicles of the present methods and compositions are used to treat a hemoglobinopathy in a patient. In some embodiments, the hemoglobinopathy falls into the group of (a) thalassemia syndromes or (b) structural hemoglobin (Hb) variants (abnormal hemoglobins). In some embodiments, the thalassemia syndrome is α-thalassemia or β-thalassemia. In some embodiments, the structural hemoglobin variant is an Hb variant. In some embodiments, the structural hemoglobin variant is HbS, HbE or HbC. In some embodiments, the megakaryocyte-derived extracellular vesicles are used to treat one or more of the clinical manifestations of hemoglobinopathies selected from mild hypochromic anemia, moderate hematological disease, and severe, lifelong, transfusion-dependent anemia with multiorgan involvement.

In some embodiments, the hemoglobinopathy is sickle cell disease (SCD). Sickle cell disease (SCD) encompasses a group of hematologic disorders caused by a single nucleotide-single gene mutation transposition from a normal adenine to thymine in one or both alleles in the chromosome 11 in the SNP rs334. The transposition of thymine instead of adenine causes the transcription of an abnormal hemoglobin (e.g. HbS) that causes intermittent or permanent episodes of ischemia and/or infarction. Sickle hemoglobin changes the anatomy and elastic properties of normal hemoglobin and make red blood cells contained in sickled hemoglobin more viscous with less capacity to transport and deliver oxygen and nutrients to distal organs and tissues. In embodiments, the present compositions and methods treat heterozygous sickled hemoglobin (a.k.a. sickle cell anemia), in which both alleles are affected with a translocation of thymine (T) instead of adenine (A) in SNP rs334. In embodiments, the present compositions and methods treat heterozygous sickled hemoglobin, in which one allele is affected (A/T).

In another aspect, the present invention relates to a method for treating a hemoglobinopathy, comprising administering an effective amount of a composition disclosed herein, wherein the composition comprises megakaryocyte-derived extracellular vesicles, which comprise cargo. In some embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In some embodiments, in addition to or as an alternative to the cargo located in the lumen of the megakaryocyte-derived extracellular vesicle, the cargo is associated with the surface of the vesicle. In some embodiments, the cargo is selected from one or more of a RNA, DNA, protein, carbohydrate, lipid, biomolecule, and small molecule. In some embodiments, the cargo is one or more therapeutic agents.

In an aspect, the present invention relates to a method for treating a hemoglobinopathy, comprising administering an effective amount of a composition disclosed herein, wherein the composition comprises megakaryocyte-derived extracellular vesicles which comprise a nucleic acid encoding a functional hemoglobinopathy-related gene, or a protein product thereof, or a nucleic acid encoding a gene-editing protein capable of creating a functional hemoglobinopathy-related gene, or a protein product thereof.

In another aspect, the present invention relates to a method for treating a hemoglobinopathy, comprising administering an effective amount of a composition comprising a cell which is contacted with a composition disclosed herein in vitro, wherein the composition comprises megakaryocyte-derived extracellular vesicles which comprise a nucleic acid encoding a functional hemoglobinopathy-related gene, or a protein product thereof, or a nucleic acid encoding a gene-editing protein capable of creating a functional hemoglobinopathy-related gene, or a protein product thereof.

In some embodiments, treatment with megakaryocyte-derived extracellular vesicles is combined with one or more of (a) stem cell transplantation; (b) periodic blood transfusions for life, combined with iron chelation; and (c) drugs, including analgesics, antibiotics, ACE inhibitors, and hydroxyurea. In some embodiments, treatment with mega-karyocyte-derived extracellular vesicles is combined with diagnostic testing. In some embodiments, the diagnostic testing is selected from one or more of: (a) iron deficiency test; (b) red blood cell count; (c) DNA test; and (d) hemoglobin test.

In some embodiments, the megakaryocyte-derived extracellular vesicles are used to treat a thalassemic hemoglobin synthesis disorder. In some embodiments, the megakaryocyte-derived extracellular vesicles are used to treat a patient with abnormal hemoglobins. Sickle cell disease includes all manifestations of abnormal HbS levels, particularly HbS of greater than 50%.

In embodiments, the hemoglobinopathy is sickle cell disease. In embodiments, the hemoglobinopathy is β-thalassemia.

In embodiments, the method reduces or prevents one or more of red cell distortion, hemolytic anemia, microvascular obstruction, and ischemic tissue damage.

In embodiments, the functional hemoglobinopathy-related gene is a gene encoding a portion of hemoglobin. In embodiments, the functional hemoglobinopathy-related gene is a gene encoding one of the globin chains of hemoglobin.

In embodiments, the functional hemoglobinopathy-related gene restores hemoglobin solubility, stability, and/or oxygen affinity to undiseased levels. In some embodiments, the functional hemoglobinopathy-related gene restores hemoglobin solubility, stability, and/or oxygen affinity to between about 40% and about 50% of undiseased levels. In some embodiments, the functional hemoglobinopathy-related gene restores hemoglobin solubility, stability, and/or oxygen affinity to about 50% and about 60% of undiseased levels. In some embodiments, the functional hemoglobinopathy-related gene restores hemoglobin solubility, stability, and/or oxygen affinity to about 60% and about 70% of undiseased levels. In some embodiments, the functional hemoglobinopathy-related gene restores hemoglobin solubility, stability, and/or oxygen affinity to about 70% and about 80% of undiseased levels. In some embodiments, the functional hemoglobinopathy-related gene restores hemoglobin solubility, stability, and/or oxygen affinity to about 80% and about 90% of undiseased levels. In some embodiments, the functional hemoglobinopathy-related gene restores hemoglobin solubility, stability, and/or oxygen affinity to about 90% and about 100% of undiseased levels. In embodiments, the functional hemoglobinopathy-related gene improves hemoglobin solubility, stability, and/or oxygen affinity compared to undiseased levels. In embodiments, the functional hemoglobinopathy-related gene increases hemoglobin solubility, stability, and/or oxygen affinity. In embodiments, the functional hemoglobinopathy-related gene increases hemoglobin solubility, stability, and/or oxygen affinity compared to undiseased levels.

In embodiments, the functional hemoglobinopathy-related gene restores hemoglobin quantity to undiseased levels. In some embodiments, the functional hemoglobinopathy-related gene restores hemoglobin quantity to between about 40% and about 50% of undiseased levels. In some embodiments, the functional hemoglobinopathy-related gene restores hemoglobin quantity to about 50% and about 60% of undiseased levels. In some embodiments, the functional hemoglobinopathy-related gene restores hemoglobin quantity to about 60% and about 70% of undiseased levels. In some embodiments, the functional hemoglobinopathy-related gene restores hemoglobin quantity to about 70% and about 80% of undiseased levels. In some embodiments, the functional hemoglobinopathy-related gene restores hemoglobin quantity to about 80% and about 90% of undiseased levels. In some embodiments, the functional hemoglobinopathy-related gene restores hemoglobin quantity to about 90% and about 100% of undiseased levels. In embodiments, the functional hemoglobinopathy-related gene improves hemoglobin quantity compared to undiseased levels. In embodiments, the functional hemoglobinopathy-related gene increases hemoglobin quantity. In embodiments, the functional hemoglobinopathy-related gene increases hemoglobin quantity compared to undiseased levels In embodiments, the functional hemoglobinopathy-related gene prevents or reduces RBC sickling.

In embodiments, the functional hemoglobinopathy-related gene prevents or reduces sickle hemoglobin polymerization.

In embodiments, the functional hemoglobinopathy-related gene is beta globin (HBB). In embodiments, the gene encodes a gene-editing protein that is capable of forming a functional beta globin (HBB) gene.

Pharmaceutical Compositions

Therapeutic treatments comprise the use of one or more routes of administration and of one or more formulations that are designed to achieve a therapeutic effect at an effective dose, while minimizing toxicity to the patient to which treatment is administered.

In some embodiments, the effective dose is an amount that substantially avoids cell toxicity in vivo. In various embodiments, the effective dose is an amount that substantially avoids an immune reaction in a human patient. For example, the immune reaction may be an immune response mediated by the innate immune system. Immune response can be monitored using markers known in the art (e.g. cytokines, interferons, TLRs). In some embodiments, the effective dose obviates the need for treatment of the human patient with immune suppressants agents used to moderate the residual toxicity.

Upon formulation, solutions may be administered in a manner compatible with the dosage formulation and in such amount as is therapeutically effective, as described herein. The formulations may easily be administered in a variety of dosage forms such as injectable solutions and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art.

Pharmaceutical preparations may additionally comprise delivery reagents (a.k.a. "transfection reagents", a.k.a. "vehicles", a.k.a. "delivery vehicles") and/or excipients. Pharmaceutically acceptable delivery reagents, excipients, and methods of preparation and use thereof, including methods for preparing and administering pharmaceutical preparations to patients are well known in the art, and are set forth in numerous publications, including, for example, in US Patent Appl. Pub. No. US 2008/0213377, the entirety of which is incorporated herein by reference. In aspects, the present invention relates to a pharmaceutical composition comprising a composition disclosed herein and a pharmaceutically acceptable excipient or carrier.

For example, the present compositions can be in the form of pharmaceutically acceptable salts. Such salts include those listed in, for example, *J. Pharma. Sci.* 66, 2-19 (1977) and *The Handbook of Pharmaceutical Salts; Properties, Selection, and Use.* P. H. Stahl and C. G. Wermuth (eds.), Verlag, Zurich (Switzerland) 2002, which are hereby incorporated by reference in their entirety. Non-limiting examples of pharmaceutically acceptable salts include: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, $\alpha$-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, ch lorobenzenesu lfon ate, ethylsu lfon ate, 2-hydroxyethylsulfonate, methylsulfonate, naphthalene-1-sulfonate, naphthalene-2-sulfonate, naphthalene-1,5-sulfonate, xylenesulfonate, tartarate salts, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxytert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

The present pharmaceutical compositions can comprise excipients, including liquids such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In some embodiments, the pharmaceutically acceptable excipients are sterile when administered to a patient. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In some embodiments, the composition is formulated for one or more of topical, intrathecal, intra-lesional, intra-coronary, intravenous (IV), intra-articular, intramuscular, intra-nasal, and intra-endobronchial administration and administration via intrapancreatic endovascular injection, intra-nucleus pulposus, lumbar puncture, intra-myocardium, transendocardium, intra-fistula tract, intermedullary space, intra-nasal, and intradural space injection.

In embodiments, the composition is formulated for infusion. In some embodiments, the composition is formulated for infusion, wherein the composition is delivered to the bloodstream of a patient through a needle in a vein of the patient through a peripheral line, a central line, a tunneled line, an implantable port, and/or a catheter. In some embodiments, the patient may also receive supportive medications or treatments, such as hydration, by infusion. In some embodiments, the composition is formulated for intravenous infusion. In some embodiments, the infusion is continuous infusion, secondary intravenous therapy (IV), and/or IV push. In some embodiments, the infusion of the composition may be administered through the use of equipment selected from one or more of an infusion pump, hypodermic needle, drip chamber, peripheral cannula, and pressure bag.

In embodiments, the composition is introduced into or onto the skin, for instance. intraepidermally, intradermally or subcutaneously, in the form of a cosmeceutical (see, e.g., Epstein, H., Clin. Dermatol. 27(5):453-460 (2009)). In embodiments, the composition is in the form of a cream, lotion, ointment, gel, spray, solution and the like. In embodiments, the composition further includes a penetration enhancer such as, but not limited to, surfactants, fatty acids, bile salts, chelating agents, non-chelating non-surfactants, and the like. In embodiments, the composition may also include a fragrance, a colorant, a sunscreen, an antibacterial and/or a moisturizer.

In order that the invention disclosed herein may be more efficiently understood, examples are provided below. It should be understood that these examples are for illustrative purposes only and are not to be construed as limiting the invention in any manner.

EXAMPLES

Example 1: Megakaryocyte-Derived Extracellular Vesicle Generation

A cell culture process was adapted to produce allogeneic megakaryocyte-derived extracellular vesicles from primary human peripheral blood CD34+ hematopoietic stem cells (HSCs) (FIG. 1A).

Primary human CD34+ HSCs sourced from a commercial supplier were thawed and transitioned from a stem cell maintenance medium to an HSC expansion medium. During this period, HSCs expanded significantly. These cultures were then placed in a megakaryocyte differentiation medium, and megakaryocyte-derived extracellular vesicles were collected from culture supernatant. Biomarker expression of CD41, CD61, CD42b, megakaryocyte-specific cytoskeletal proteins $\beta$1-tubulin, alpha granule components (platelet factor 4 and von Willebrand Factor), secretory granules, and ultrastructural characteristics (invaginated membrane system, dense tubular system, multivesicular bodies) confirmed megakaryocyte differentiation. Megakaryocytes yielded between 500-1500 megakaryocyte-derived extracellular vesicles/cell, which were between 30-600 nm in diameter, 100-300 nm, DNA−, CD41+. Megakaryocyte-derived extracellular vesicles were further isolated/concentrated by tangential flow filtration and packaged at targeted concentrations of $1.5×10^8$ megakaryocyte-derived extracellular vesicles/mL. Megakaryocyte-derived extracellular vesicles exhibited robust expression of megakaryocytes and platelet-specific biomarkers, RNA, and cytosolic proteins.

Nanoparticle analysis, flow cytometry, and cryo transmission electron microscopy confirmed biomarker expression and composition.

The yield of MkEVs was found to increase over time during in vitro megakaryocyte (Mk) differentiation (FIG. 1B). The phenotype of MkEVs in culture was assessed (FIG. 1C), and representative histograms of cellular surface marker expression and microscopy images of megakaryocytes and harvested MkEVs were produced.

MkEV biomarker expression was examined. Surface marker expression of MkEVs of the disclosure were compared to platelet-free plasma (PFP) MkEVs and platelet-derived EVs (PLT EVs) (FIGS. 2A-2E). Representative graphs demonstrating the flow cytometry gating strategy (FIGS. 2A-2B), the marker profile of CD41+ MkEVs of the disclosure, CD41+ PFP MkEVs, and CD41+ PLT EVs (FIG. 2C) and the fold change in marker expression between MkEVs of the disclosure and PFP MkEVs (FIG. 2D) and MkEVs of the disclosure and PLT EVs (FIG. 2E) are shown. The data shows that MkEVs of the disclosure exhibit different expression of surface markers compared to PFP MkEVs and PLT EVs and establish a marker profile of the present MkEVs relative to PFP MkEVs and PLT EVs. The minimal presence of DRAQ5 positive events show the lack of cellular contamination (FIG. 2F).

The size and morphology of MkEVs of the disclosure were characterized. Cryo-EM images of MkEVs of the disclosure with immunogold labeling of CD41 (FIG. 3A) and phosphatidylserine (FIG. 3B) were prepared. Measuring of MkEVs in cryo-EM images showed a range of MkEV sizes between 100-300 nm, averaging ~250 nm in diameter. FIG. 3C is an image of MkEVs isolated from PFP plasma with co-staining of CD41 (large dots) and PS (small dots) (see Brisson et al., Platelets 28:263-271 (2017), which is incorporated by reference herein in its entirety). Regarding organelle content, preliminary analysis has shown no evidence of mitochondria in MkEVs, as assessed by (1) electron microscopy, and (2) mitochondrial respiration analysis (Agilent Seahorse). Genomic analysis is conducted by sequencing of coding RNAs and non-coding miRNAs. Proteomic analysis is conducted using mass spectrometry, and proteomic data validates flow and EM surface markers.

The size of MkEVs of the disclosure is compared with PFP MkEVs using flow cytometric analysis and cryo-EM analysis with CD41+ immunogold labeling. The size distribution of MkEVs of the disclosure overlapped but were different than the size distribution of PFP MkEVs and platelet-derived EVs (FIGS. 4A-4K). (FIG. 4C is adapted from Arraud et al., Journal of Thrombosis and Haemostasis 12:614-627 (2014); FIGS. 4D and 4E are found in Brisson et al., Platelets 28:263-271 (2017), all of which are incorporated by reference herein in their entireties).

Purification of MkEVs was also examined, and size exclusion filtration was found to effectively remove aggregates from unfiltered product. For example, post-harvest filtration with a 650 nm size exclusion filter was found to successfully clear large aggregate material (observed by EM in frozen MkEV samples) (FIG. 5B) compared to unfiltered MkEV product (FIG. 5A).

Example 2: MV Manufacturing Process and Release of Product for In Vivo Gene Delivery This example is related to processes for standardizing and scaling manufacturing and isolating MkEVs from primary human CD34+ HSCs. MkEVs were characterized and inter-batch variability and release testing was performed. Gene loading and transfection efficiency for MkEVs was defined, which allows for tracking in vivo biodistribution and efficacy, and defining product parameters for gene delivery applications.

For clinical entry, MkEV manufacture must meet release criteria including standardization of tissue sourcing, manufacturing, yield, testing, and storage. MkEV quality and inter-batch variability regarding identity, purity, efficacy, and yield was defined and used to define product release criteria. MkEVs met or exceed minimum quality and storage requirements.

MkEV manufacture from primary human CD34+ cells were adapted to ~400 mL batch cultures (approx. 1200 cm² of culture area, which is equivalent to ~5× T225s) to yield ~8e10 MkEVs per batch. MkEVs underwent testing to assess identity & purity (biomarker expression, % composition) and yield (total MkEV events per batch). Table 1 shows examples of MkEV release specifications.

TABLE 1

| Examples of MkEV release specifications | | |
|---|---|---|
| TEST | METHOD | SPECIFICATIONS |
| Identity/Purity | | |
| Size | Nanoparticle analyzer | ≥95% 100-600 nm |
| DNA | High sensitivity flow cytometry | ≥95% DRAQ5 negative |
| CD41 | High sensitivity flow cytometry | ≥50% positive |
| Yield | | |
| MV Events | Nanoparticle analyzer | ≥1e10 per batch |

Standardization and scale processes to manufacture and isolate MkEVs from primary human CD34+ HSCs: Primary human CD34+ hematopoietic stem cells (HSCs) were utilized. Initial isolation, enrichment, and banking of HSCs (90-95% purity) was performed and qualified according to FDA guidance using a range of assays to demonstrate identity, sterility, viability and bank stability. HSCs were mobilized from donor marrow to the blood by granulocyte-colony stimulating factor, and collected from peripheral blood by apheresis, and tested for Chagas, CMV, HepB, HepC, HIV-1/HIV-2 Plus O, HTLV I/II, Syphilis, HBV, HCV, and WNV prior to banking (COVID-19 testing is included). HSC vials were cryopreserved in clinically approved media prior to shipping and exhibit viability post thawing. In a non-limiting example, HSC vials were cryopreserved in clinically approved media prior to shipping and exhibit viability post thawing.

Process Flow for Initial Stage MkEV Production: A scalable, cGMP-compatible process to manufacture MVs from HSCs was utilized. MkEV production was divided into 2 discontinuous segments: (A) HSC expansion, megakaryocyte differentiation and MkEV production, and (B) MV isolation/concentration by tangential flow filtration and vial filling (1.5e8 MVs/mL). MkEV vials were cryopreserved for banking. Centralized manufacturing is intended for HSC expansion and MkEV production/processing/filling.

Segment A: Primary human CD34+ HSCs at a 5e6 cells/batch underwent ~30-fold biomass expansion during cell culture to yield ~1.5e8 megakaryocytes/batch. CD34+ HSC differentiation to megakaryocyte progenitor occured over a period of 7-9 days. Each megakaryocyte yielded between 500-1500 MVs, resulting in a total batch yield of ~7.5e10 MkEVs/batch prior to harvesting from supernatant.

Segment B: MkEVs were isolated/concentrated by tangential flow filtration (differential centrifugations as alternative if necessary) to reduce volume to ~500 mL. MkEVs were packaged at a concentration of ~1.5e8 MkEVs/mL to yield ~500 vials/batch.

Example 3: Characterization of MkEVs and Performance of Inter-Batch Variability and Release Testing MkEVs were collected from batch processing. High sensitivity flow cytometry was used to determine surface biomarker expression (CD41, CD62P, CLEC-2, LAMP-1 (CD107A)), organelle content (mitochondria), and phospholipid composition (phosphatidylserine) in combination with a nuclear dye (DRAQ5) to distinguish from nucleated cells. Total fluorescence intensity was calculated after subtraction of a fluorophore-conjugated IgG antibody specificity control. The forward and side light scatter of MkEVs were examined to evaluate size distribution, purity, and aggregation. Size-defined nanoparticles served as a gating control. MkEV size and total batch yield were determined using a nanoparticle analyzer (Nanosight, Malvern Instruments). MkEV protein content (Alix and TSG101) was determined by ELISA and DNA content measured to estimate potential contamination by cell debris and nuclei. MkEV integrity and purity was confirmed by cryo-electron microscopy and immunogold labeling and permit further determination of surface molecules (CD41, phosphatidylserine). These experiments were repeated a number of times per batch for a number of independent MkEV batches. In a non-limiting example, the experiments were repeated at least 3 times per batch for a minimum of 3 independent MkEV batches. MkEVs/PEVs from human whole blood were used as a positive control.

Figures 6A, 6B, 6C, 6D:
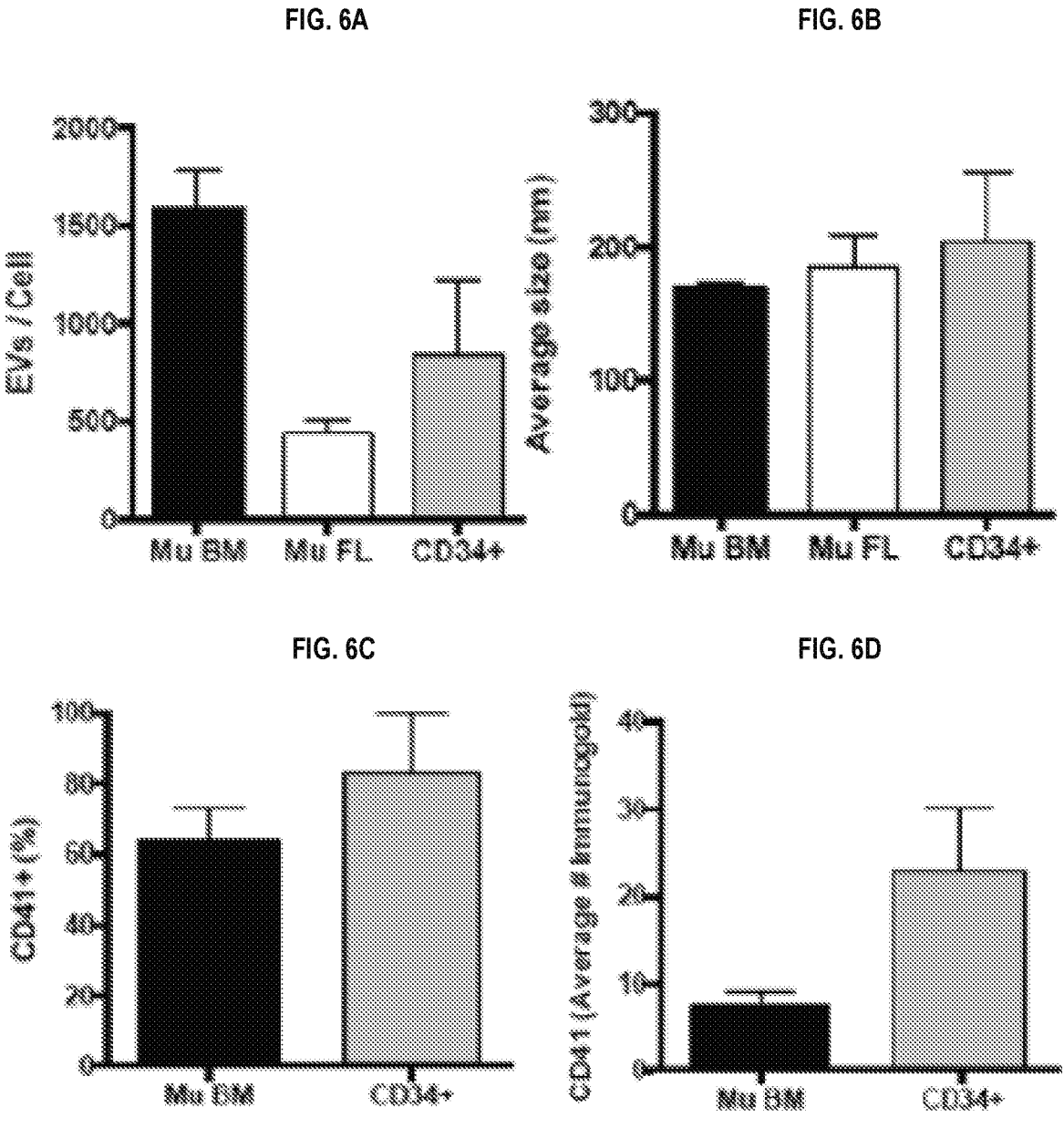
Figures 6E, 6F, 6G, 6H:
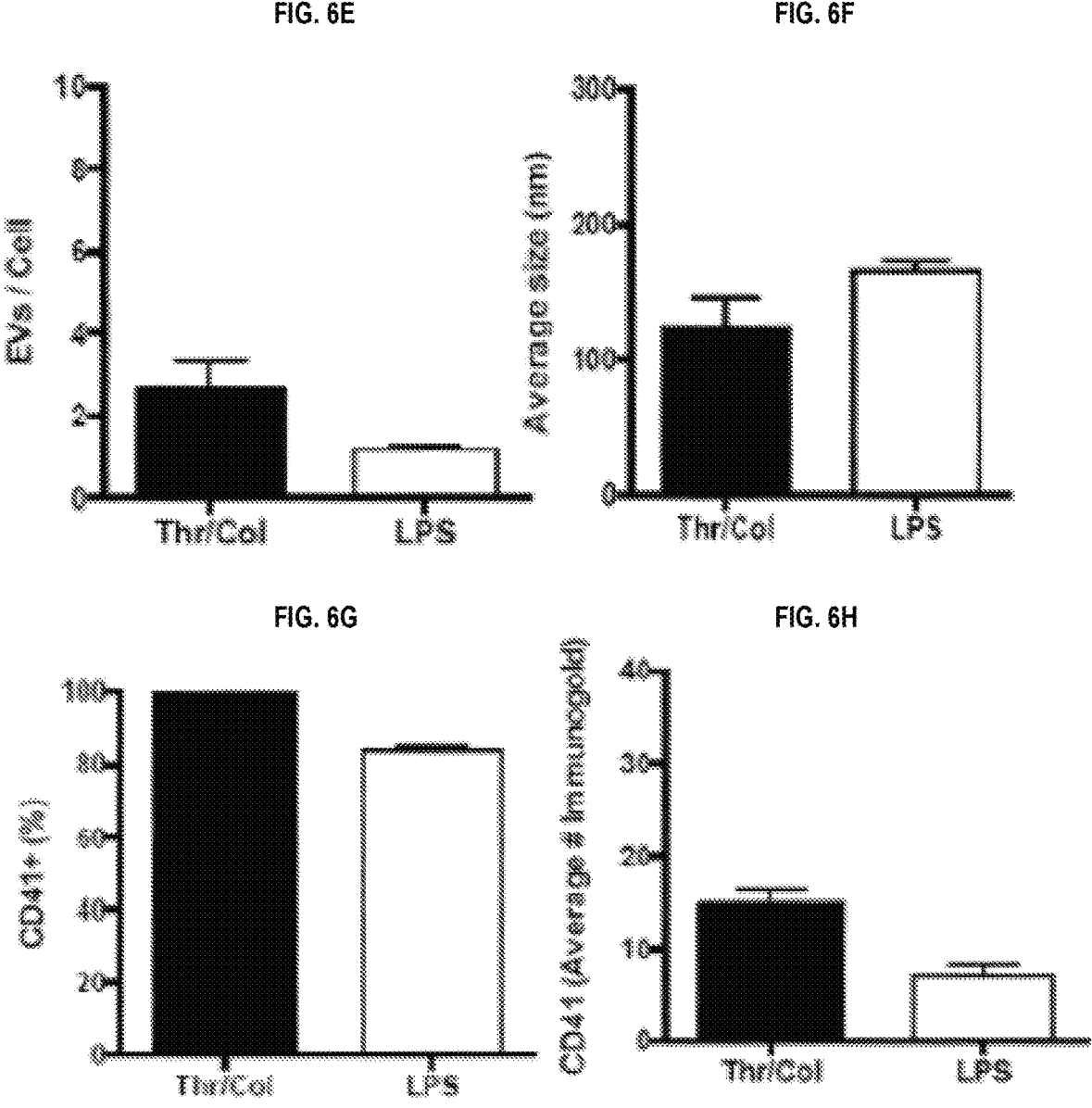

MkEVs were collected or generated from megakaryocytes and platelets, respectively, and characterized using nanoparticle tracking analysis in conjunction with immunogold labelling and electron microscopy to quantify CD41+ expression. Human CD34+-derived megakaryocytes produced between 500-1500 MkEVs per megakaryocyte (FIG. 6A), which was partway between murine bone marrow and fetal liver cell culture controls, with a similar average size of ~200 nm/MkEV (FIG. 6B). While the percentage of CD41+ MkEVs from human CD34+-derived megakaryocyte cultures were comparable to murine bone marrow-derived MkEVs, human MkEVs had more CD41-bound gold particles by immunogold electron microscopy (FIGS. 6C-6D). Human platelets activated with traditional agonists (thrombin and collagen) and inflammatory stimuli (LPS, to mimic an in vivo model) generated a similar number of EVs/platelet (FIG. 6E) and were larger in size than MkEVs (FIG. 6F) (for FIGS. 6A-6F see French et al., Blood Advances, 4:3011-3023 (2020), which is incorporated by reference herein in its entirety). Platelet-derived EVs may also contain mitochondria and other organelles (unlike MkEVs) due to their larger size. The percentage of CD41+ PEVs, and relative expression of CD41-bound gold particles by PEVs were compared to human MkEVs, and murine MkEV controls (FIGS. 6G-6H).

Example 4: Define Gene Loading and Transfection Efficiency for MkEVs

To define gene loading efficiency, ~500 bp, 3,000 bp, and 6,000 bp plasmid DNA are conjugated to a Cy5 fluorescent label using the Label IT Tracker Cy5 (Mirus); 4-10 label molecules per plasmid, as previously described. MkEVs re electroporated with Cy5+ labeled DNA at a ratio of $250\times10^3$ (DNA/MV) in 100 µL (15 min, 37° C.) using a MaxCyte VLX—a scalable cGMP compliant electroporation system that can transfect up to 200 billion cells per batch for commercial manufacturing. MkEVs are washed to ameliorate nucleic acid of MkEV aggregation and incubated on ice for 20 min to recover, and subsequently centrifuged to remove large aggregates generated during electroporation. MkEVs are washed in PBS and resuspended in co-culture medium for transfection studies. To define pDNA copy number, pDNA are purified from loaded MkEVs using the QIAprep Spin Miniprep Kit (Qiagen), and its concentration is quantified using the Qubit dsDNA HS Assay Kit (Invitrogen).

Loading efficiency (%)=$Cy5+MV\#$/Total $MV\#$ pDNA copy #=[Loaded pDNA (ng)*10^9/Molecular Weight]*Avogadro's Number Cy5 refers to the number of Cy5-positive megakaryocyte vesicles; MV #refers to the number of megakaryocyte vesicles; Loaded pDNA refers to the amount of pDNA loaded into the MVs; Molecular Weight refers to the molecular weight of the pDNA.

pDNA copy number is confirmed by quantitative PCR amplification of portion of plasmid DNA and amplicons visualized by gel electrophoresis. To define in vitro transfection efficiency MkEVs are co-cultured with CD34+ HSCs at a ratio of 25, 50, 100 MkEVs per HSC and centrifuged at 600×g for 30 min at 37° C., using previously described methods (Kao and Papoutsakis, Science Advances 4:1-11 (2018), which is incorporated by reference herein in its entirety). The percentage of Cy5+ HSCs is quantified at 24, 48, and 72 hours by flow cytometry. To define nuclear transfection efficiency nuclei are isolated for HSCs at 24 hrs as previously described, and the percent of Cy5+ nuclei quantified by flow cytometry.

Loading efficiencies per MkEV are expected to be proportionate to pDNA size; and ~50-60% transfection efficiencies. Loading efficiency and capacity of DNA in EVs are expected to be dependent on DNA size, with linear DNA molecules less than 1000 bp in length being more efficiently associated with MkEVs compared to larger linear DNAs and plasmid DNAs using this approach. If pDNA loading efficiencies are limiting, these studies are repeated with linear DNA and results compared to historical studies in other MkEVs. Other non-limiting methods for loading genetic material into MkEVs include sonication, saponin permeabilization, hypotonic dialysis, cholesterol conjugation, and megakaryocyte microinjection/transfection. Transfection efficiency studies inform in vivo dosing strategy.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A composition comprising:
a plurality of megakaryocyte-generated extracellular vesicles (MkEVs) comprising a lipid bilayer membrane surrounding a lumen, wherein:
a. the MkEV lumen comprises one or more nucleic acid molecules from the megakaryocytes selected from mRNA, tRNA, rRNA, siRNA, microRNA, regulating RNA, and non-coding and coding RNA; and,
b. the lipid bilayer membrane comprises one or more proteins associated with or embedded within, wherein the one or more proteins are selected from CD21 and GPVI; and,
C. the MkEVs are isolated from megakaryocytes derived from a human pluripotent stem cell (HPSC).

2. The composition of claim 1, wherein the lipid bilayer membrane further comprises one or more of CD9, CD63, CD47, CD43, CD54, and CD18.

3. The composition of claim 1, wherein the lipid bilayer membrane further comprises one or more of CD41, CD61, CD11b, LAMP-1 (CD107a), CD51, CD31, CD147, phosphatidylserine, CLEC-2, CD62, CD42b, and CD32a.

4. The composition of claim 1, wherein the MkEVs are of a diameter in the range between 100 nm to 300 nm.

5. The composition of claim 1, wherein the MkEVs are essentially free of:
a. megakaryocytes, and/or
b. platelets
C. organelles, and/or
d. mitochondria or nuclei.

6. The composition of claim 1, wherein the MkEVs are suitable for homing to a hematopoietic stem cell, a bone marrow, a lymphatic cell, or a regulatory T cell in vivo and/or in vitro.

7. The composition of claim 1, wherein the MkEVs are suitable for loading with cargo into the lumen and/or loading with cargo associated with the surface of the MkEVs.

8. The composition of claim 7, wherein the cargo is selected from one or more of a RNA, DNA, protein, carbohydrate, lipid, biomolecule, and small molecule.

9. The composition of claim 8, wherein the cargo is one or more therapeutic agents.

10. The composition of claim 9, wherein the therapeutic agent is selected from one or more of an antibody or an antibody fragment, recombinant protein, fusion protein, gene-editing protein, cytokine, antigen, and peptide.

11. The composition of claim 9, wherein the therapeutic agent is a nucleic acid therapeutic agent selected from one or more non-autologous and/or recombinant nucleic acid constructs selected from mRNA, tRNA, rRNA, siRNA, microRNA, regulating RNA, non-coding and coding RNA, linear DNA, DNA fragments, and DNA plasmids.

12. The composition of claim 11, wherein the nucleic acid therapeutic agent encodes a functional protein or a gene-editing protein.

* * * * *